US009512463B2

(12) United States Patent
Gelb et al.

(10) Patent No.: US 9,512,463 B2
(45) Date of Patent: Dec. 6, 2016

(54) METHODS AND COMPOSITIONS FOR ASSAYING THE ACTIVITY OF ONE OR MORE LYSOSOMAL ENZYMES

(71) Applicant: University of Washington through its Center for Commercialization, Seattle, WA (US)

(72) Inventors: Michael H. Gelb, Seattle, WA (US); Frantisek Turecek, Seattle, WA (US); Zdenek Spacil, Seattle, WA (US); C. Ronald Scott, Seattle, WA (US); Mariana Natali Barcenas Rodriguez, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 14/352,291

(22) PCT Filed: Nov. 8, 2012

(86) PCT No.: PCT/US2012/064205
§ 371 (c)(1),
(2) Date: Apr. 16, 2014

(87) PCT Pub. No.: WO2013/070953
PCT Pub. Date: May 16, 2013

(65) Prior Publication Data
US 2014/0249054 A1    Sep. 4, 2014

Related U.S. Application Data

(60) Provisional application No. 61/557,210, filed on Nov. 8, 2011.

(51) Int. Cl.
*C12Q 1/34* (2006.01)
*G01N 33/573* (2006.01)
*C12Q 1/44* (2006.01)
*G01N 30/72* (2006.01)

(52) U.S. Cl.
CPC . *C12Q 1/34* (2013.01); *C12Q 1/44* (2013.01); *G01N 33/573* (2013.01); *G01N 30/7233* (2013.01)

(58) Field of Classification Search
None
See application file for complete search history.

(56) References Cited

U.S. PATENT DOCUMENTS

| 5,773,236 | A | 6/1998 | Diwu |
| 6,670,194 | B1 | 12/2003 | Aebersold |
| 8,088,745 | B2 | 1/2012 | Gelb |
| 8,431,335 | B2* | 4/2013 | Zhang et al. ............ 435/4 |
| 9,181,184 | B2 | 11/2015 | Mugrage et al. |
| 2002/0028954 | A1* | 3/2002 | Khoury et al. .......... 549/292 |
| 2005/0148047 | A1* | 7/2005 | Clausen et al. ......... 435/68.1 |
| 2006/0264467 | A1* | 11/2006 | Mugrage et al. ........ 514/317 |
| 2008/0145836 | A1 | 6/2008 | Zhang et al. |
| 2008/0248513 | A1 | 10/2008 | Zhang |
| 2009/0306174 | A1 | 12/2009 | Liang et al. |
| 2010/0209951 | A1 | 8/2010 | Gelb |
| 2011/0118132 | A1* | 5/2011 | Winger ............ C12Q 1/00 506/7 |
| 2012/0046337 | A1* | 2/2012 | Liang et al. ............ 514/425 |
| 2012/0052519 | A1 | 3/2012 | Gelb |
| 2012/0083010 | A1* | 4/2012 | Do et al. ................. 435/18 |

FOREIGN PATENT DOCUMENTS

| JP | 2008-545657 A | 12/2008 |
| WO | 93/04192 A1 | 3/1993 |
| WO | 99/46402 A2 | 9/1999 |
| WO | 2006/102958 A1 | 10/2006 |

OTHER PUBLICATIONS

Spacil, Z. et al. Comparative Triplex Tandem MS Assays . . . Analytical Chem 83(12)4822-4828, Jun. 15, 2011.*
Blanchard, S., et al., "Short Synthetic Sequence for 2-Sulfation of α-L-Iduronate Glycosides," Carbohydrate Research 344(8):1032-1033, May 2009. (Author Manuscript provided, PMCID: PMC2680446, available in PMC May 26,2010, 4 pages).
Blanchard, S., et al., "Tandem Mass Spectrometry for the Direct Assay of Lysosomal Enzymes in Dried Blood Spots: Application to Screening Newborns for Mucopolysaccharidosis I," Clinical Chemistry 54(12):2067-2070, Dec. 2008.
Chamoles, N. A., et al., "Diagnosis of α-L-Iduronidase Deficiency in Dried Blood Spots on Filter Paper: The Possibility of Newborn Diagnosis," Clinical Chemistry 47(4):780-781, Apr. 2001.
Duffey, T.A., et al., "Design and Synthesis of Substrates for Newborn Screening of Maroteaux-Lamy and Morquio A Syndromes," Bioorganic & Medicinal Chemistry Letters 20(20):5994-5996, Oct. 2010.
Duffey, T.A., et al., "Tandem Mass Spectrometry for the Direct Assay of Lysosomal Enzymes in Dried Blood Spots: Application to Screening Newborns for Mucopolysaccharidosis VI (Maroteaux-Lamy Syndrome)," Analytical Chemistry 82(22):9587-9591, Nov. 2010. (Author Manuscript provided, PMCID: PMC2980560, available in PMC Nov. 15, 2011, 13 pages).
Duffey, T.A., et al., "Tandem Mass Spectrometry Triplex Assay for the Detection of Fabry, Pompe, and Mucopolysaccharidosis-I (Hurler)," Clinical Chemistry 56(12):1854-1861, Dec. 2010.
Gelb, M.H., et al., "Direct Multiplex Assay of Enzymes in Dried Blood Spots by Tandem Mass Spectrometry for the Newborn Screening of Lysosomal Storage Disorders," Journal of Inherited Metabolic Disease 29(2-3):397-404, Apr. 2006. (Author Manuscript provided, PMCID: PMC2488386, available in PMC Jul. 28, 2008, 13 pages).

(Continued)

*Primary Examiner* — Ralph Gitomer
(74) *Attorney, Agent, or Firm* — Christensen O'Connor Johnson Kindness PLLC

(57) ABSTRACT

Methods and liquid compositions for assaying the activity of one or more lysosomal enzymes in a sample are provided. In some embodiments, the assay is a multiplexed assay for the activities of a plurality of lysosomal enzymes in the sample. The compositions and methods can comprise or employ: one or more metal cations effective for precipitating sulfate ions, one or more metal cations effective for precipitating phosphate ions, a maltase glucoamylase inhibitor, a beta-N-acetylhexosaminidase inhibitor, and one or more surfactants.

20 Claims, 23 Drawing Sheets

(56) References Cited

OTHER PUBLICATIONS

Gerber, S.A., et al., "Design and Synthesis of Substrate and Internal Standard Conjugates for Profiling Enzyme Activity in the Sanfilippo Syndrome by Affinity Chromatography/Electrospray Ionization Mass Spectrometry," Bioconjugate Chemistry 12(4):603-615, Jul./Aug. 2001.
Hopwood, J.J., et al., "A Fluorometric Assay Using 4-Methylumbelliferyl α-L-Iduronide for the Estimation of α-L-Idurodinase Activity and the Detection of Hurler and Scheie Syndromes," Clinica Chimica Act 92(2):257-265, Mar. 1979.
International Search Report and Written Opinion of the International Searching Authority, mailed Feb. 2, 2009, in related International Application No. PCT/US2008/073516, filed Aug. 18, 2008, 11 pages.
International Search Report and Written Opinion mailed Mar. 22, 2013, issued in corresponding International Application No. PCT/US2012/064205, filed Nov. 8, 2012, 7 pages.
Khaliq, T., et al., "Tandem Mass Spectrometry for the Direct Assay of Lysosomal Enzymes in Dried Blood Spots: Application to Screening Newborns for Mucopolysaccharidosis IVA," Clinical Chemistry 57(1):128-131, Jan. 2011.
Li, Y. et al "Direct Multiplex Assay of Lysosomal Enzymes in Dried Blood Spots for Newborn Screening," Clinical Chemistry 50(10):1785-1796, Oct. 2004.
Li, Y. et al "Tandem Mass Spectrometry for the Direct Assay of Enzymes in Dried Blood Spots: Application to Newborn Screening for Krabbe Disease," Clinical Chemistry 50(3):638-640, Mar. 2004.
Mandelli, J., et al., "Detection of Mucopolysaccharidosis Type I Heterozygotes Based on the Biochemical Characteristics of Leukocyte α-L-Iduronidase," Archives of Medical Research 33(1):20-24, Jan. 2002.
Orsini, J.J., et al., "Lysosomal Storage Disorder 4+1 Multiplex Assay for Newborn Screening Using Tandem Mass Spectrometry: Application to a Small-Scale Population Study for Five Lysosomal Storage Disorders," Clinica Chimica Acta 413(15-16):1270-1273, Aug. 2012. (Author Manuscript provided, PMCID: PMC3443687, available in PMC Sep. 16, 2012, 12 pages).
Scott, C.R., et al., "Identification of Infants at Risk for Developing Fabry, Pompe, or Mucopolysaccharidosis-I from Newborn Blood Spots by Tandem Mass Spectrometry," Journal of Pediatrics 163(2):498-503, Aug. 2013.
Spáčil, Z., et al., "Comparative Triplex Tandem Mass Spectrometry Assays of Lysosomal Enzyme Activities in Dried Blood Spots Using Fast Liquid Chromatography: Application to Newborn Screening of Pompe, Fabry, and Hurler Diseases," Analytical Chemistry 83(12):4822-4828, Jun. 2011. (Author Manuscript provided, PMCID: PMC3115456, available in PMC Jun. 15, 2012, 12 pages).
Spáčil, Z., et al., "High-Throughput Assay of 9 Lysosomal Enzymes for Newborn Screening," Clinical Chemistry 59(3):502-511, Mar. 2013.
Spáčil, Z., et al., "Protonation Sites and Dissociation Mechanisms of t-Butylcarbamates in Tandem Mass Spectrometric Assays for Newborn Screening," Journal of Mass Spectrometry 46(10):1089-1098, Oct. 2011. (Author Manuscript provided, PMCID: PMC3212097, available in PMC Oct. 1, 2012, 22 pages).
Tureček, F., et al., "Tandem Mass Spectrometry in the Detection of Inborn Errors of Metabolism for Newborn Screening," in S. Sechi (ed.), "Methods in Molecular Biology: Quantitative Proteomics by Mass Spectrometry," Humana Press Inc., Totowa, N.J., 2007, vol. 359, pp. 143-157.
Wang, D., et al., "Tandem Mass Spectrometric Analysis of Dried Blood Spots for Screening of Mucopolysaccharidosis I in Newborns," Clinical Chemistry 51(5):898-900, May 2005.
Wang, D., et al., "Tandem Mass Spectrometry for the Direct Assay of Enzymes in Dried Blood Spots: Application to Newborn Screening for Mucopolysaccharidosis II (Hunter Disease)," Clinical Chemistry 53(1):137-140, Jan. 2007.
Wolfe, B.J., et al., "New Substrates and Enzyme Assays for the Detection of Mucopolysaccharidosis III (Sanfilippo Syndrome) Types A, B, C, and D by Tandem Mass Spectrometry," Bioconjugate Chemistry 23(3):557-564, Mar. 2012.
Wolfe, B.J., et al., "Tandem Mass Spectrometry for the Direct Assay of Lysosomal Enzymes in Dried Blood Spots: Application to Screening Newborns for Mucopolysaccharidosis II (Hunter Syndrome)," Analytical Chemistry 83(3):1152-1156, Feb. 2011. (Author Manuscript provided, PMCID: PMC3442111, available in PMC Sep. 13, 2012, 11 pages).
Zhang, X.K., et al., "Multiplex Lysosomal Enzyme Activity Assay on Dried Blood Spots Using Tandem Mass Spectrometry," in U. Garg et al. (eds.), "Methods in Molecular Biology: Clinical Applications of Mass Spectrometry," Humana Press Inc., New York, 2010, vol. 603, pp. 339-350.
Extended European Search Report dated Jun. 11, 2015, issued in corresponding European Application No. 12847334.5, filed Nov. 8, 2012, 12 pages.
Liu, J., et al., "Hexosaminidase Inhibitors as New Drug Candidates for the Therapy of Osteoarthritis," Chemistry & Biology 8(7):701-711, Jul. 2001.
Metz, T.F., et al., "Simplified Newborn Screening Protocol for Lysosomal Storage Disorders," Clinical Chemistry 57(9):1286-1294, Jul. 2011.
Offce Action (EP) mailed Jul. 8, 2016, issued in corresponding European Application No. 12847334.5, filed Nov. 3, 2012, 5 pages.
Offce Action (JP) mailed Jul. 5, 2016, issued in corresponding Japanese Application No. 2014-541270, filed Nov. 8, 2012, 4 pages.
Lemieux, M.J., et al., "Crystallographic Structure of Human β-Hexosaminidase A: Interpretation of Tay-Sachs Mutations and Loss of GM2 Ganglioside Hydrolysis." Journal of Molecular Biology 359(4): 913-929, Jun. 2006.

* cited by examiner

METHODS AND COMPOSITIONS FOR ASSAYING THE ACTIVITY OF ONE OR MORE LYSOSOMAL ENZYMES

CROSS-REFERENCE TO RELATED APPLICATIONS

This application is a National Stage filed under Rule 371 based upon PCT/US2012/064205 filed Nov. 8, 2012, which claims the benefit of U.S. Patent Application No. 61/557,210, filed Nov. 8, 2011, expressly incorporated herein by reference in its entirety.

STATEMENT OF GOVERNMENT LICENSE RIGHTS

This invention was made with Government support under DK67859 awarded by the National Institutes of Health. The Government has certain rights in the invention.

BACKGROUND OF THE INVENTION

Treatments for a subset of lysosomal storage disorders (LSDs) have become available, and in many cases, early initiation of therapy leads to a clinical improvement. These encouraging results have spawned widespread interest in newborn screening of LSDs.

Newborn screening programs have been established to quantify the level of metabolites associated with these treatable diseases. New York State now provides Krabbe disease screening and recent legislation for LSD expanded newborn screening has passed in several other states, and newborn screening for Pompe and Fabry diseases is carried out in Taiwan.

The mucopolysaccharidoses (MPS I to VII) are a group of metabolic diseases/syndromes caused by a deficiency of one of the lysosomal enzymes degrading the glycosaminoglycans heparan, dermatan, keratan, or chondroitin sulfate. The pertinent enzymes include five sulfatases, four exoglycosidases, and one non-hydrolytic acetyl-N-transferase. These syndromes result in non-degraded or partially-degraded glycosaminoglycans amassing in the lysosome resulting in irreversible multi-systemic organ damage.

Although treatments have recently become available for some of the MPS syndromes, optimal benefits from these treatments would require commencement of treatment prior to the onset of the irreversible symptoms. Early detection of MPS syndromes maximizes the potential benefit of treatment, and thus there is the need to develop tests that are appropriate for early diagnosis. Likewise, there is a need for developing a fast, inexpensive, and reliable diagnostic procedure that uses dried blood spots (DBS) as a sample source, such as those submitted to newborn screening laboratories.

Accordingly, a need exists for methods and reagents for newborn screening of the activity of lysosomal enzymes, particularly methods and reagents that allow for multiplexed enzyme analysis. The present invention fulfills this need and provides further related advantages.

SUMMARY OF THE INVENTION

In one aspect, the invention provides a method for assaying enzymatic activities of one or more lysosomal enzymes. In one embodiment, the method includes:
(a) contacting a sample with a first solution to provide a solution comprising one or more lysosomal enzymes;
(b) adding an enzyme substrate for each lysosomal enzyme to be analyzed to the solution comprising the enzymes and incubating the substrates with the enzymes in an enzyme reaction solution for a time sufficient to provide a solution comprising an enzyme product for each lysosomal enzyme present in the sample, wherein the enzyme reaction solution comprises:
  (i) one or more metal cations effective for precipitating sulfate ions;
  (ii) one or more metal cations effective for precipitating phosphate ions;
  (iii) a maltase glucoamylase inhibitor;
  (iv) a beta-N-acetylhexosaminidase inhibitor; and
  (v) one or more surfactants;
(c) optionally quenching the enzyme reaction; and
(d) determining the quantities of the enzyme products.

In certain embodiments, the method further includes adding an internal standard for each lysosomal enzyme to be analyzed before, after, or simultaneously with the addition of the one or more substrates.

Suitable samples useful in the methods of the invention include blood and tissue samples. In one embodiment, the sample is a dried blood spot such as a dried blood spot from a newborn screening card.

In certain embodiments, determining the quantities of the enzyme products comprises determining the ratio of each product to its internal standard by mass spectrometric analysis. Representative mass spectrometric analysis includes tandem mass spectrometric analysis. For tandem mass spectrometric analysis, determining the quantities of the products comprises tandem mass spectrometric analysis in which the parent ions of the products and their internal standards are generated, isolated, and subjected to collision-induced dissociation to provide product fragment ions and internal standard fragment ions. In certain embodiments, determining the quantities of the products comprises comparing the peak intensities of the product fragment ions and internal standard fragment ions to calculate the amount of the products. In embodiments of the invention, the quantities of the products can be used to determine whether the dried blood sample is from a candidate for treatment for a condition associated with one or more lysosomal enzyme deficiencies.

In certain embodiments, the method of the invention assays enzymatic activity of one or more lysosomal enzymes selected from:
  (a) α-glucosidase (GAA);
  (b) α-galactosidase (GLA);
  (c) α-L-iduronidase (IDUA);
  (d) β-glucocerebrosidase (ABG);
  (e) β-galactocerebrosidase (GALC);
  (f) sphingomyelinase (ASM);
  (g) iduronate 2-sufatase (ID2S);
  (h) N-acetylgalactosamine 6-sulfatase (GAL6S); and
  (i) N-acetylgalactosamine 4-sulfatase (GAL4S).

Any combination of the lysosomal enzymes noted above can be assayed by the method. In one embodiment, each of the lysosomal enzymes noted above is assayed simultaneously.

In certain embodiments, determining the quantities of the enzyme products comprises conducting the solution comprising the enzyme product to a mass spectrometer by liquid chromatography. In other embodiments, determining the quantities of the enzyme products comprises conducting the solution comprising the enzyme product to a mass spectrometer by flow injection.

In another aspect of the invention, an aqueous composition for assaying one or more lysosomal enzymes is provided. In one embodiment, the composition includes:

(a) one or more metal cations effective for precipitating sulfate ions;

(b) one or more metal cations effective for precipitating phosphate ions;

(c) a maltase glucoamylase inhibitor;

(d) a beta-N-acetylhexosaminidase inhibitor; and (e) one or more surfactants.

In certain embodiments, the composition further includes a buffer. Suitable buffers include phosphate, carboxylate, sulfate, sulfonate, and sulfate monoester buffers.

Suitable surfactants useful in the composition include cationic, anionic, neutral, and non-ionic surfactants.

Representative metal cations effective for binding sulfate ions include $Ba^{2+}$, $Hg^+$, $Pb^{2+}$, $Ra^{2+}$, $Sr^{2+}$, $Bi^{3+}$, $Cd^{2+}$, $Ca^{2+}$, and $Mg^{2+}$.

Representative metal cations effective for binding phosphate ions include $Ba^{2+}$, $Ce^{3+}$, $Hg^+$, $Pb^{2+}$, $Ra^{2+}$, $Sr^{2+}$, $Bi^{3+}$; $Cd^{2+}$, $Ca^{2+}$, and $Mg^{2+}$.

In one embodiment, the maltase glucoamylase inhibitor is acarbose.

In one embodiment, the beta-N-acetylhexosaminidase inhibitor is 2-acetamido-2-deoxy-D-glucono-1,5-lactone.

In certain embodiments, the composition further includes one or more substrates for a lysosomal enzyme. Representative substrates include substrates for a lysosomal enzyme selected from:

(a) α-glucosidase (GAA);
(b) α-galactosidase (GLA);
(c) α-L-iduronidase (IDUA);
(d) β-glucocerebrosidase (ABG);
(e) β-galactocerebrosidase (GALC);
(f) sphingomyelinase (ASM);
(g) iduronate 2-sufatase (ID2S);
(h) N-acetylgalactosamine 6-sulfatase (GAL6S); and
(i) N-acetylgalactosamine 4-sulfatase (GAL4S).

In certain embodiments, the composition includes a substrate for each of the enzymes noted above.

In certain embodiments, the compositions of the invention further include one or more internal standards for a lysosomal enzyme. Representative internal standards include internal standards for a lysosomal enzyme selected from:

(a) α-glucosidase (GAA);
(b) α-galactosidase (GLA);
(c) α-L-iduronidase (IDUA);
(d) β-glucocerebrosidase (ABG);
(e) β-galactocerebrosidase (GALC);
(f) sphingomyelinase (ASM);
(g) iduronate 2-sufatase (ID2S);
(h) N-acetylgalactosamine 6-sulfatase (GAL6S); and
(i) N-acetylgalactosamine 4-sulfatase (GAL4S).

In certain embodiments, the composition includes an internal standard for each of the enzymes noted above.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

FIGS. 5A-5C and 7A-7F are based on 80 samples, 58 non-affected and 22 affected patients. The 22 affected samples are composed of 3 patients for each of the disease except for GAL4S deficiency (n=1).

DETAILED DESCRIPTION OF THE INVENTION

Figure 1A:
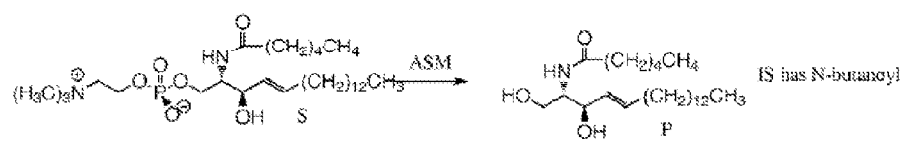
FIGS. 1A-1I illustrate the chemical structures of the nine substrates (S), products (P), and internal standards (IS) used to assay nine lysosomal enzymes.
Figure 1B:
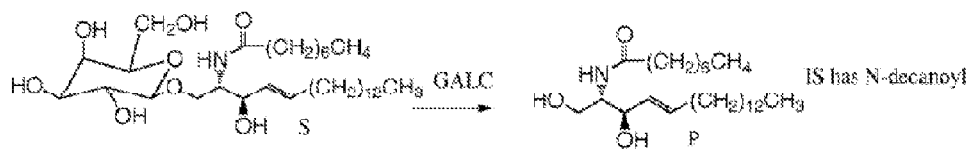
Figure 1C:
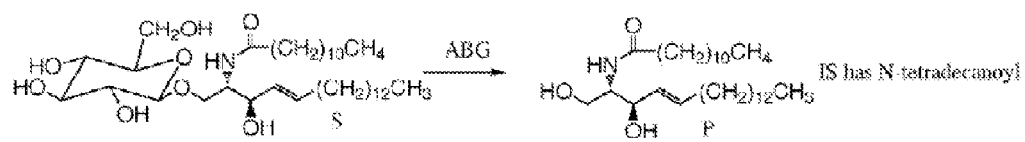
Figure 1D:
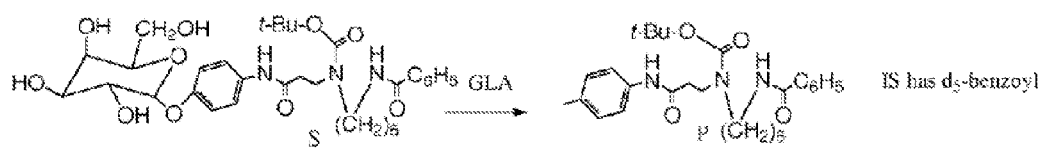
Figure 1E:
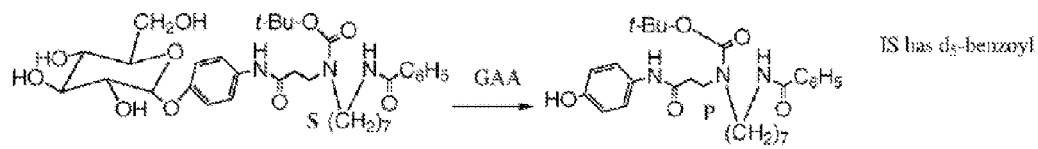
Figure 1F:
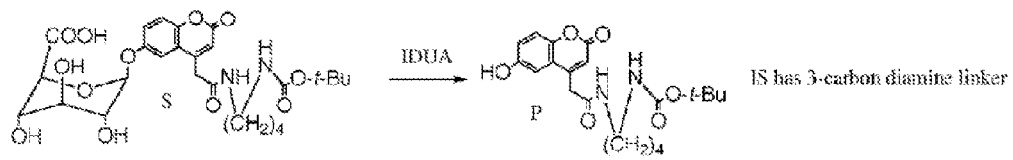
Figure 1G:
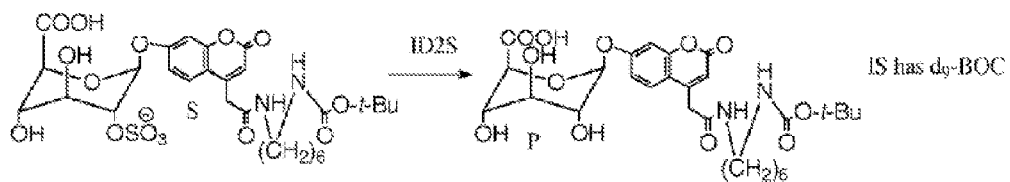
Figure 1H:
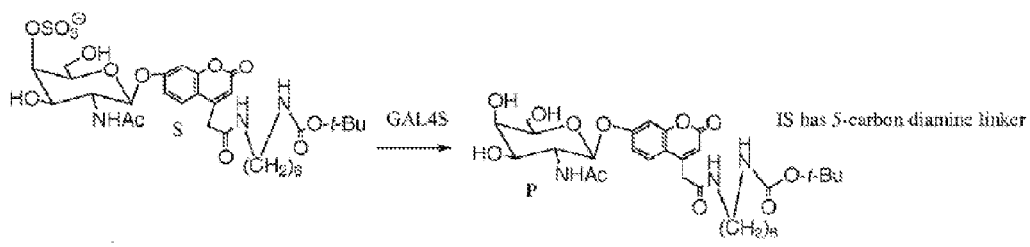
Figure 1I:
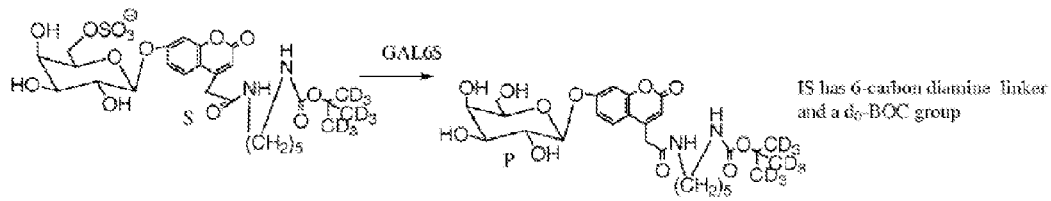

In one aspect, the present invention provides methods for assaying lysosomal enzymatic activity. In embodiments of the methods, the quantity of an enzyme product is determined by comparing a signal derived from the enzyme product to signal derived from a known quantity of an internal standard. The amount of the enzyme product is determined by the enzymatic activity of the enzyme on a substrate that is added to the sample to be assayed and the quantification of the enzyme product provides the measure of the enzymatic activity in the sample. The methods are useful for assaying lysosomal enzymatic activity in an individual (e.g., newborn) to evaluate whether the individual suffers from a deficiency of lysosomal enzymatic activity and is therefore a candidate for treatment.

In the methods of the invention, the enzymatic activity of a plurality of lysosomal enzymes is determined simultaneously in a multiplexed assay. In embodiments of the methods, one or more or all of nine (9) lysosomal enzymes are assayed using either one or two enzyme reaction buffer systems (e.g., six are assayed in a first enzyme reaction buffer and three are assayed in a second enzyme reaction buffer). The enzyme reaction buffers allow for multiplexed assays of the invention, which advantageously simplify lysosomal enzyme assay.

In another aspect, the invention provides reagents (e.g., enzymatic substrates, internal standards, and reaction buffers) for assaying lysosomal enzymatic activity in accordance with the methods.

Methods for Assaying Enzymatic Activity

In one aspect, the present invention provides methods for assaying the enzymatic activity of a plurality of lysosomal enzymes. In embodiments of the methods, the quantity of enzyme products is determined by comparing a signal derived from each enzyme product to signal derived from a known quantity of an enzyme internal standard. The amount of product is determined by the enzymatic activity of the enzymes on their respective substrates added to the sample to be assayed and the quantification of the enzyme products provides the measure of the enzymes' activities in the sample. The methods are useful for assaying enzymatic activity in individuals (e.g., newborns) to evaluate whether the individual suffers from a deficiency of enzymatic activity and is therefore a candidate for treatment for one or more of the diseases or syndromes associated with lysosomal enzyme deficiency.

In one embodiment of the method, the enzyme products and the internal standards differ in mass and the quantities of products is determined by mass spectrometry.

In certain embodiments of the methods, the products and internal standards are extracted from the aqueous enzyme reaction mixture containing the enzyme, excess substrates, the products, and the internal standards by liquid-liquid extraction using an organic solvent. In other embodiments, the aqueous enzyme reaction mixture noted above is applied to a suitable solid phase from which the products and internal standards are eluted. It will be appreciated that in certain embodiments, substrates will be extracted along with products and internal standards due their comparable solubilities. For embodiments that employ liquid chromatography for introduction of the sample to the mass spectrometer, the aqueous enzyme reaction mixture can be directly introduced into the liquid chromatograph which separates the substrate, product, and internal standards without the need of an extraction step. In these embodiments, the aqueous enzyme reaction solution can be quenched with an appropriate organic solvent (e.g., acetonitrile) to precipitate protein to preclude its loading onto the liquid chromatograph. For embodiments that employ flow injection for introduction of the sample to the mass spectrometer, liquid-liquid extraction or solid phase extraction can be utilized prior to flow injection. In certain embodiments that utilize flow injection, substrates (e.g., MPS-IVA and MPS-VI) can be trapped by ion exchange resin and substantially removed from the sample prior to flow injection.

In each method, quantification of the product is facilitated by quantifying the internal standard.

In one embodiment, the method for assaying enzymatic activities includes the following steps:

(a) contacting a dried blood sample with a first buffer solution to provide a solution comprising a plurality of lysosomal enzymes;

(b) adding an enzyme substrate for each lysosomal enzyme to be analyzed to the solution comprising the enzymes and incubating the substrates with the enzymes for a pre-determined time to provide a solution comprising an enzyme product for each lysosomal enzyme present in the sample (an internal standard for each lysosomal enzyme to be analyzed can be added to the solution at the same time as or after the addition of substrates, to ultimately provide a solution comprising the products and internal standards);

(c) optionally, quenching the enzyme reactions by, for example, adding a second buffer to the solution comprising the enzyme products; and (d) determining the quantities of the enzyme products.

In the methods of the invention, the enzyme reactions are optionally quenched prior to further processing. As used herein, the term "quenched" refers to stopping the enzyme reaction by, for example, changing the pH of the reaction solution or adding a solvent that precipitates protein (e.g., the enzymes) from the reaction solution.

As noted above, the products and internal standards can be separated from the enzyme for analysis by any one of a variety of techniques (e.g., liquid-liquid extraction, solid-liquid extraction, pelletization to provide supernatant).

In one embodiment, the dried blood sample is a dried blood spot from a individual (e.g., a newborn in which the dried blood spot is from a newborn screening card). However, the method can be performed on any sample that contains lysosomal enzymes including specimens (e.g., plasma, serum, tissue) from human, animal, and non-living sources. Blood samples other than dried blood are also suitable for assay by the method.

In the method, a sample containing one or more enzymes is contacted with a first buffer solution to provide a solution comprising the one or more enzymes. The step can be considered to be an extraction or hydration step in which at least a portion of the enzymes in the sample (e.g., dried blood spot) is extracted into an aqueous liquid phase so that enzymatic reaction can occur. The solution need not be homogeneous and need only provide an aqueous liquid phase sufficient for enzymatic reaction between the enzymes and the substrates.

In one embodiment, the first buffer is an aqueous buffer having pH sufficient to extract and dissolve the enzymes from the sample, as necessary, to provide an enzyme reaction mixture that provides enzyme products by incubation of the enzymes with the substrates. It will be appreciated that in certain embodiments, the sample can be added directly to an assay buffer that includes the substrates.

To assay enzymatic activity, substrates are incubated with the enzymes to provide products. In one embodiment, substrates are added to the enzyme solution and incubated for a time sufficient (e.g., a pre-determined time) to provide a solution comprising the products. The time can vary and will depend on the amount of enzymatic activity of the sample and the sensitivity of the analytical method for quantifying the enzyme products and internal standards. In one embodiment, incubating for time sufficient includes incubating the substrates with the enzymes at 37° C. for 20 hours. Pre-determined incubation times can range from less than one hour to more than 20 hours depending on the sample. In one embodiment, substrates are included in the assay buffer solution. After the pre-determined time, the enzyme reaction is optionally quenched (i.e., stopped) by the addition of a second buffer (e.g., 0.1 mol/L sodium acetate pH 5.4). The quenching buffer has a pH sufficient to stop the enzyme reaction. The pH of the enzyme reaction mixture is such that separation of the enzyme from the products and internal standards is achieved.

In certain embodiments of the invention, the quantity of enzyme product is determined by comparing the signal associated with the internal standard to the signal associated with the product. In one embodiment of the method, the internal standard is added prior to incubation with the enzyme (e.g., before, after, or simultaneously with the addition of the substrate). In another embodiment, the internal standard is added as a component of the buffer used to quench the enzyme reaction. In a further embodiment, the internal standard is added to the quenched enzyme reaction mixture that includes the product. In another embodiment, the internal standard can be added after sample workup and prior to mass analysis.

In the methods, the products and internal standards are separated from the aqueous enzyme reaction mixture (e.g., separated from the enzyme and certain excess substrates) for further analysis. In one embodiment, the aqueous enzyme reaction mixture is extracted with an organic solvent to provide an organic phase that includes the enzyme products and internal standards. Suitable organic solvents are substantially immiscible with water and are not effective in solubilizing the enzymes or enzyme substrates. Suitable organic solvents selectively and efficiently extract the product and internal standard, and extract each substantially equally (i.e., the enzyme products and internal standards have substantially the same partition coefficients for a given solvent). Suitable solvents include ethyl acetate, diethyl ether, chloroform, methylene chloride, and butanol. In one embodiment, the organic solvent is ethyl acetate. It will be appreciated that certain of the substrates are soluble in organic solvents used for product and internal standard extraction. In these instances and when the products and internal standards are quantified by mass spectrometry, the mass spectrometer can be tuned to select only product formed from the enzyme reaction rather than product formed from the electrospray ionization process. Furthermore, when liquid chromatography is used to introduce the sample to the mass spectrometer, substrate is separated from product during the chromatography thereby facilitating product quantitation. Additionally, when flow injection is used to introduce the sample to the mass spectrometer, certain substrates (e.g., MPS-IVA and MPS-VI) can be trapped by ion exchange resin and substantially removed from the sample prior to flow injection.

In another embodiment, the enzyme products are separated from the aqueous enzyme reaction mixture (including internal standards) by solid phase extraction. In this embodiment, the aqueous enzyme reaction mixture is applied to a suitable solid phase. Suitable solid phases are effective in selectively retaining and releasing the enzyme products and internal standards substantially equally. Representative solid phases include silica gel, reverse-phase silica (e.g., C18-silica), and ion exchange resins, such as anion exchange resins. The enzyme products and internal standards can then be eluted from the solid phase, either sequentially or simultaneously, with one or more suitable organic solvents and the resulting solution(s) analyzed as described herein. Suitable organic solvents elute the enzyme products and internal standards substantially completely from the solid phase. The products and internal standards can be eluted from the solid phase either separately or together. In one embodiment, the products and internal standards are eluted together.

Once the enzyme products and internal substrates have been isolated, the enzyme products are quantitated. In certain embodiments of the methods, the determination of the quantity of enzyme products is facilitated by the internal standards. Because the quantity of each internal standard is known, measuring a signal associated with the internal standard and comparing that signal to the signal associated with each enzyme product allows for the determination of the quantity of enzyme products. As noted above, the signal associated with the enzyme product and internal standard can be measured by mass spectrometry (e.g., tandem mass spectrometry).

In one embodiment, the quantities of enzyme products are determined by determining the ratio of the product to internal standards by tandem mass spectrometric analysis. In the MSMS method, parent ions of the products and internal standards are generated, isolated, and subjected to collision-induced dissociation to provide product fragment ions and internal standard fragment ions, respectively. Comparing the peak intensities of the product fragment ions and internal standard fragment ions allows for the calculation the amount of products.

In the methods of the invention, a known amount of each internal standard is added as described above to the enzymatic reaction system, which ultimately generates the products in the presence of the enzymes. In the tandem mass spectrometric methods of the invention, the peak area integrals for the enzyme product fragment ions and the internal standard fragment ions are measured and the ratio of the enzyme product peak area to the internal standard peak area is multiplied by the number of moles of internal standard added to provide the number of moles of enzyme product, thereby quantitating the enzyme product produced by the enzyme in the original sample.

The tandem mass spectrometric methods of the invention effectively quantify the products. The methods are effective when the parent mass of the product and internal standard are the same and their fragments are different, or the parent mass of the product and internal standard are different and the fragments are both the same or are both different.

The methods of the invention for assaying enzymatic activity depend on the measurement of signals from the products and internal standards. The enzyme product and internal standard are related in several ways. For the methods of the invention that rely on liquid-liquid extraction for isolation of the enzyme product from the aqueous enzyme reaction mixture, each is extractable into the organic extraction solvent substantially equally (ideally the same). For the methods of the invention that rely on mass spectrometric analysis, each produces a fragment ion having a mass that is different and that can be resolved from the other, and the product and internal fragment ions are produced from respective fragments having substantially the same ionization efficiency (ideally the same).

In one embodiment, the invention provides a method for assaying enzymatic activity that includes (a) incubating substrates with the enzymes to provide an enzyme reaction mixture containing the products; (b) optionally quenching the enzyme reaction; (c) adding internal standards to the enzyme reaction mixture; (d) separating the products and internal standards from the enzyme reaction mixture; and (e) quantifying the products.

In another embodiment, the invention provides a method for assaying enzymatic activity that includes (a) incubating substrates with the enzymes to provide an enzyme reaction mixture containing products; (b) optionally quenching the enzyme reaction with a buffer solution that includes the internal standards; (c) separating the products and internal standards from the enzyme reaction mixture; and (d) quantifying the products.

In a further embodiment, the invention provides a method for assaying enzymatic activity that includes (a) incubating substrates with the enzymes in the presence of internal standards to provide an enzyme reaction mixture containing products; (b) optionally quenching the enzyme reaction; (c) separating the products and internal standards from the enzyme reaction mixture; and (d) quantifying the products.

In certain embodiments, in the methods of the invention determining the quantities of the enzyme products comprises determining the ratio of each product to its internal standard by mass spectrometric analysis. Suitable mass spectrometric analysis includes tandem mass spectrometric analysis (i.e., MSMS) using tandem mass spectrometers. For embodiments, the utilize MSMS, determining the quantities of the products includes tandem mass spectrometric analysis in which the parent ions of the products and their internal standards are generated, isolated, and subjected to collision-induced dissociation to provide product fragment ions and internal standard fragment ions. Determining the quantities of the products includes comparing the peak intensities of the product fragment ions and internal standard fragment ions to calculate the amount of the products.

In one embodiment, the methods of the invention further include using the quantities of the products to determine whether the dried blood sample is from a candidate for treatment for a condition associated with one or more lysosomal enzyme deficiencies.

In the methods of the invention that utilize mass spectrometric analysis, the sample to be analyzed (e.g., solution containing the enzyme products and internal standards) can be introduced to the mass spectrometer by methods known in the art. In one embodiment, determining the quantities of the enzyme products comprises conducting the solution comprising the enzyme product to a mass spectrometer by liquid chromatography (LC). In another embodiment, determining the quantities of the enzyme products comprises conducting the solution comprising the enzyme product to a mass spectrometer by flow injection (FI). LC and FI methods and the results for those methods are described below.

Through the use of novel enzyme reaction buffers, in one embodiment the present invention provides for multiplex enzyme assay of nine (9) lysosomal enzymes. In another embodiment, the invention provides a multiplex enzyme assay of six (6) lysosomal enzymes. In a further embodiment, the invention provides a multiplex enzyme assay of three (3) lysosomal enzymes.

Substrates and Internal Standards

Representative enzyme substrates, internal standards, and mass spectrometric methods for assaying lysosomal enzymes useful in the present invention are described in U.S. patent application Ser. No. 12/706,794 (U.S. Patent Application Publication No. U.S. 2010/0209951 A1), filed Feb. 17, 2010, and PCT/US2011/049224, filed Aug. 25, 2011, each expressly incorporated herein by reference in its entirety.

Figure 9A:
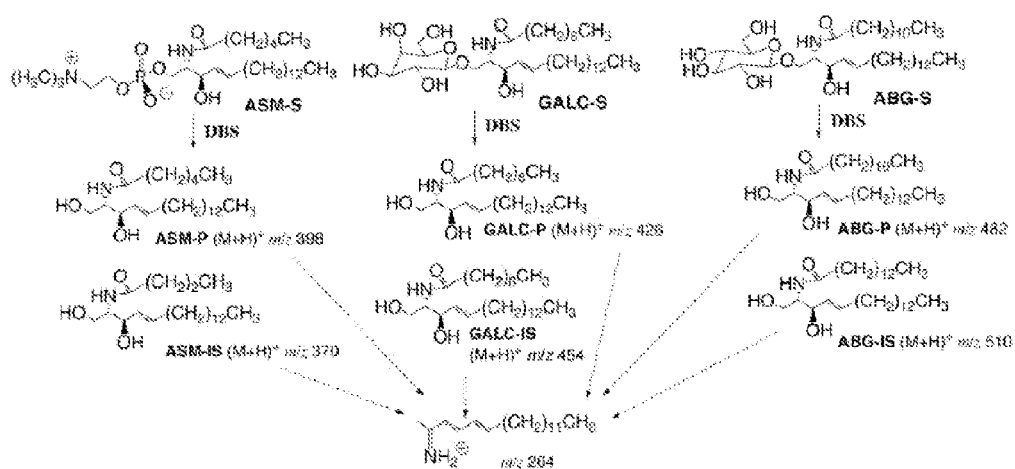
FIG. 9A illustrates representative substrates (S) useful in the assay of the invention for detecting enzymes relevant to Niemann-Pick Type-A/B (left), Krabbe (middle) and Gaucher (right) diseases. Enzymatic products (P) from these substrates and representative internal standards (IS) useful for quantification are also shown. Fragment ions that result from collision-induced dissociation of the parent ions in the mass spectrometer are also shown.
Figure 9B:
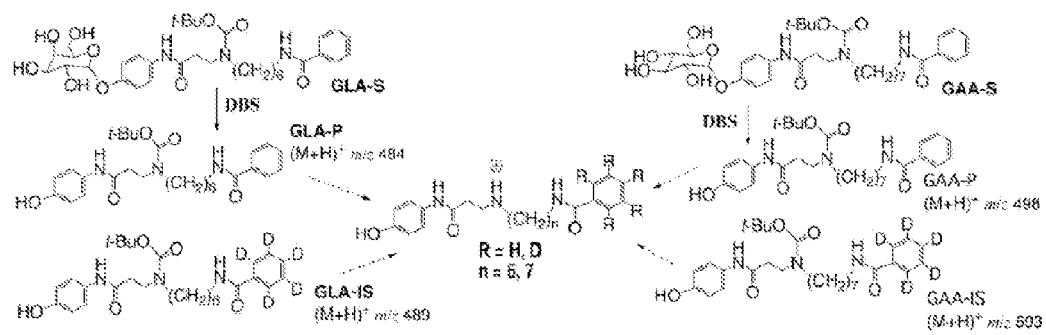
FIG. 9B illustrates representative substrates (S) and internal standards (IS) useful in the assay of the invention for detecting enzymes relevant to Fabry (left) and Pompe (right) diseases. Fragment ions that result from collision-induced dissociation of the parent ions in the mass spectrometer are also shown.
Figure 10:
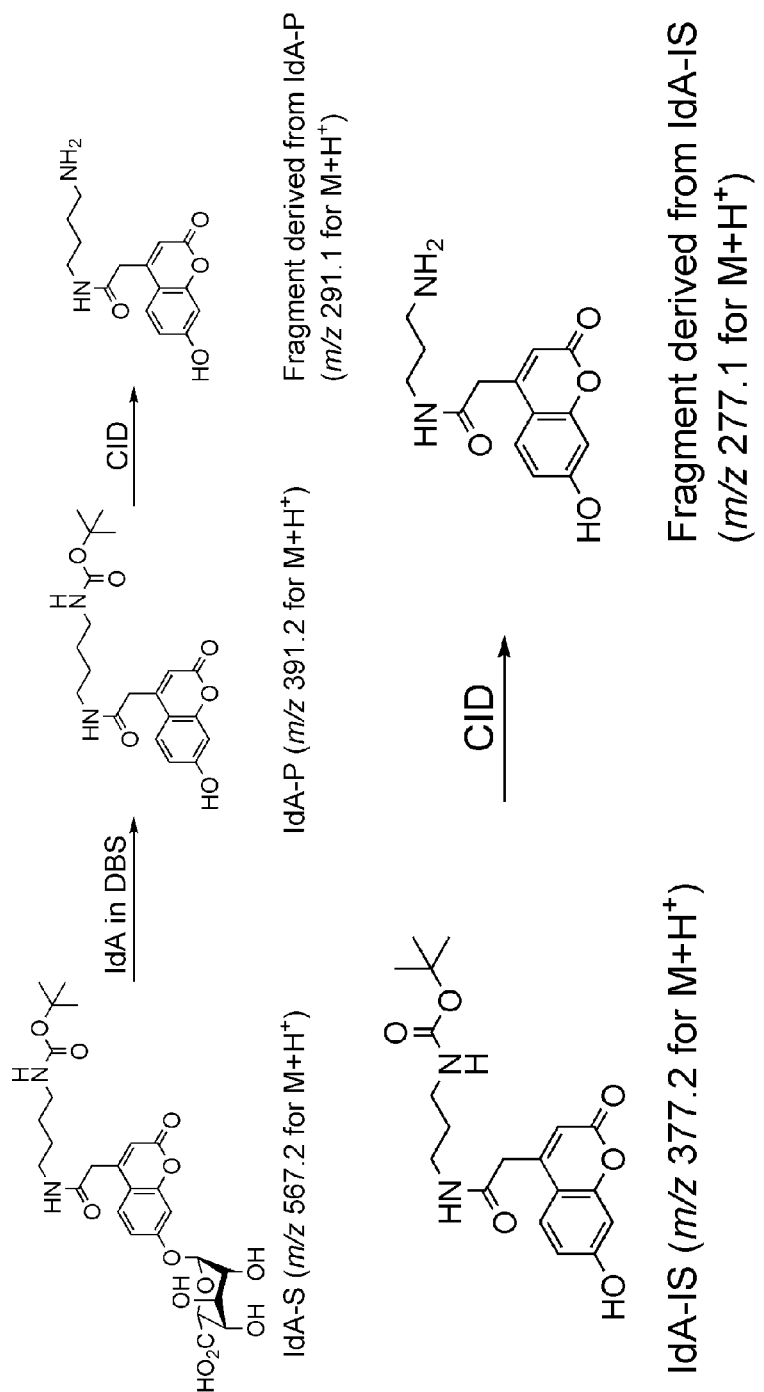
FIG. 10 illustrates a representative substrate (S) and internal standard (IS) useful in the assay of the invention for detecting enzymes relevant to Mucopolysaccharidosis Type I. The enzyme product (P) and fragment ions that result from collision-induced dissociation of the parent ions in the mass spectrometer are also shown.
Figure 11:
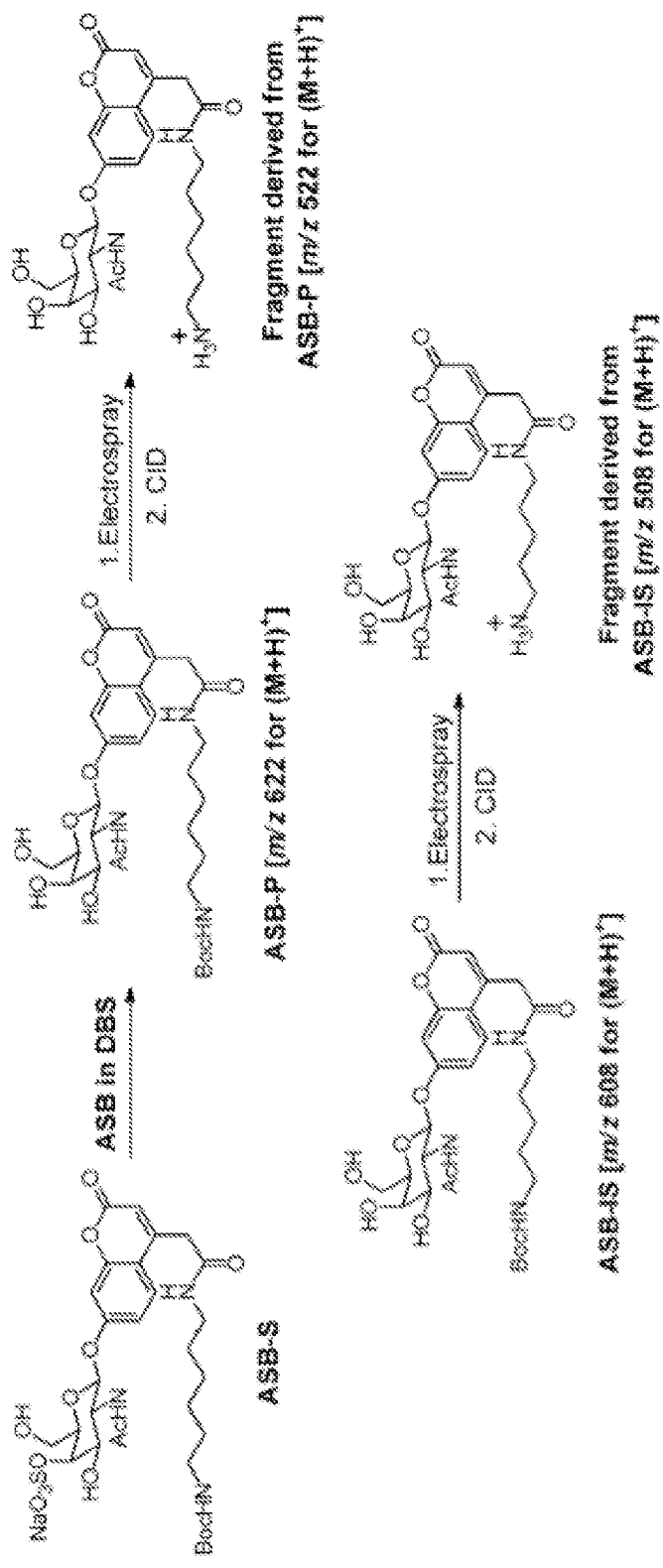
FIG. 11 illustrates a representative substrate (S) and internal standard (IS) useful in the assay of the invention for detecting enzymes relevant to Mucopolysaccharidosis Type VI. The enzyme product (P) and fragment ions that result from collision-induced dissociation of the parent ions in the mass spectrometer are also shown.
Figure 12:
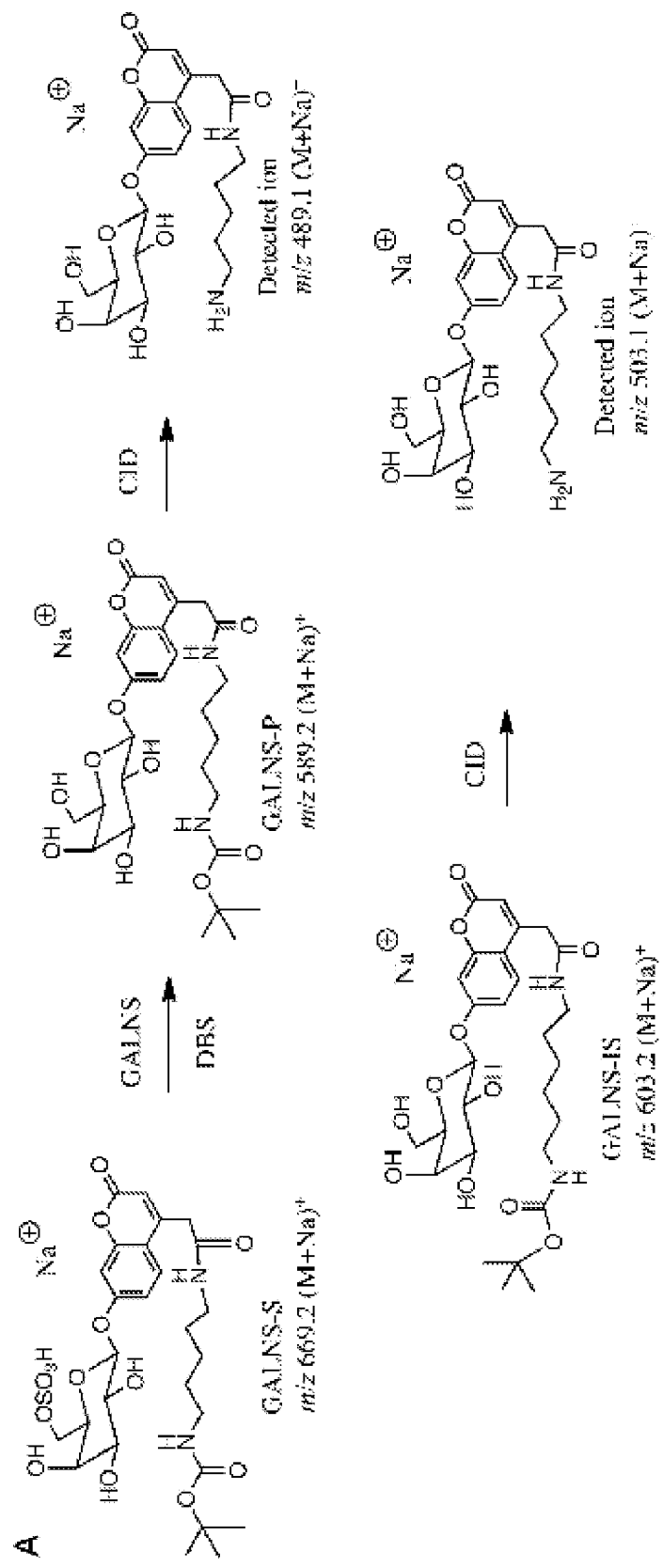
FIG. 12 illustrates a representative substrate (S) and internal standard (IS) useful in the assay of the invention for detecting enzymes relevant to Mucopolysaccharidosis Type IVA. The enzyme product (P) and fragment ions that result from collision-induced dissociation of the parent ions in the mass spectrometer are also shown.
Figure 13:
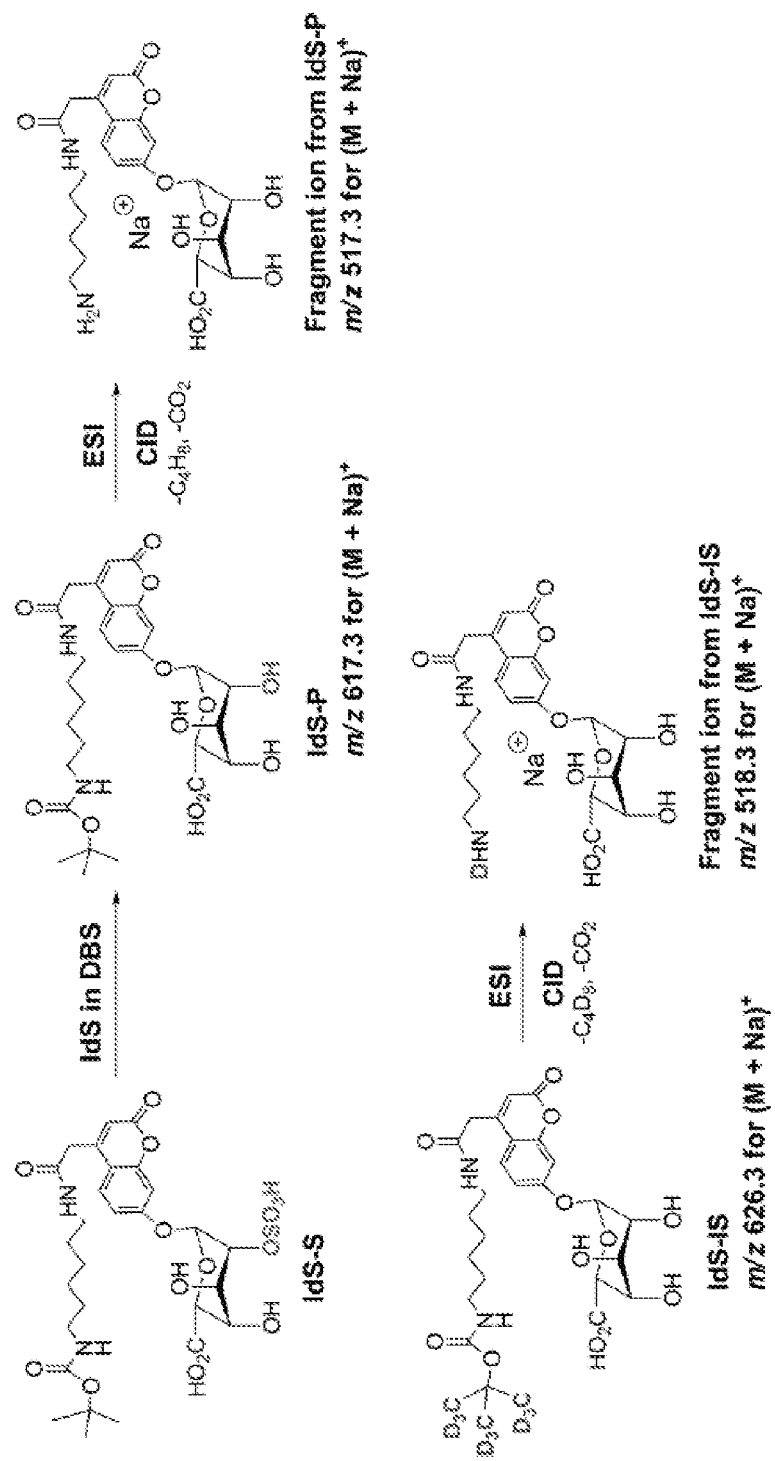
FIG. 13 illustrates a representative substrate (S) and internal standard (IS) useful in the assay of the invention for detecting enzymes relevant to Mucopolysaccharidosis Type II. The enzyme product (P) and fragment ions that result from collision-induced dissociation of the parent ions in the mass spectrometer are also shown.

FIGS. 1A-1I illustrate the chemical structures of the nine substrates (S), products (P), and internal standards (IS) for the assay of nine lysosomal enzymes. Representative substrates (S) useful in the assay of the invention for detecting enzymes relevant to Niemann-Pick Type-A/B (left), Krabbe (middle) and Gaucher (right) diseases are illustrated in FIG. 9A. FIG. 9B illustrates representative substrates (S) and internal standards (IS) useful in the assay of the invention for detecting enzymes relevant to Fabry (left) and Pompe (right) diseases. Representative substrates and internal standards useful in the assays of the invention for detecting enzymes relevant to Mucopolysaccharidosis Type I, Mucopolysaccharidosis Type VI, Mucopolysaccharidosis Type IVA, and Mucopolysaccharidosis Type II are illustrated in FIGS. 10-13, respectively.

Compositions for Enzyme Reaction Solutions

In the methods of the invention, the enzyme reactions are performed in solution conducive for multiplexed enzymatic reactions. In one embodiment, the enzyme reaction solutions includes (a) one or more metal cations effective for precipitating sulfate ions;

(b) one or more metal cations effective for precipitating phosphate ions;

(c) a maltase glucoamylase inhibitor;

(d) a beta-N-acetylhexosaminidase inhibitor; and (e) one or more surfactants.

The one or more metals cations of the solution are effective for binding or precipitating sulfate and phosphate ions that are present in blood and that would interfere with the assay of the lysosomal sulfatases. Sulfate and phosphate can inhibit sulfatase activity. Suitable metal cations include any metal ion effective for precipitating or binding to and otherwise rendering sulfate and phosphate unavailable for interference with the assay of sulfatase activity. Representative metal ions include $Ba^{2+}$, $Ce^{3+}$, $Hg^+$, $Pb^{2+}$, $Ra^{2+}$, $Sr^{2+}$, $Bi^{3+}$, $Cd^{2+}$, $Ca^{2+}$, and $Mg^{2+}$. Mixtures of metal ions can be used. Representative suitable counterions include chloride, bromide, iodide, and fluoride; organic carboxylates such as formate and acetate; nitrate; cyanide; sulfide, hydroxide, oxide, thiocyanate, thiolate ($RS^-$, e.g., where R is C1-C20 alkyl or C6-C20 aryl), and alcholate ($RO^-$, e.g., where R is C1-C20 alkyl or C6-C20 aryl). In one embodiment, the one or more metal ions effective to precipitate or otherwise bind to and remove sulfate and phosphate are $Ba^{2+}$ (e.g., acetate) for sulfate precipitation and $Ce^{3+}$ (e.g., acetate) for phosphate removal. In certain embodiments, the metal cations effective for precipitating sulfate and phosphate ions are present at a concentration from about 0.01 to about 20 mM. In certain embodiments, the metal cations are present from about 5 to about 10 mM. In one embodiment, the metal cation (e.g., $Ba^{2+}$) effective for precipitating sulfate ions is present at 7.5 mM. In one embodiment, the metal cation (e.g., $Ce^{3+}$) effective for precipitating phosphate ions is present at 5.5 mM.

The solution includes an inhibitor of maltase glucoamylase (EC 3.2.1.3). Maltase glucoamylase is present on some blood cells in dried blood spots and can hydrolyze the Pompe (GAA) substrate. Suitable maltase glucoamylase inhibitors include those known in the art. A representative maltase glucoamylase inhibitor is acarbose. It will be appreciated that acarbose derivatives and analogs as well as other aunts effective in blocking the activity of maltase glucoamylase is an inhibitor of maltase glucoamylase for the purpose of the enzyme reaction solution. In certain embodiments, the maltase glucoamylase inhibitor is present at a concentration from about 1 to about 50 μM. In other embodiments, the inhibitor is present from about 5 to about 20 μM. In one embodiment, the inhibitor (e.g., acarbose) is present at about 8

The solution also includes an inhibitor of beta-N-acetylhexosaminidase (EC 3.2.1.52). Beta-N-acetylhexosaminidase is present on some blood cells in dried blood spots and can hydrolyze the MPS-VIA product and internal standard. Suitable beta-N-acetylhexosaminidase inhibitors include those are known in the art. A representative beta-N-acetylhexosaminidase inhibitor is 2-acetamido-2-deoxy-D-glucono-1,5-lactone. In certain embodiments, the beta-N-acetylhexosaminidase inhibitor is present at a concentration from about 10 to about 500 μM. In other embodiments, the inhibitor is present from about 50 to about 200 μM. In one embodiment, the inhibitor (e.g., 2-acetamido-2-deoxy-D-glucono-1,5-lactone) is present at about 150

The solution includes one or more surfactants. As used herein, the term "surfactant" is used interchangeably with the term "detergent." Suitable surfactants include cationic, anionic, neutral (e.g., zwitterionic and mixed charge), and non-ionic (i.e., no charged groups) surfactants. Representative surfactants include the following materials: 1-octanesulfonic acid sodium salt, 2-cyclohexylethyl-4-O-(alpha-D-glucopyranosyl)-b-D-glucopyranoside, 4-n-octylbenzoylamido-propyl-dimethylammonio-sulfobetaine, 4-oxo-3-(tetrahydro-furan-2-ylmethyl)-10-oxa-3-aza-tricyclo[5.2.1.0*1.5*]dec-8-ene-6-carboxylic acid, 6-cyclohexylhexyl-4-O-(alpha-D-alucopyranosyl)-beta-D-glucopyranoside, ASB-16, ASB-C7BzO, benzethonium hydroxide, Big CHAP, Brij 35, Bt3(1,3,5)IP3/AM, C12E8, CHAPSO, chenodeoxycholic acid (sodium salt), choline p-toluenesulfonate salt, cyclohexyl-n-hexyl-D-maltoside, cyclohexylmethyl-4-O-(a-D-glucopyranosyl)-b-D-glucopyranoside, DDMAB, decyl beta-D-maltopyranoside, decyl beta-D-thioglucopyranoside, decyl-beta-D-1-thiomaltopyranoside, diethylene glycol monohexyl ether, diethylene glycol monopentyl ether, digitonin, digitoxigenin, dimethylethylammoniumpropane sulfonate, eicosyltriethylammonium bromide, ELUGENT, ethylene glycol monodecyl ether, ethylene glycol monododecyl ether, ethylene glycol monohexadecyl ether, ethylene glycol monohexyl ether, ethylhexadecyldimethylammonium bromide, GENAPOL X-080, GENAPOL X-100, Glucopone 600, glycocholic acid (sodium salt), glycodeoxycholic acid (sodium salt), hexadecyltrimethylammonium p-toluenesulfonate, hexaethylene glycol monodecyl ether, hexaethylene glycol monododecyl ether, IGEPAL CA-630, lauroyl-DL-carnitine chloride, lauroylsarcosine (sodium salt), LPD-12, MEGA-8, MEGA-9, methoxypolyethylene glycol 350, methylbenzethonium chloride, N-decanoyl-N-methylglucamine, n-dodecyl alpha-D-maltoside, n-dodecyl-beta-D-maltoside, n-dodecyl-beta-D-glucopyranoside, n-heptyl-beta-D-glucopyranoside, n-hexadecyl-beta-D-maltoside, n-hexyl-beta-D-glucopyranoside, n-nonyl-beta-D-glucopyranoside, N-octanoyl-beta-D-glucosylamine, n-octanoylsucrose, n-octyl-beta-D-glucopyranoside, n-octyl-oligo-oxyethylene, n-octyl-beta-D-maltopyranoside, n-octyl-beta-D-thioglucopyranoside, n-octylglucoside, n-undecyl beta-D-glucopyranoside, N,N-dimethyloctadecylamine N-oxide, NDSB-195, NDSB-211, NDSB-221, NDSB-256, sodium tetradecyl sulfate, NDSB-256-4T, nonaethylene glycol monododecyl ether, Nonidet® P40, nonyl-beta-D-1-thiomaltoside, nonylphenyl-polyethyleneglycol acetate, octaethylene glycol monodecyl ether, octaethylene glycol monooctadecyl ether, octylthiogalactoside, oxyphenonium bromide, pentaethylene glycol monodecyl ether, pentaethylene glycol monooctyl ether, PLURONIC F-127, Polyoxyethylene (25) propylene glycol stearate, polyoxyethylenesorbitan monopalmitate, Polysorbate 60, Polysorbate 80, Saponin, sodium 1-heptanesulfonate, sodium taurodeoxycholate hydrate, sodium taurohyodeoxycholate hydrate, sorbitan monolaurate, sorbitan monostearate, sorbitan monooleate, sorbitane trioleate, sucrose monocaprate, sucrose monolaurate, saurochenodeoxycholic acid (sodium salt), taurodeoxycholic acid (sodium salt), tauroursodeoxycholic acid (sodium salt), Tergitol®, Tergitol®, NP-10, tetraethylene glycol monododecyl ether, tetraethylene glycol monohexadecyl ether, tetraethylene glycol monooctyl ether, NP-40, Triton X-100, Triton X-113, sodium cholate, sodium deoxycholate, CHAPS, Tween 85, Zwittergent 3-08, Zwittergent 3-10, Zwittergent 3-12, Zwittergent 3-14, Zwittergent 3-16, tris dodecyl sulfate, triethylene glycol monooctyl ether, triethylene glycol monodecyl ether, thonzonium bromide, APO-10, APO-12, APO-14, APO-16, ASB-14, and ASB-16. In one embodiment, the surfactant is sodium taurocholate. In certain embodiments, the surfactant is present at a concentration from about 2 to about 20 g/L. In other embodiments, the surfactant is present from about 5 to 15 g/L. In one embodiment, the surfactants (e.g., sodium taurocholate) is present at about 10 g/L.

The enzyme reaction solution is a buffered solution. Suitable buffers includes phosphate with suitable cations as counterions (e.g., $Li^+$, $Na^+$, $K^+$, $Rb^+$, $Cs^+$, $Be^{2+}$, $Ba^{2+}$, $Mg^{2+}$, $Sr^{2+}$, $NH_4^+$, $NR_4^+$, $NHR_3^+$, $NH_2R_2^+$, $NH_3R^+$ (where R is any carbon containing moiety compound of MW 1000 or less), pyridinium and any pyridinium bearing one or more additional R groups defined as above, imidazolium and imidazolium bearing one or more R groups defined as above, hydroxylammonium ($NH_3OH^+$) and $NH_2ROH^+$, $NHR_2OH^+$, and $NR_3OH^+$, phosphonium ($R_4P^+$), and pyrimidinium and pyrimidinium bearing one or more R groups defined as above. Other suitable buffers include carboxylates with suitable cations as counterions as noted above. Suitable carboxylates include any carbon containing compound of MW 1000 or less containing one or more carboxylate groups (e.g., formate, acetate, propionate, butyrate, isobutyrate, citrate, succinate, malonate, oxalate, and cacodylate). In addition to phosphates and carboxylates, other suitable buffers include sulfate, sulfonates ($RSO_3^-$, where R is defined as above), sulfate monoesters ($ROSO_3^-$, where R is defined as above) with suitable cations as counterions as noted above. Other suitable counterions include fluoride, thiocyanate, sulfite, and nitrite. In one embodiment, the buffer is a volatile buffer. In one embodiment, the buffer is an ammonium formate buffer.

In certain embodiments, the buffer is present at a concentration from about 0.05 to about 1.0 M. In one embodiment, the buffer (e.g., ammonium formate) is present from about 0.1 to about 0.5 M. The enzyme reaction solution generally has a pH from about 2 to about 9. In certain embodiments, the solution has a pH from about 3 to about 7. In other embodiments, the solution has a pH from about 4 to about 5.

In one particular embodiment, the 9-plex enzyme reaction solution is an ammonium formate buffered solution (0.5 M, pH 5.0) that includes barium (II) acetate (7.5 mM), cerium (III) acetate (5.0 mM), acarbose (8 μM), 2-acetamido-2-deoxy-D-glucono-1,5-lactone (150 μM), and sodium taurocholate (10 g/L).

In one particular embodiment, the 6-plex enzyme reaction solution is an ammonium formate buffered solution (0.1 M, pH 4.4) that includes acarbose (8 μM) and sodium taurocholate (10 g/L).

In one particular embodiment, the 3-plex enzyme reaction solution is an ammonium formate buffered solution (0.5 M, pH 5.0) that includes barium (II) acetate (7.5 mM), cerium (III) acetate (5.0 mM), 2-acetamido-2-deoxy-D-glucono-1, 5-lactone (150 μM), and sodium taurocholate (10 g/L).

In certain embodiments, the enzyme reaction solutions described above further include one or more substrates for a lysosomal enzyme. Representative substrates include lysosomal enzyme substrates for the following enzymes:

(a) α-glucosidase (GAA);
(b) α-galactosidase (GLA);
(c) α-L-iduronidase (IDUA);
(d) β-glucocerebrosidase (ABG);
(e) β-galactocerebrosidase (GALC);
(f) sphingomyelinase (ASM);
(g) iduronate 2-sufatase (ID2S);
(h) N-acetylgalactosamine 6-sulfatase (GAL6S); and
(i) N-acetylgalactosamine 4-sulfatase (GAL4S).

In certain embodiments, the enzyme reaction solution includes each of the substrates noted above. Representative substrates include those described herein.

In other embodiments, the enzyme reaction solutions described above include one or more internal standards for a lysosomal enzyme. Representative internal standards include lysosomal enzyme internal standards for the enzymes noted above. Representative internal standards include those described herein.

Nine-Plex (9-Plex) Assay (ASM, GAA, GLA, ABG, GALC, IDUA, ID2S, GAL6S, GAL4S)

In one embodiment, the invention provides a multiplex enzyme assay of nine (9) lysosomal enzymes using a first enzyme reaction buffer. Nine lysosomal enzymes are assayed in the 9-plex assay:

(1) acid sphingomyelinase (ASM, Niemann-Pick-A/B disease);
(2) α-acid-glucosidase (GAA, Pompe disease);
(3) α-galactosidase A (GLA, Fabry disease);
(4) acid α-glucocerebrosidase (ABG, Gaucher disease);
(5) galactocerebrosidase (GALC, Krabbe disease);
(6) α-iduronidase (IDUA, mucopolysaccharidosis-I);
(7) iduronate-2-sulfatase (ID2S, mucopolysaccharidosis-II);
(8) N-acetyl-galactosamine-6-sulfatase (GAL6S, mucopolysaccharidosis-IVA, Morquio A syndrome); and
(9) N-acetyl-galactosamine-4-sulfatase (GAL4S, mucopolysaccharidosis-VI, Maroteaux-Lamy syndrome).

The 9-plex enzyme reaction buffer includes:
(a) one or more metal cations effective for precipitating sulfate ions;
(b) one or more metal cations effective for precipitating phosphate ions;
(c) a maltase glucoamylase inhibitor;
(d) a beta-N-acetylhexosaminidase inhibitor; and
(e) one or more surfactants.

A representative method of the invention for multiplex analysis method of lysosomal enzymes can be summarized as follows. A DBS punch is incubated in an assay buffer containing synthetic substrates (S). To reduce the number of parallel incubations, a minimal number of assay buffers are used. After incubation to allow substrate to product conversion, the product (P) is quantified by tandem mass spectrometry. Internal standards (IS) are either chemically identical to the product but carrying a heavy isotope, or non-isotopic but closely related in structure. A tandem quadrupole mass spectrometer is used to detect a reporter ion derived from collision-induced dissociation of the precursor ion (MS/MS). This ensures analytical selectivity even though the highly complex mixture of whole blood is used. Both the product and internal standard reporter ions are detected by MS/MS for each of the 9 P/IS pairs. Use of an internal standard accounts for any loss of enzyme-generated product during the entire procedure (e.g., due to enzymatic decomposition of the product, loss of product due to binding to surfaces). The MS/MS detects one reporter ion at a time, but a rapid duty cycle is used to cover all 18 analytes (9 P/IS pairs) over a short time scale (about 100 msec).

The common structural features of the substrates are a group that is specifically recognized by the enzyme, a hydrophobic carbon chain as part of the enzyme-generated product (to allow interaction with the reverse-phase LC column to permit chromatographic separation), and a readily fragmentable functional group that directs ion collision induced dissociation along a dominant fragmentation pathway in the mass spectrometer (this improves assay sensitivity) (see FIGS. 1A-1I). t-Butyl-containing carbamates provide a readily fragmentable group (loss of $CO_2$ and isobutylene) in the case of GLA, GAA, IDUA, ID2S, GAL6S, and GAL4S products. For ABG, ASM and GALC, the ceramide readily fragments to give a common imminium ion containing the sphingosine moiety. The GAL6S substrate is unique in having a $d_9$-t-butyl group because the non-deuterated version is isobaric with IDUA substrate. An alternative approach of increasing the carbon chain of the linker to more than 5 carbons leads to a drop in aqueous solubility in the assay mixture. The additional cost of the deuterated reagents does not add significantly to the overall cost of reagent synthesis.

Considerable effort resulted in the assay buffers of the invention. The LC-MS/MS assay is sufficiently sensitive such that some of the enzymes can be assayed at a pH shifted from their pH optimum, thus minimizing the number of buffers needed. Detergent is required to solubilize ceramide-containing substrates, and detergent was well tolerated by the other lysosomal enzymes that act on water-soluble substrates. Acarbose has been reported to inhibit maltase glucoamylase, an enzyme in blood that has α-glucosidase activity in the acid pH range and thus interferes with the analysis of GAA. The sulfatases ID2S, GAL6S and GAL4S are inhibited by the relatively high concentrations of free sulfate and phosphate in blood, and the buffer contains metal cations that cause precipitation of these anions without reducing the activity of the non-sulfatases. In this way, the invention provides an assay for the 9 lysosomal enzymes either in two buffers (3-plex+6-plex) or in a single buffer (9-Alex). The former utilizes two punches of a DBS, whereas the latter only requires a single punch.

The assay requires a minimum number of liquid transfers. Using a multichannel pipettor, the complete assay cocktail is added to each well to cover the DBS punch. The plate is sealed with plastic film and placed in an orbital shaker/incubator for the desired incubation time. Acetonitrile is added to precipitate protein, and the plate is spun in a benchtop centrifuge to pellet the protein. Most of the supernatant is transferred to a new microtiter plate with a pipettor, water is added to dilute solvent strength, and the plate is sealed with aluminum foil and placed in the autosampler of the LC-MS/MS instrument. The assay thus requires a total of four liquid transfers, all are easily accomplished with an 8- or 96-channel handheld pipettor (automation is also possible if more than a few plates need to be processed).

UHPLC provides an automated and fast way to process the samples, thus eliminating the need for liquid-liquid and solid-phase extraction steps used in our earlier assays. By using two UHPLC columns and switching valves, one column is used to perform the analyte separation while the other column is being equilibrated with solvent for the next sample injection. This protocol doubles the throughput.

Figure 2:
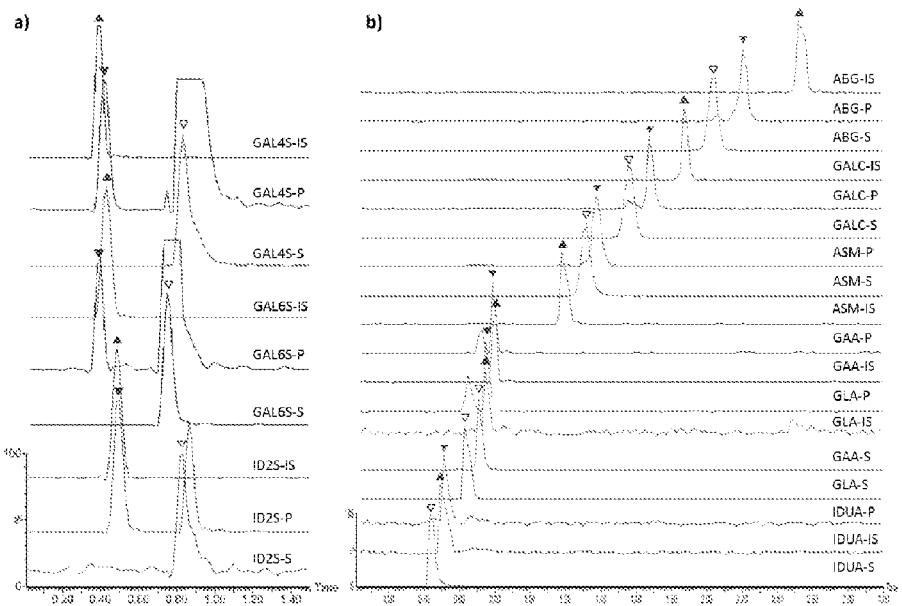
FIGS. 2A and 2B are HPLC-MS/MS chromatograms of 3-plex (2A) and 6-plex (2B) assay of a healthy control (each SRM channel represents S, product or internal standard. The down-pointing solid and open triangle denote the chromatographic peak of product (P) and substrate (S), respectively, and up-pointing solid triangle denotes the peak of internal standard (IS).
Figure 3:
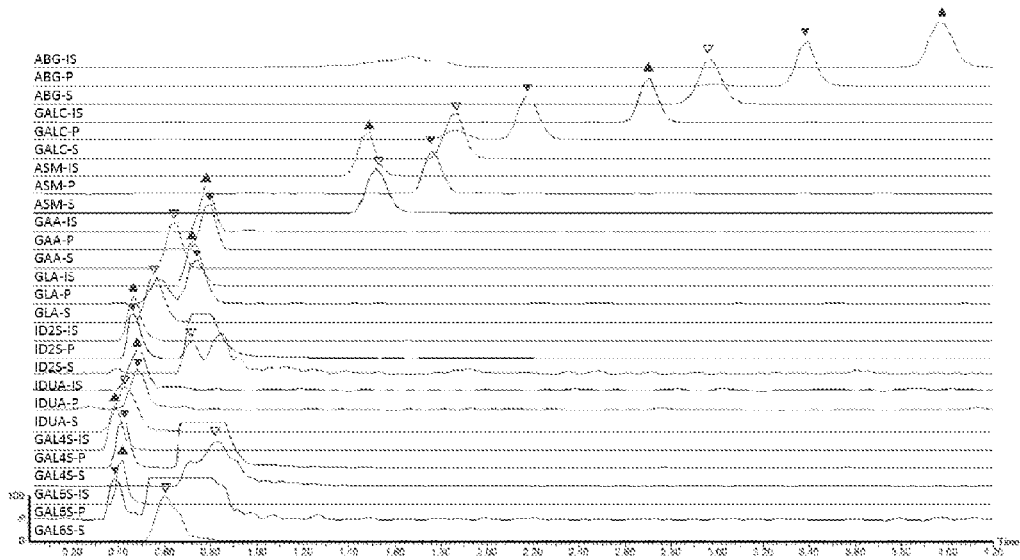
FIG. 3 is an HPLC-MS/MS chromatogram of combined 9-plex assay of a healthy individual.

A version of the multiplex assay in which the three sulfatases were incubated in a single buffer (3-plex) and the six other enzymes were assayed in a different buffer (6-plex) was thus requiring two 3 mm DBS punches was evaluated. FIGS. 2A and 2B show the HPLC ion traces for the 3-plex and 6-plex, respectively. For the 3-plex the products and internal standards elute well before the corresponding substrates. Chromatographic separation of substrate and product is important for the sulfatases because the substrates undergo some breakdown to products in the source of the mass spectrometer. It is desirable to quantify only the enzyme generated products corresponding to the ion reactions occurring at the UHPLC retention times of the products. The retention time of the ID2S product and internal standard are identical because the internal standard is the deuterated analog of the product. In the case of GAL4S and GAL6S, there is a slight retention time shift for product versus internal standard because the number of methylenes in the linker arms differ by one (compare FIGS. 1H and 1I). FIG. 2B compares the ion traces for the 6-plex. A small amount of substrate to product conversion due to in-source fragmentation is seen for ABG, GALC, GLA and GAA. A multiplex assay was evaluated in which product and internal standard from assay incubations for the 3-plex and 6-plex reactions were combined and submitted to a single HPLC-MS/MS analysis (FIG. 3). Chromatographic separation of substrate and product is achieved in all 9 cases. These HPLC runs require up to 4 min.

Figure 4:
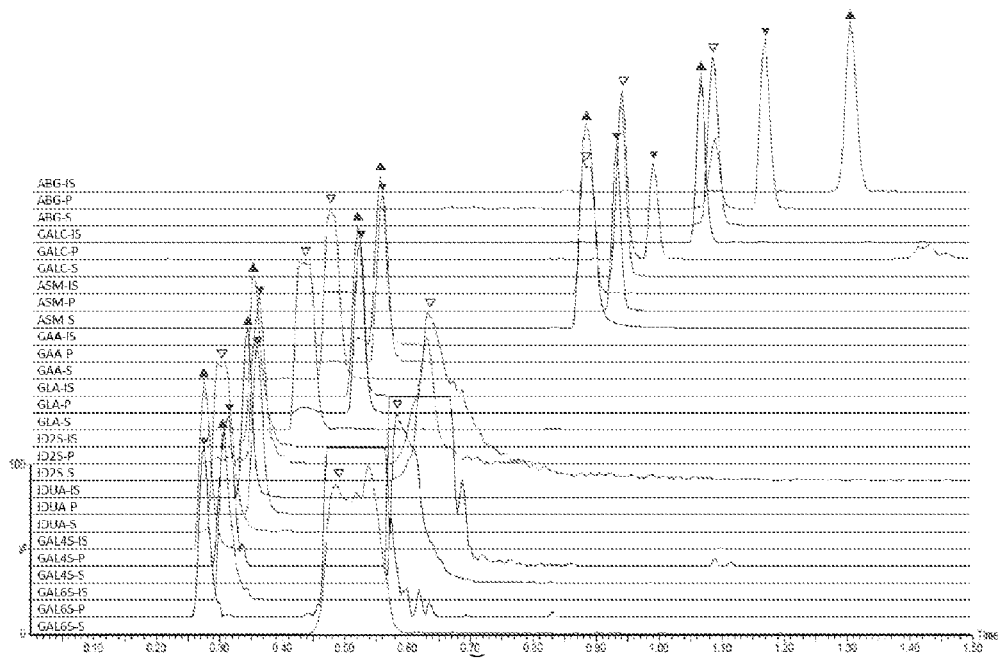
FIG. 4 is an UHPLC-MS/MS chromatogram of combined 9-plex assay of a healthy individual.

A substantial improvement of separation speed was achieved by UHPLC, and the results are shown in FIG. 4. In-source fragmentation of substrate to product is seen in the case of ABG, GALC, GAL4S, GAL6S, and to a lower extent for GLA and GAA. Analytes were well resolved in only 1.4 min and the separation between substrate and product was superior to that obtained in HPLC for all analytes. This robust separation using UHPLC ensures that there is no contamination of the product peaks from in-source fragmentation of the substrates. By use of dual columns with switching valves, an inject-to-inject time of only 1.8 min was achieved.

The 6+3-plex and 9-plex assays were evaluated on the quality control samples. The Centers for Disease Control and Prevention (CDC) distributes blood spots made from leukocyte depleted blood (base pool) mixed with various amounts of unprocessed cord blood (pooled from many donors). As shown in FIGS. 6A-6I, highly linear responses were obtained for all 9 enzymes (specific activity of each enzyme in μmol product $hr^{-1}$ (L blood)$^{-1}$ versus the fraction of whole blood in the CDC quality control DBS) showing that the assay response is proportional to the amount of enzyme in the DBS.

Figure 5A:
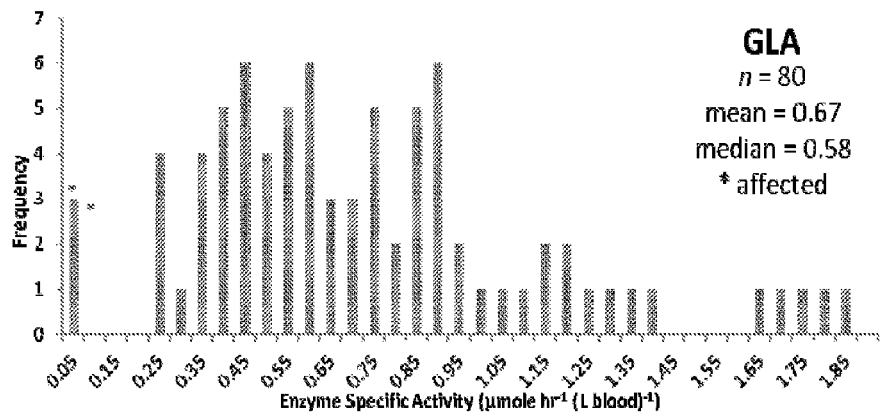
FIGS. 5A-5C illustrates assay results for n=58 randomly selected newborn DBS and n=22 affected patients using the 9-plex assay (n=80 total). Histograms for 3 LSDs (5A, GLA; 5B, GAA, and 5C, IDUA) are shown, the other 6 are illustrated in FIGURE _. The 22 affected samples are composed of 3 patients for each of the disease except for GAL4S deficiency (n=1).
Figure 5B:
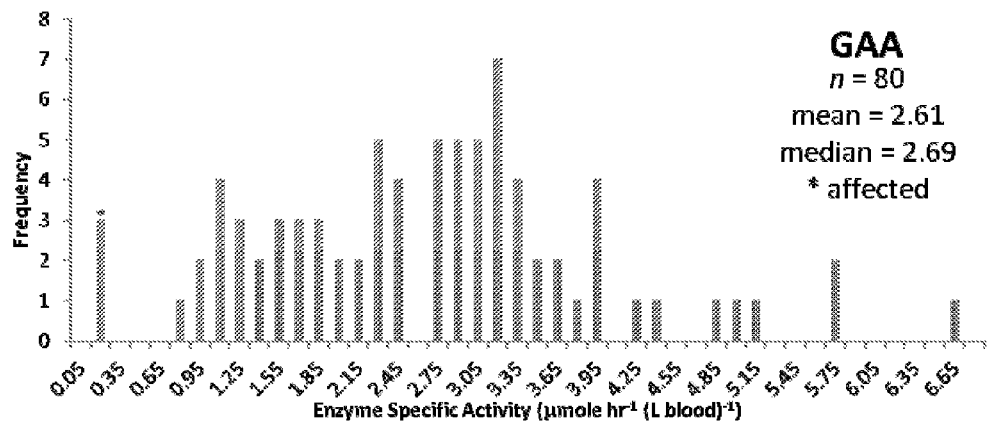
Figure 5C:
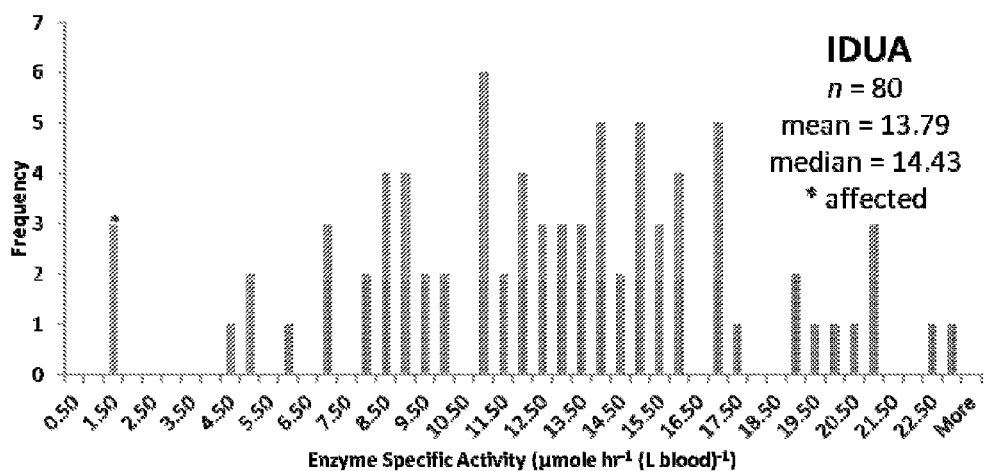
Figure 6A:
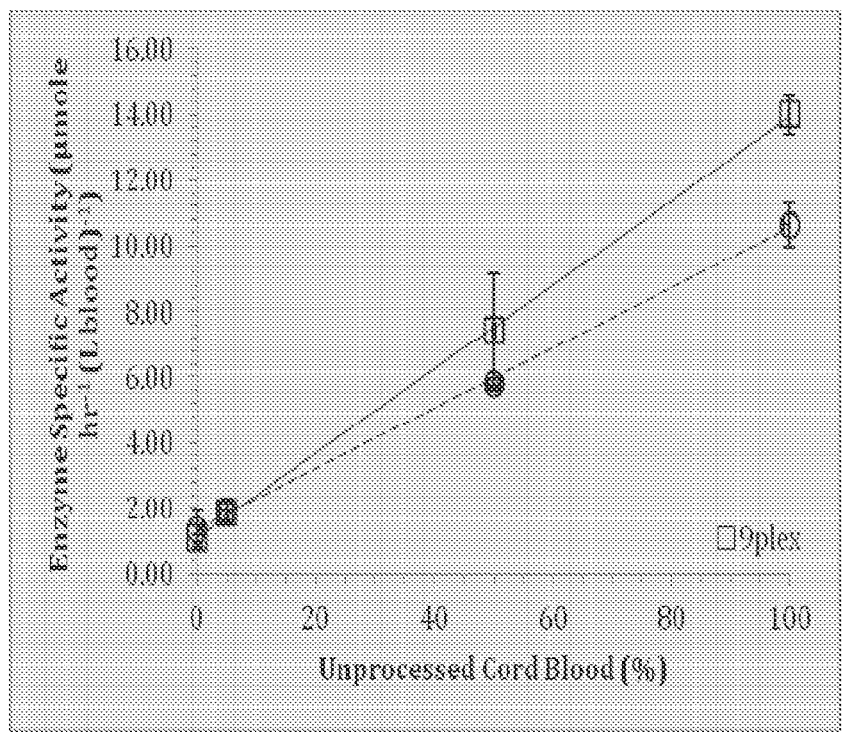
FIG. 6A-6I compare specific activities of the 9 lysosomal enzymes measured with the quality control standards provided by the CDC: 6A, IDUA; 6B, GLA; 6C, GAA; 6D, ASM; 6E, GALC; 6F, ABG; 6G, GAL4S; 6H, GAL6S; 6I, ID2S. The specific activities are calculated assuming each 3 mm DBS has 3.1 µL of blood. The circles are the 6+3-plex, and the squares are the 9-plex. The CDC samples are prepared from leukocyte depleted blood that has been mixed with various amounts of pooled, unprocessed cord blood (De Jesus, V. R. et al. Development and evaluation of quality control dried blood spot materials in newborn screening for lysosomal storage disorders. *Clin. Chem.* 55, 158-164 (2009)). Error bars are standard deviations measured using 2-separated punches of the quality control DBS.
Figure 6B:
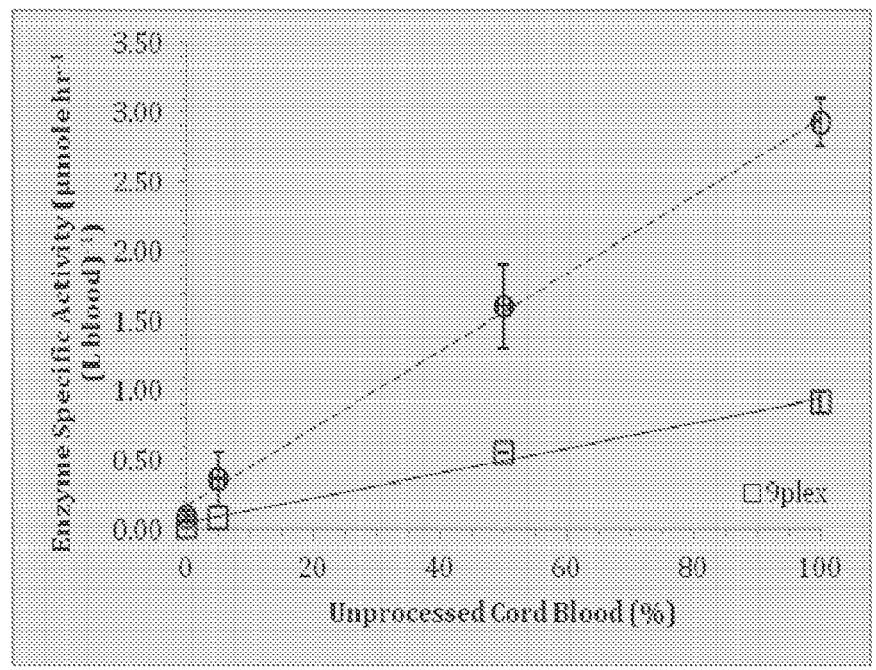
Figure 6C:
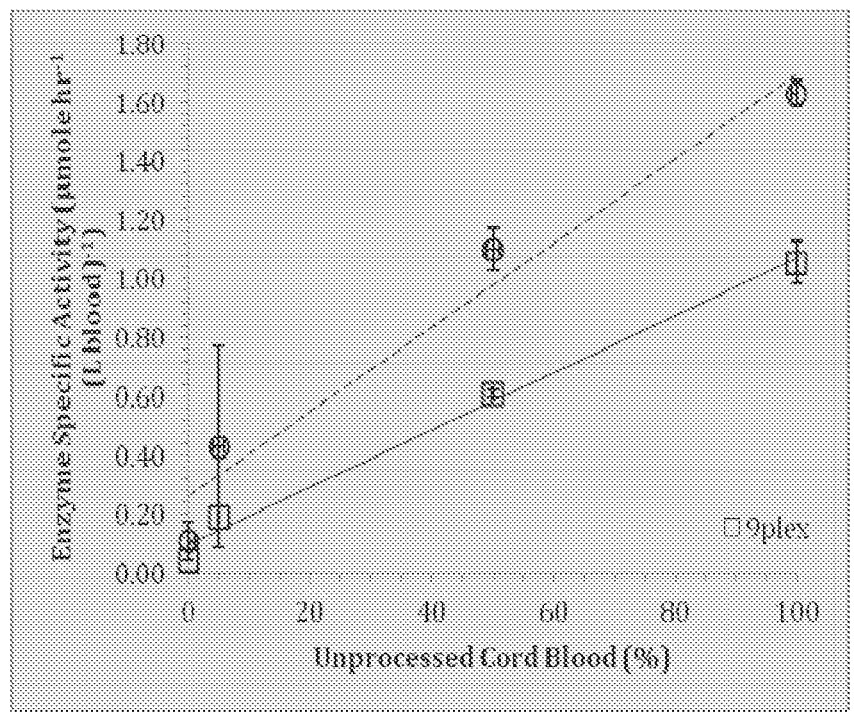
Figure 6D:
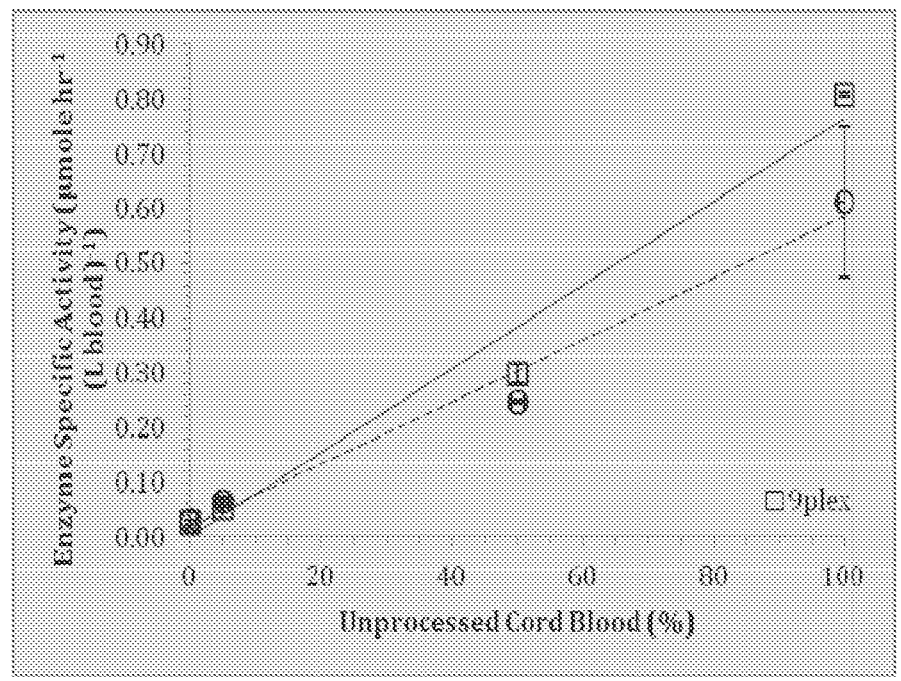
Figure 6E:
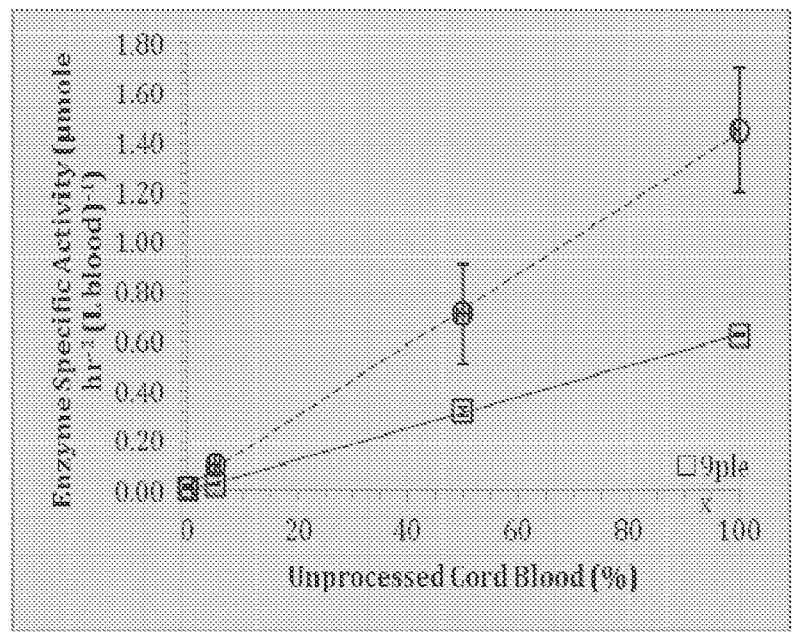
Figure 6F:
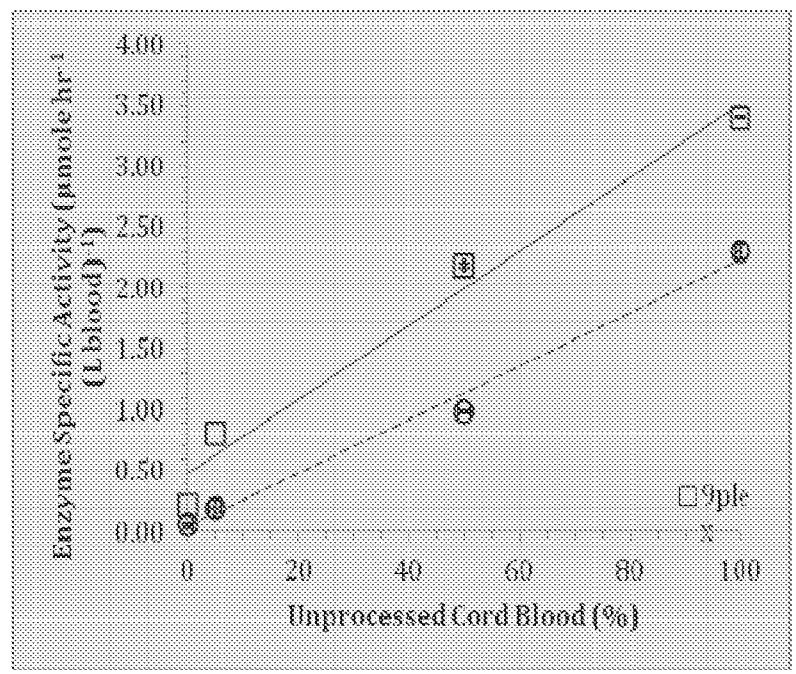
Figure 6G:
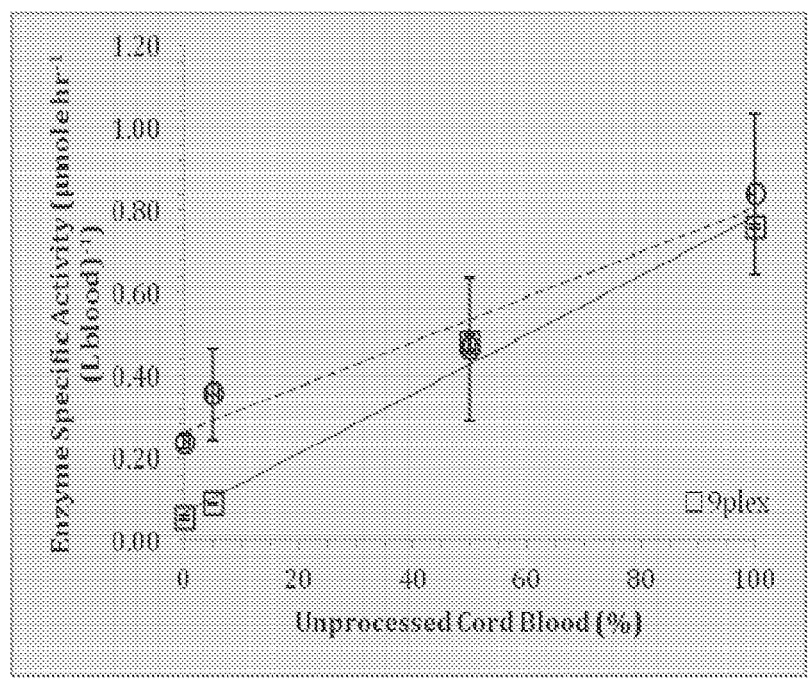
Figure 6H:
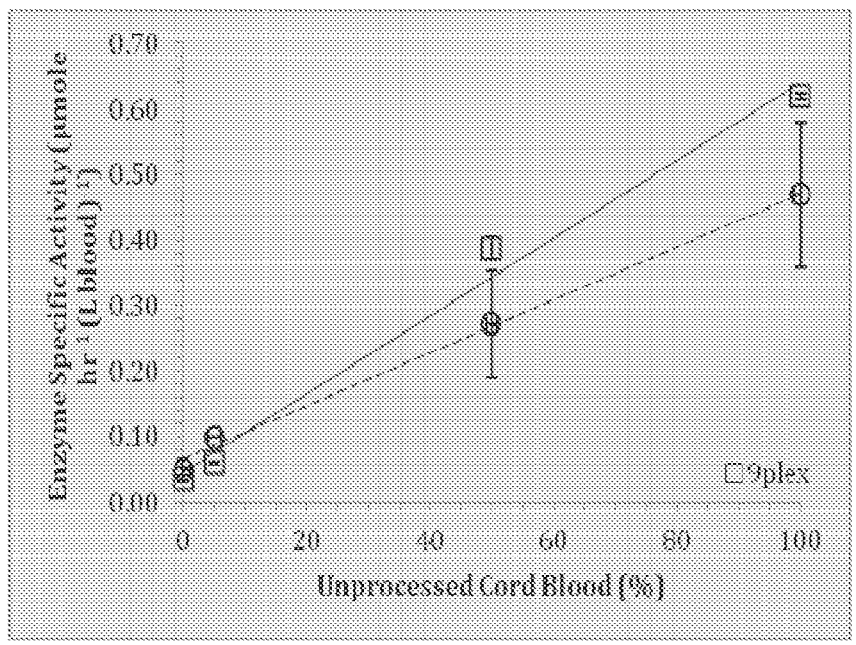
Figure 6I:
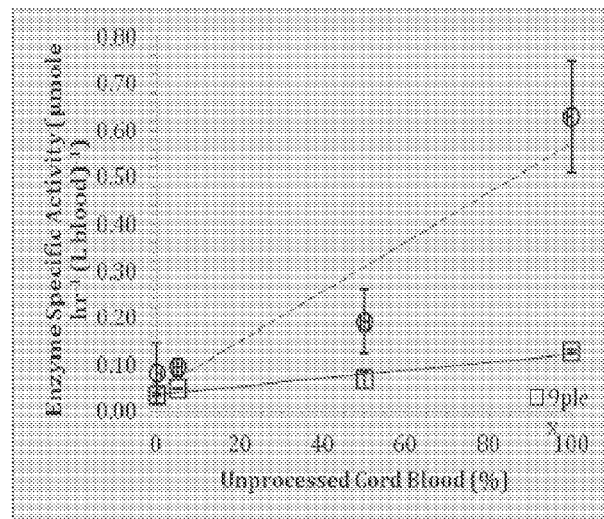
Figure 7A:
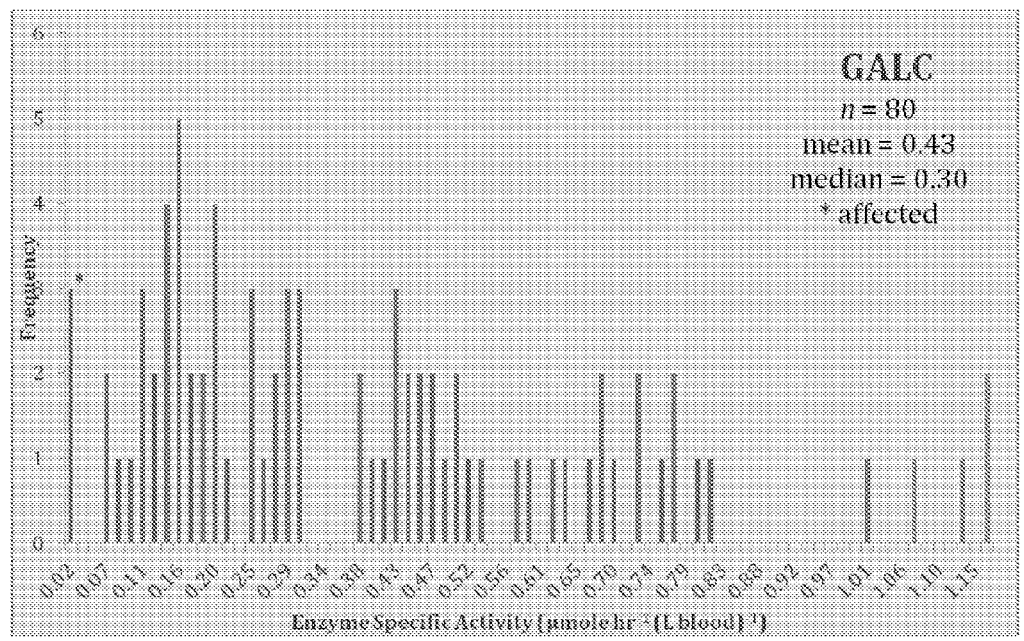
FIGS. 7A-7F are plots for the indicated LSDs analogous to those in FIGS. 5A-5C (9-plex assay). The Y-axis is number of samples. Samples from ASM-affected individuals were not tested.
Figure 7B:
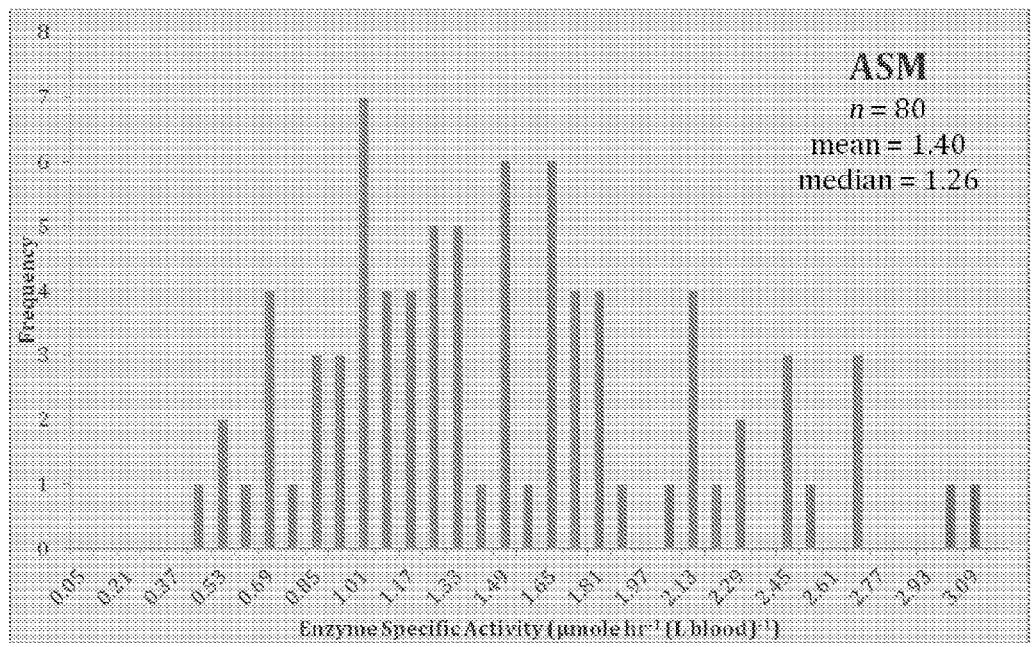
Figure 7C:
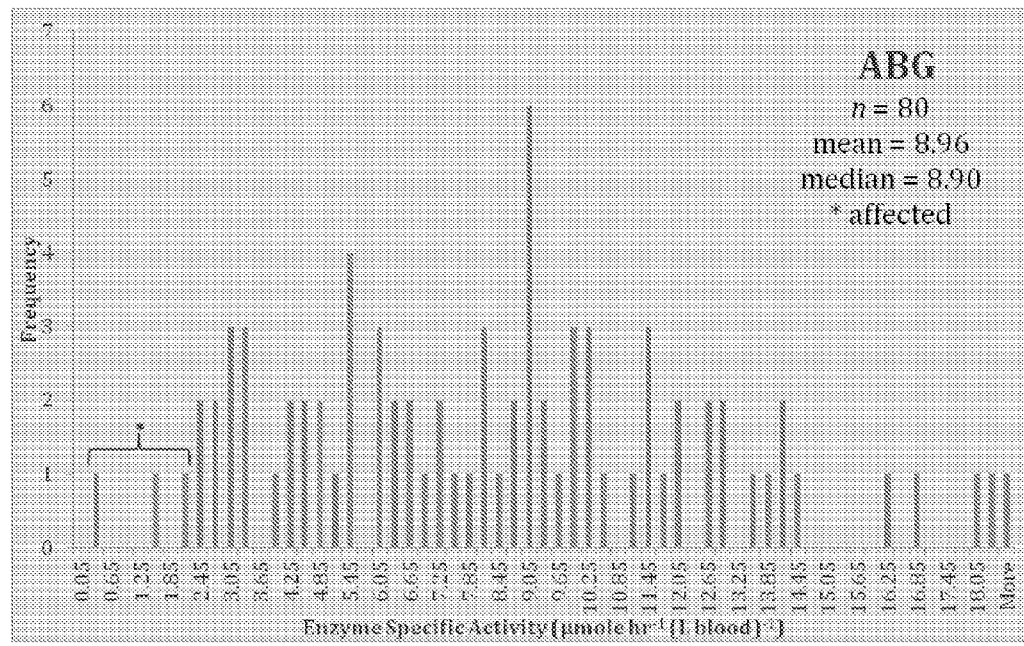
Figure 7D:
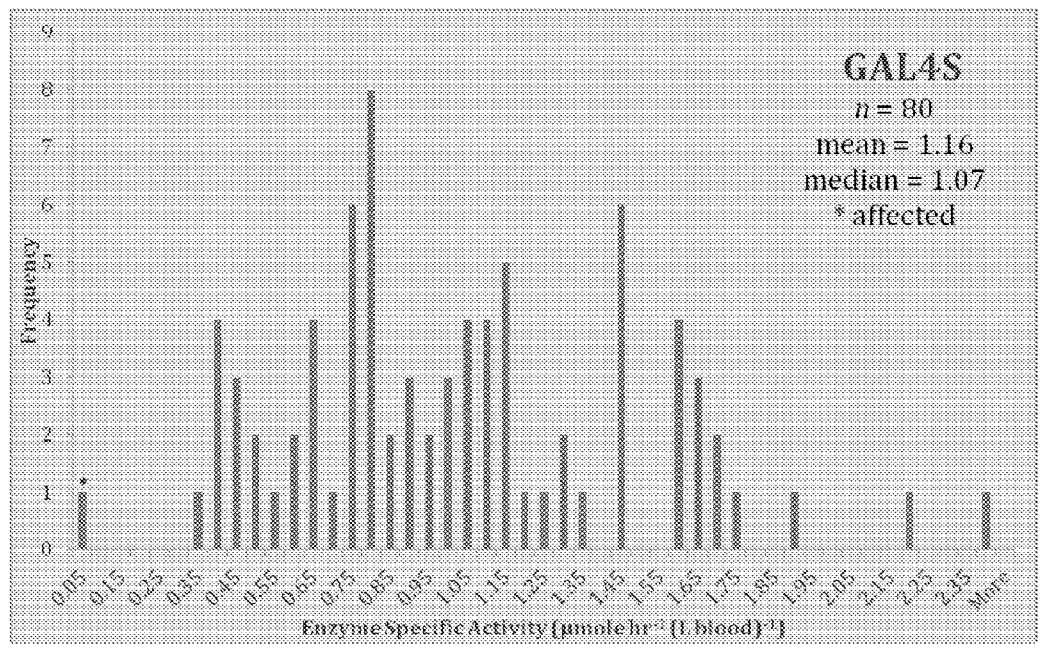
Figure 7E:
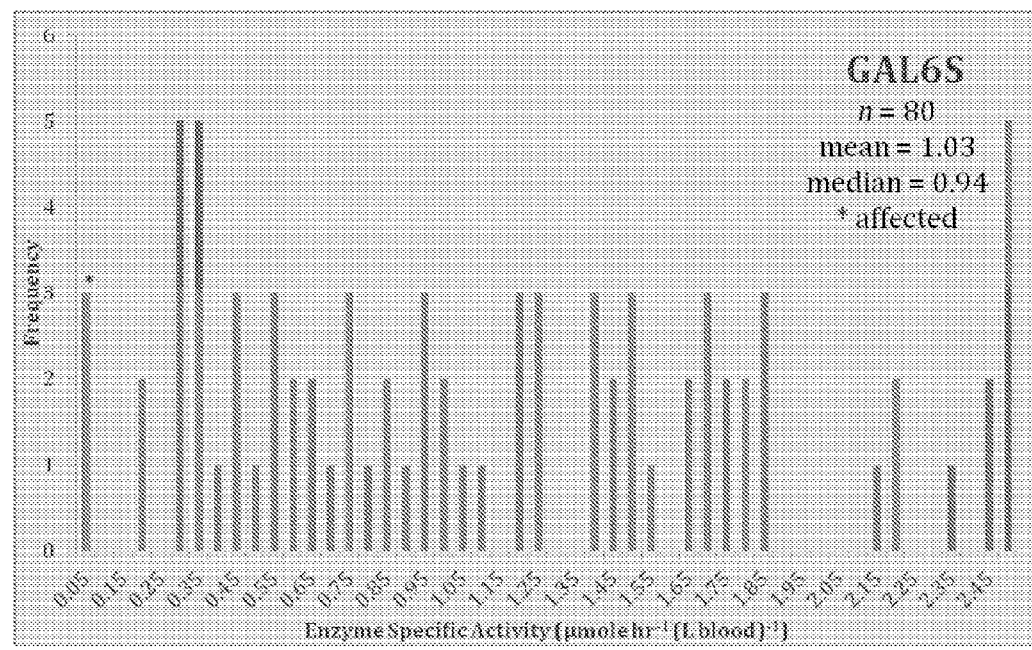
Figure 7F:
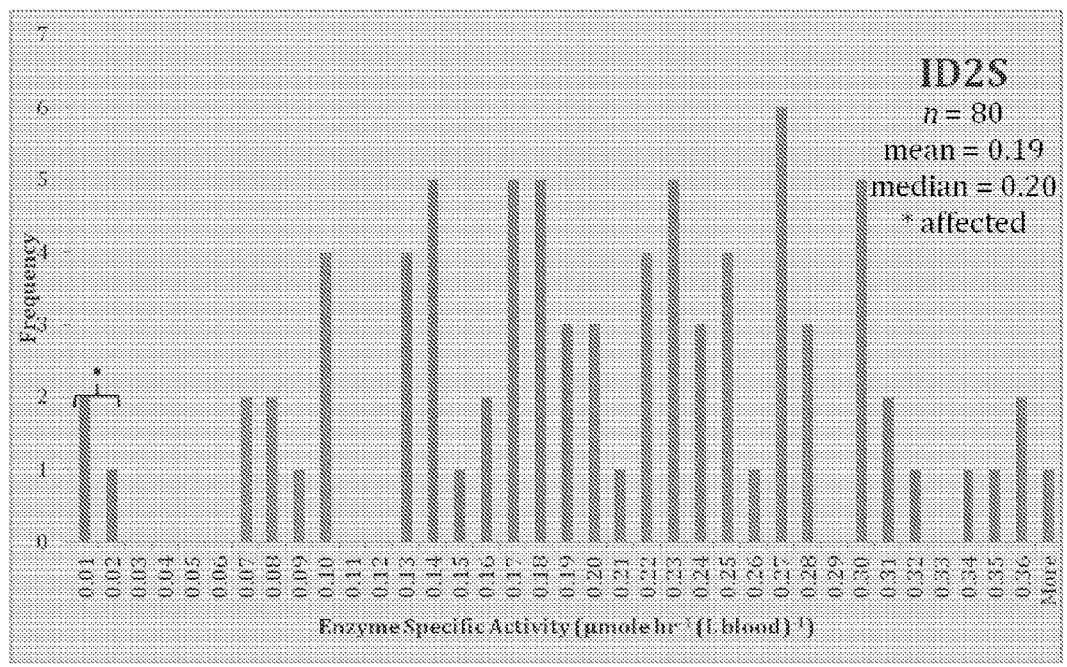
Figure 8A:
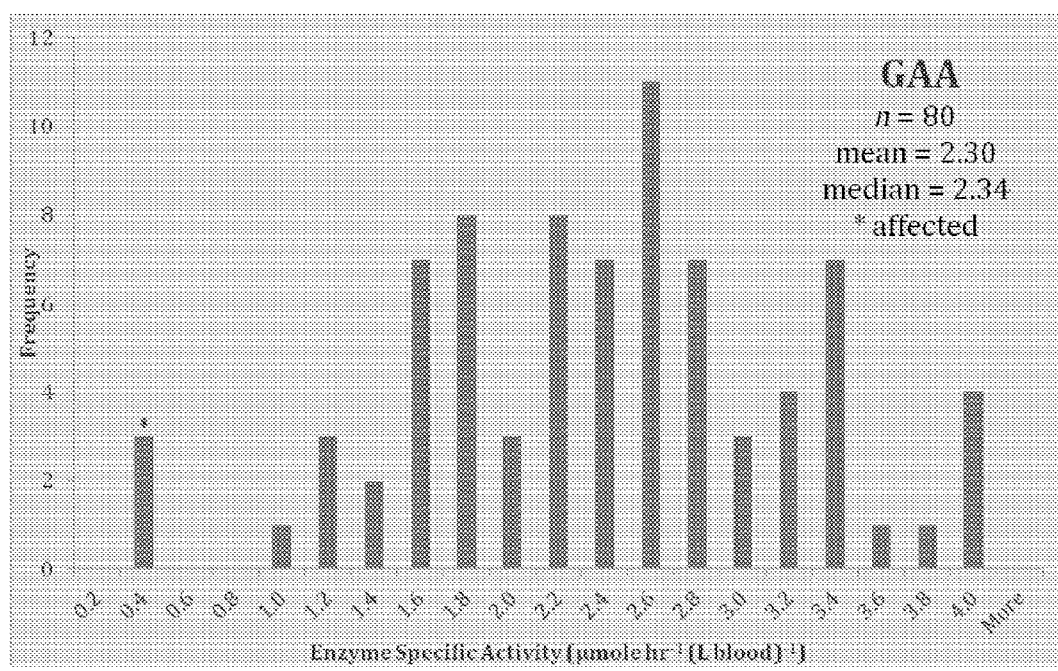
FIGS. 8A-8I are plots for the indicated LSDs analogous to those in FIGS. 5A-5C except they were obtained with the 6+3-plex rather than the 9-plex. The Y-axis is specific activity (µmol $hr^{-1}$ (L blood)$^{-1}$). No data was generated for ASM-affected individuals.
Figure 8B:
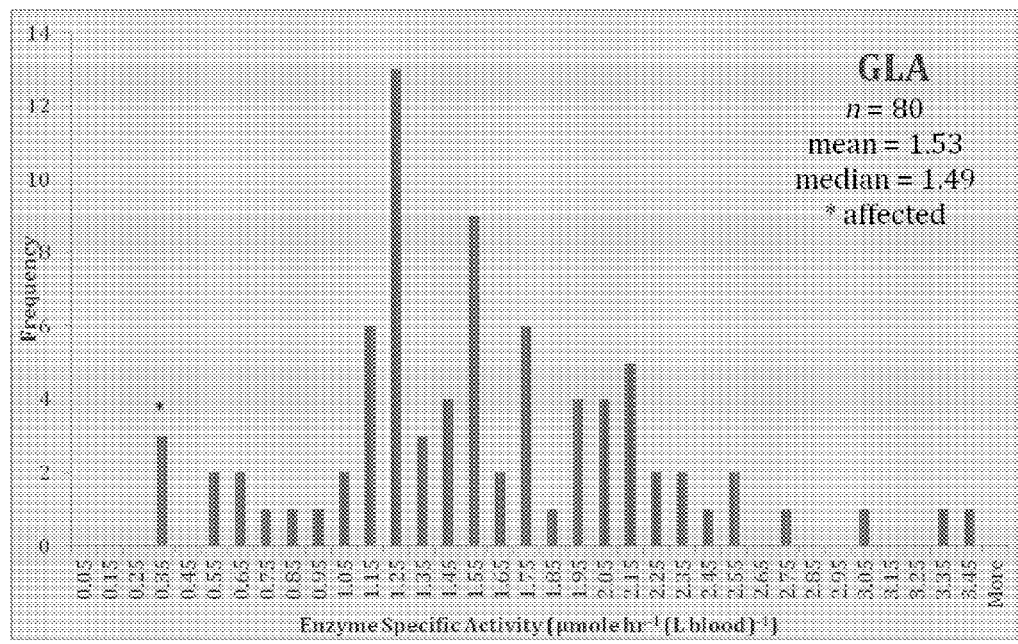
Figure 8C:
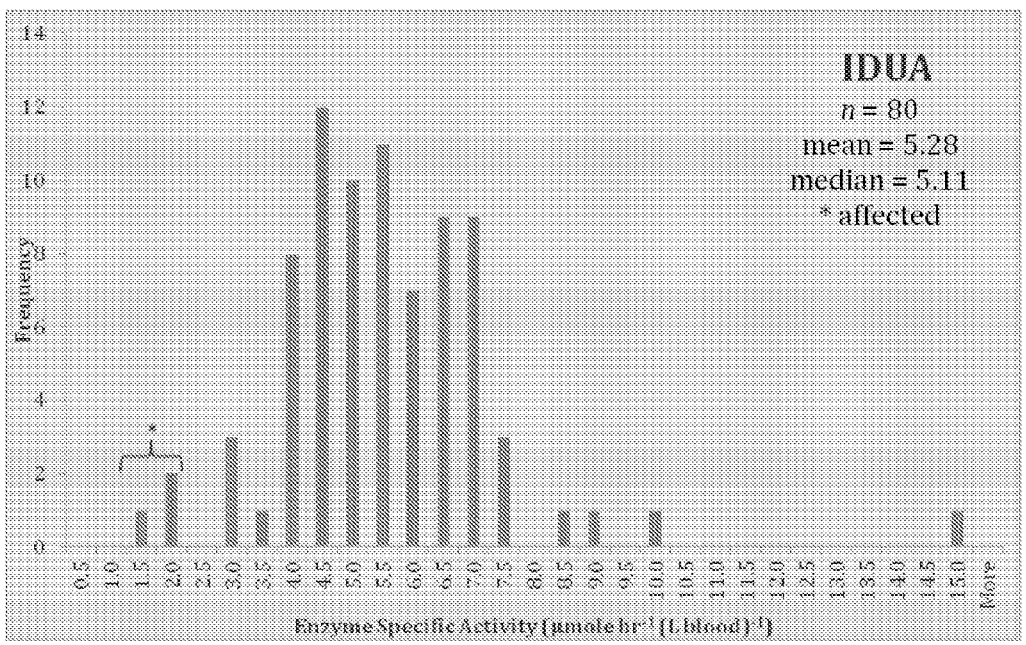
Figure 8D:
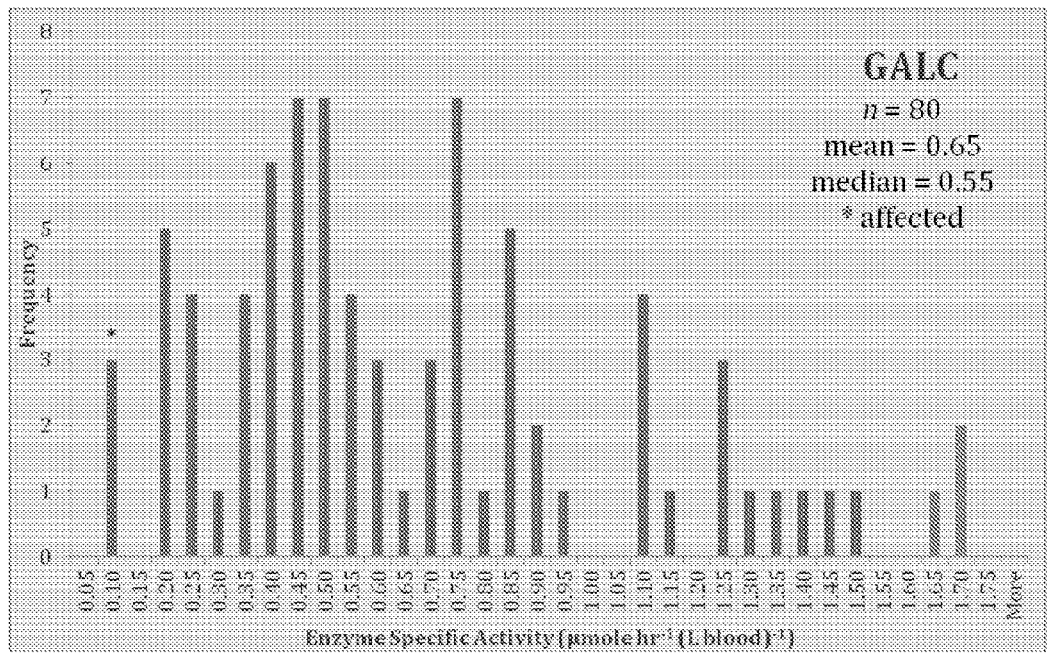
Figure 8E:
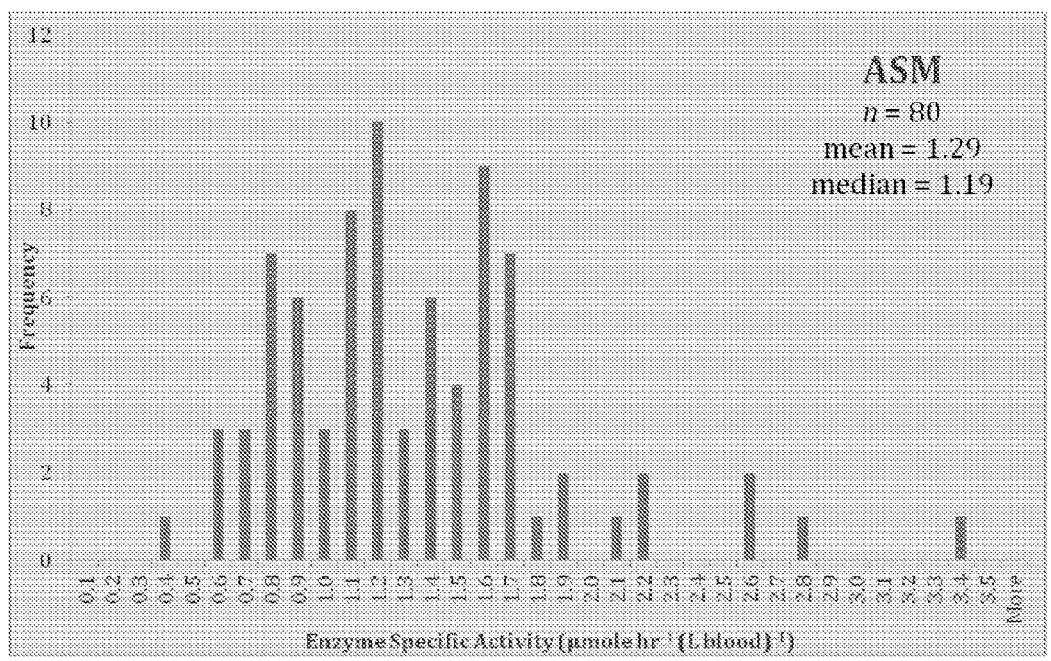
Figure 8F:
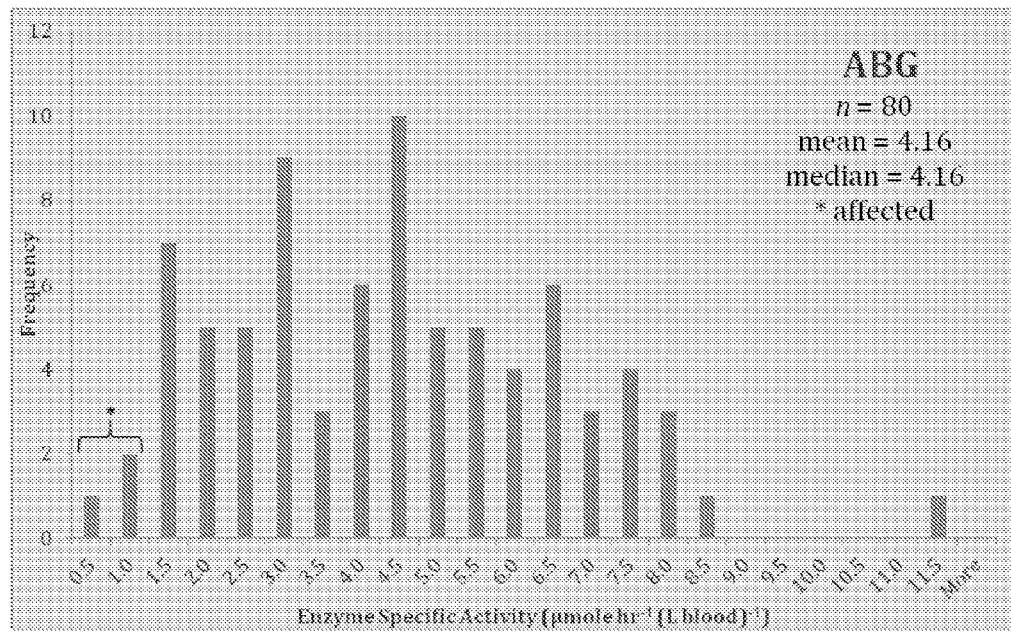
Figure 8G:
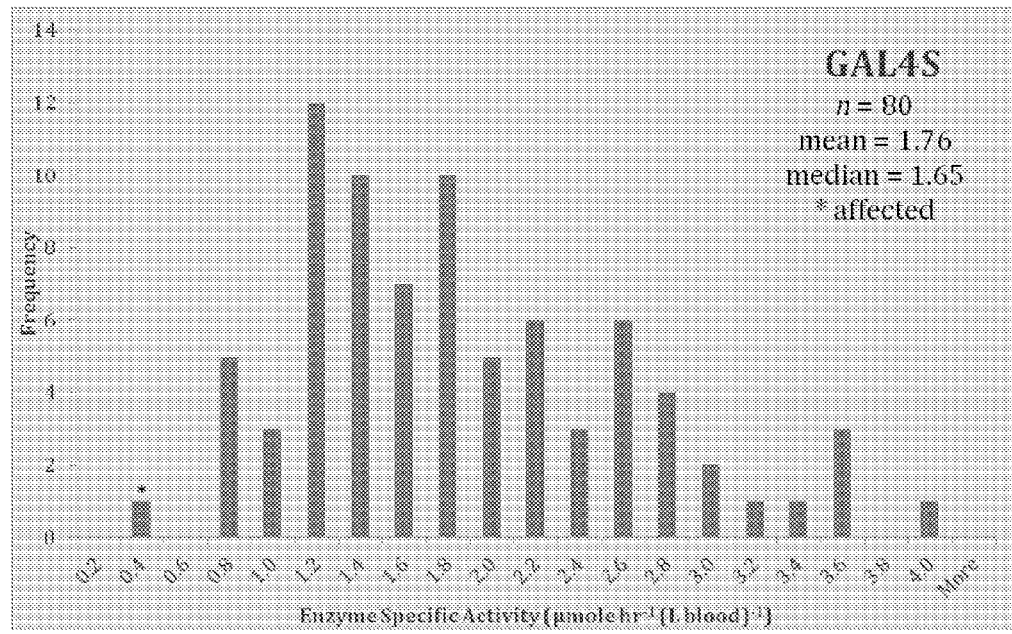
Figure 8H:
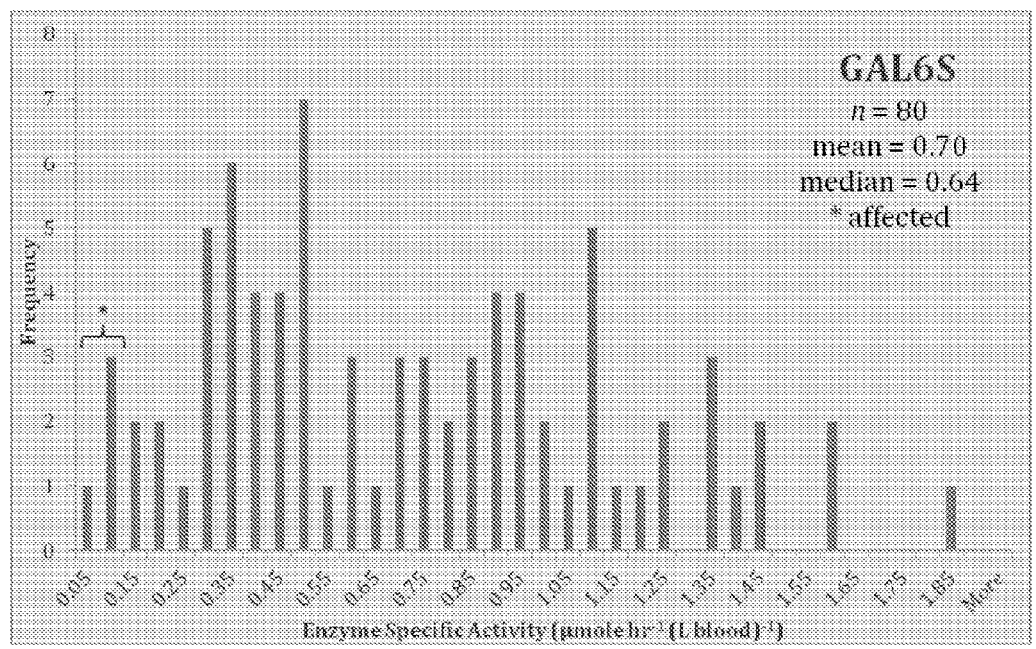
Figure 8I:
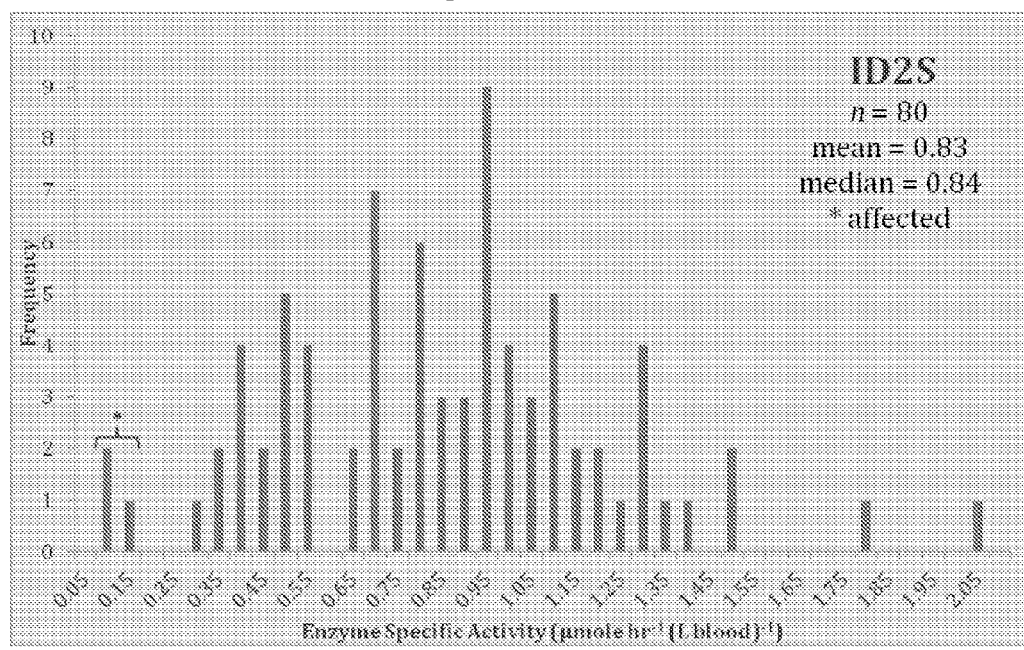

FIGS. 5A-5C shows the distribution of specific activity for GLA, GAA and IDUA enzymes, respectively, when measured with 80 DBS from random newborns and several LSD affected individuals (not newborns but older patients) (plots for the other six LSDs are provided in FIGS. 7A-7F). For all nine LSDs, the samples from the diagnosed patients showed enzyme activities below those from the random newborns.

Plots corresponding to FIGS. 5A-5C and 7A-7F obtained for the 6+3-plex assay are shown in FIGS. 8A-8I. In all cases the affected individuals have specific activities well below those of the 58 random newborns.

Enzyme specific activities (μmole $hr^{-1}$ (L blood)$^{-1}$) (average±standard deviation) for the 9-plex (top) or 6-plex+3-plex (bottom) assays described above (LC-MSMS) are summarized in Table 1. In Table 1, "Single DBS" refers to a DBS from a single healthy newborn that was punched six times; "Normal DBS" refers to 58 randomly selected newborns, each punched one time; and the blank refers to an assay with a blood-free filter paper punch instead of one containing dried blood. The 6-plex includes the enzymes IDUA (alpha-L-iduronidase, Mucopolysaccharidosis-I), GLA (alpha-galactosidase A, Fabry), GAA (acid alpha-glucosidase, Pompe), ASM (acidic sphingomyelinase, Niemann-Pick Types A/B), GALC (galactocerebrosidase, Krabbe), and ABG (acid beta-D-glucosidase, Gaucher). The 3-plex includes the enzymes GAL4S(N-acetylgalactosamine-4-sulfate sulfatase, Mucopolysaccharidosis-VI), GAL6S(N-acetylgalactosamine-6-sulfate sulfatase, Mucopolysaccharidosis-IVA), and ID2S (iduronate sulfatase, Mucopolysaccharidosis-II). The 9-plex includes the enzymes in the 6-plex and the enzymes in the 3-plex.

TABLE 1

Enzyme Specific Activity ($\mu$mole hr$^{-1}$ (L blood)$^{-1}$) measured with the 9-plex or 6 + 3-plex assays.

| | Average ± Standard Deviation Enzyme | | | | | | | | |
|---|---|---|---|---|---|---|---|---|---|
| | IDUA | GLA | GAA | ASM | GALC | ABG | GAL4S | GAL6S | ID2S |
| | | | | | Disease | | | | |
| | MPS-I | Fabry | Pompe | Niemann-Pick-A/B | Krabbe | Gaucher | MPS-IVA | MPS-VI | MPS-II |
| 9-plex | | | | | | | | | |
| Blank (n = 6) | 0.09 ± 0.025 | 0.01 ± 0.001 | 0.02 ± 0.011 | 0.01 ± 0.005 | 0.00 ± 0.002 | 0.04 ± 0.023 | 0.04 ± 0.025 | 0.01 ± 0.004 | 0.01 ± 0.011 |
| CDC QC Base (n = 2) | 1.08 ± 0.117 | 0.02 ± 0.002 | 0.05 ± 0.000 | 0.03 ± 0.004 | 0.01 ± 0.003 | 0.22 ± 0.046 | 0.06 ± 0.020 | 0.04 ± 0.011 | 0.04 ± 0.030 |
| CDC QC Low (n = 2) | 1.84 ± 0.305 | 0.08 ± 0.001 | 0.19 ± 0.002 | 0.06 ± 0.002 | 0.03 ± 0.001 | 0.81 ± 0.020 | 0.09 ± 0.006 | 0.06 ± 0.008 | 0.05 ± 0.006 |
| CDC QC Medium (n = 2) | 7.42 ± 1.727 | 0.55 ± 0.008 | 0.61 ± 0.015 | 0.30 ± 0.017 | 0.32 ± 0.023 | 2.19 ± 0.033 | 0.48 ± 0.058 | 0.39 ± 0.073 | 0.07 ± 0.009 |
| CDC QC High (n = 2) | 13.98 ± 0.564 | 0.91 ± 0.075 | 1.06 ± 0.074 | 0.81 ± 0.005 | 0.63 ± 0.031 | 3.40 ± 0.096 | 0.76 ± 0.043 | 0.62 ± 0.013 | 0.13 ± 0.017 |
| Single DBS (n = 6) | 12.37 ± 0.859 | 1.17 ± 0.033 | 1.54 ± 0.066 | 0.84 ± 0.096 | 4.30 ± 0.237 | 6.12 ± 0.300 | 0.87 ± 0.072 | 0.71 ± 0.056 | 0.08 ± 0.016 |
| Normal DBS (n = 58) | 14.05 ± 3.621 | 0.82 ± 0.378 | 3.04 ± 1.157 | 1.62 ± 0.579 | 0.48 ± 0.368 | 9.89 ± 3.925 | 1.16 ± 0.424 | 1.54 ± 0.915 | 0.23 ± 0.069 |
| Affected DBS (n = 3) | 1.43 ± 0.267 | 0.03 ± 0.004 | 0.15 ± 0.019 | n/a* | 0.01 ± 0.003 | 1.41 ± 1.128 | 0.06** | 0.01 ± 0.003 | 0.02 ± 0.008 |
| 6 + 3-plex | | | | | | | | | |
| Blank (n = 6) | 0.23 ± 0.300 | 0.02 ± 0.032 | 0.05 ± 0.087 | 0.02 ± 0.03 | 0.01 ± 0.005 | 0.02 ± 0.044 | 0.17 ± 0.084 | 0.01 ± 0.021 | 0.01 ± 0.009 |
| CDC QC Base (n = 2) | 1.36 ± 0.56 | 0.10 ± 0.036 | 0.11 ± 0.067 | 0.03 ± 0.016 | 0.02 ± 0.006 | 0.06 ± 0.018 | 0.24 ± 0.015 | 0.05 ± 0.015 | 0.08 ± 0.066 |
| CDC QC Low (n = 2) | 1.92 ± 0.305 | 0.36 ± 0.199 | 0.43 ± 0.344 | 0.06 ± 0.008 | 0.11 ± 0.036 | 0.19 ± 0.072 | 0.36 ± 0.109 | 0.10 ± 0.000 | 0.09 ± 0.019 |
| CDC QC Medium (n = 2) | 5.77 ± 0.166 | 1.61 ± 0.301 | 1.10 ± 0.074 | 0.25 ± 0.004 | 0.71 ± 0.200 | 0.99 ± 0.013 | 0.46 ± 0.173 | 0.27 ± 0.081 | 0.19 ± 0.068 |
| CDC QC High (n = 2) | 10.65 ± 0.651 | 2.93 ± 0.169 | 1.63 ± 0.041 | 0.61 ± 0.137 | 1.45 ± 0.249 | 2.30 ± 0.064 | 0.84 ± 0.195 | 0.47 ± 0.111 | 0.63 ± 0.120 |
| Single DBS (n = 6) | 16.72 ± 0.613 | 5.00 ± 0.519 | 3.78 ± 0.318 | 0.81 ± 0.098 | 3.94 ± 0.650 | 4.88 ± 0.619 | 0.89 ± 0.122 | 0.52 ± 0.133 | 0.08 ± 0.033 |
| Normal DBS (n = 58) | 5.77 ± 1.771 | 1.68 ± 0.535 | 2.59 ± 0.662 | 1.39 ± 0.526 | 0.74 ± 0.382 | 4.95 ± 1.935 | 2.03 ± 0.705 | 0.83 ± 0.330 | 0.98 ± 0.298 |
| Affected DBS (n = 3) | 1.95 ± 0.663 | 0.33 ± 0.115 | 0.31 ± 0.197 | n/a | 0.09 ± 0.090 | 0.58 ± 0.409 | 0.28* | 0.08 ± 0.029 | 0.02 ± 0.006 |

Table 1 reveals, in some cases, differences in absolute enzyme specific activity measured for the 9-plex assay compared to the 6-plex and 3-plex; this is because the assay buffers differ in pH, additives and volume used for incubation. Hence the absolute enzyme activity of healthy specimen always has to be compared to enzyme activity of affected individuals, which determines the analytical resolution of the enzyme assay. Results show that sufficient analytical resolution is feasible for either the 9-plex or 6+3-plex enzyme assays (see FIGS. 5A-5C, 7A-7F, and 8A-8I). The 6-+3-plex assay provides somewhat higher resolution for ID2S compared to 9-plex, while the average normal DBS enzyme specific activity is 0.98±0.298 and 0.23±0.069 mmole hr$^{-1}$ (L blood)$^{-1}$, respectively.

High reproducibility of the analytical system is documented by results from a System Suitability Test (see Table 5 in Example 1), which demonstrates coefficients of variation of <1% and <15% for retention time and peak area, respectively, for all product and internal standard. The overall enzyme activity variance measured for single DBS (n=6) was typically <12% (Table 1). The LC-MS/MS platform is readily transferable across commercially available instrumentation. To support the latter statement, similar optimized parameters were demonstrated (e.g., collision energy for various triple quadrupole mass analyzers in Tables 3 and 4 in Example 1).

Most newborn screening laboratories use flow-injection (FI) MS/MS rather than LC-MS/MS. LC-MS/MS may be implemented in newborn screening labs. First, LC-MS/MS has been shown to work well in newborn screening laboratories. Second, UHPLC-MS/MS is used on thousands of samples daily in the pharmaceutical industry, mostly for pharmacokinetic and quality control analyses. Third, experimental results show that LC resolution and column backpressure are stable after at least 3,000 runs of the assay. Thus, UHPLC column cost will not substantially add to the cost of newborn screening, and columns can be changed in <10 min. Fourth, the void volume from the LC column, where most of the ionic and polar blood-derived components are present, is diverted to waste rather than the mass spectrometer, thus minimizing contamination of the electrospray source. The addition of LC to the MS/MS platform is expected to ramp up in newborn screening labs over the next few years. MS/MS provides much more information than conventional fluorometric assays. For example, it has recently been shown that the monitoring of psychosine levels in DBS by LC-MS/MS potentially provides a better way to stratify potential Krabbe patients in cases where low GALC enzymatic activity does not correlate with a severe phenotype.

The issue of enzyme stability in DBS can be an issue. Poorly controlled environmental factors may reduce enzyme specific activities. One advantageous feature of the multiplex assay of the invention is that a drop in specific activity of several enzymes would indicate a poorly handled DBS. A drop in activity of three sulfatases measured in the multiplex assay would suggest the possibility of multiple sulfatase deficiency.

One advantage of the LC platform over flow injection is that the pre-mass spectrometry steps for the former are reduced to a minimum, whereas the latter requires either liquid-liquid extraction of assay mixture with organic solvent or additional solid-phase extraction using silica gel or ion exchange resin to remove substrates and buffer salts. Relatively large amounts of substrate compared to product and internal standard are injected onto the LC column, and significant ionization suppression of products and internal standards by substrates will occur if adequate LC resolution is not obtained. On the other hand, most of the substrates are removed by the pre-mass spectrometry sample processing in certain methods involving flow injection. In flow injection, a single solution of uniform composition is infused into the mass spectrometer and products and internal standards are quantified over a relatively long period of time (typically tens of seconds). In LC-MS/MS, products and internal standards elute over a relatively short time period of a few seconds, and the composition of the eluent entering the mass spectrometer source changes over time.

As described above, in one embodiment, the enzyme assay samples are introduced to mass analysis by liquid chromatography (LC-MSMS). In another embodiment, the enzyme product samples are introduced to mass analysis by flow injection (FI-MSMS). In this embodiment, the enzyme assay sample is introduced into the MSMS instrument by flow-injection in which the liquid stream goes directly from the injector system to the MSMS ionization source without the need for LC. In this case, it is important to tune the electrospray ionization parameters so as to minimize the amount of in-source decomposition of substrate to give product while at the same time to not reduce the efficiency of ionization of the product and internal standard significantly. A person trained in the art of using MSMS will be knowledgeable in the techniques for achieving such tuning. A suitable solvent for flow-injection of sample into the MSMS is methanol/water mixtures with or without formic acid or ammonium formate, but other infusion solvents are also useful.

Flow injection was used to introduce enzyme samples (6-plex) into the MSMS instrument. The 6-plex was the same six enzymes described above and for which results are tabulated in Table 1. Enzyme specific activities (μmole hr$^{-1}$ (L blood)$^{-1}$) (average±standard deviation) for the 6-plex FI-MSMS assay determined by this method are summarized in Table 2. In the table, "Single DBS" refers to a DBS from a single healthy newborn. The blank refers to an assay with a blood-free filter paper punch instead of one containing dried blood.

TABLE 2

Enzyme Specific Activity (μmole hr$^{-1}$ (L blood)$^{-1}$) measured with the 6-plex assay.

| | Enzyme | | | | | |
|---|---|---|---|---|---|---|
| | IDUA | GLA | GAA | ASM | GALC | ABG |
| | | | | Disease | | |
| | MPS-I | Fabry | Pompe | Niemann-Pick-A/B | Krabbe | Gaucher |
| Blank (n = 1) | 0.61 | 0.06 | 0.11 | 0.02 | 0.09 | 0.43 |
| Single DBS (n = 1) | 43.9 | 1.83 | 3.09 | 0.76 | 0.55 | 5.17 |

As described above, the invention provides a simplified assay of nine lysosomal enzymes that makes use of either one or two DBS punches in either one or two assay cocktails appropriate for newborn screening. The assay of nine enzymes is carried out either in a single buffer or in two buffers with a cassette of substrates and internal standards and one or two punches of a dried blood spot (DBS) on a newborn screening card as the source of enzymes. In this embodiment, the pre-HPLC-MS/MS sample preparation requires only four liquid transfers before injection into a dual column HPLC equipped with switching valves to direct the flow to separation and column equilibration. Product- and internal standard specific ion fragmentations are used for MS/MS quantification in the selected reaction mode (SRM). As described in detail below, analysis of blood spots from fifty-eight (58) random newborns and from lysosomal storage disease affected patients showed that the assay readily distinguishes affected from non-affected individuals. The time per 9-plex analysis (1.8 min) is sufficiently short to be compatible with the workflow of newborn screening laboratories. In this embodiment (HPLC-MS/MS) provides a viable alternative to flow injection MS/MS for the quantification of lysosomal enzyme activities. The method enables the assay nine of lysosomal enzymes using one or two reaction buffers, thus minimizing the number of separate incubations that need to be carried out.

Sextuplex (6-Plex) Assay (GAA. GLA. IDUA, ABG, GALC, ASM)

In one embodiment, the invention provides a multiplex enzyme assay of six (6) lysosomal enzymes using a second enzyme reaction buffer. Six lysosomal enzymes are assayed in the sextuplet assay:

(1) α-glucosidase (GAA) (Pompe disease);
(2) α-galactosidase (GLA) (Fabry disease);
(3) α-L-iduronidase (IDUA) (Mucopolysaccharidosis Type I);
(4) β-glucocerebrosidase (ABG) (Gaucher disease);
(5) β-galactocerebrosidase (GALC) (Krabbe disease); and
(6) sphingomyelinase (ASM) (Niemann-Pick Type A/B disease).

Figure 14:
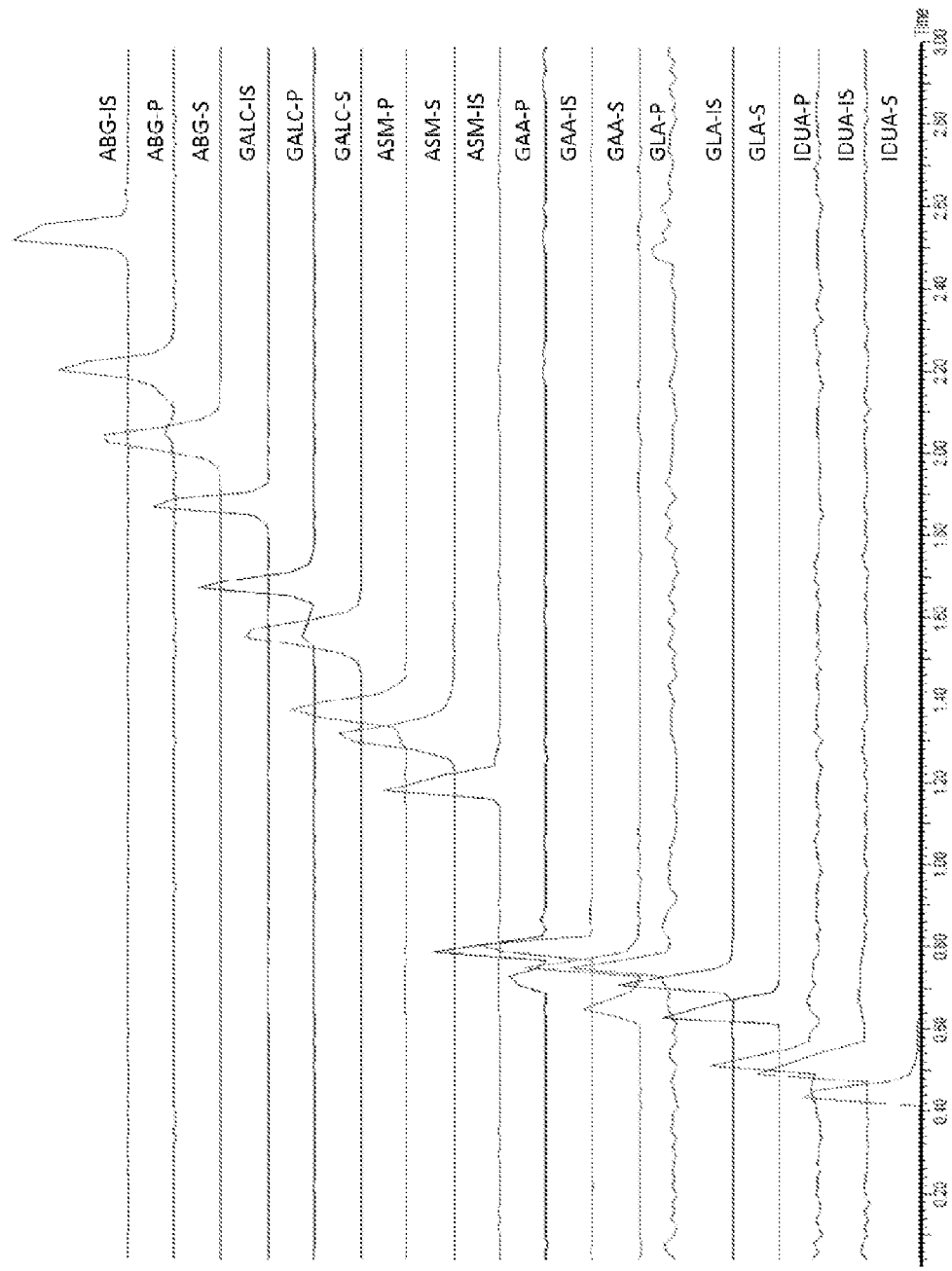
FIG. 14 compares the ultra-high performance liquid chromatography (UHPLC) separation of substrates, products and internal standards for six (6) lysosomal enzymes: ABG (Gaucher disease), GALC (Krabbe disease), ASM (Niemann-Pick Type A/B disease), GLA (Fabry disease), GAA (Pompe disease) and IDUA (Mucopolysaccharidosis Type I). Substrates, products and internal standards for Mucopolysaccharidosis Type IVA, Mucopolysaccharidosis Type II, and Mucopolysaccharidosis Type VI (not shown) can be similarly separated. The indicated ion peaks were detected by tandem mass spectrometry. LC-MS/MS chromatogram acquired after injection (10 µL) of processed sextuplex assay sample belonging to healthy individual (each SRM channel represents one substrate, one product, or one internal standard, see Table 6 for details).

The ultra-high performance liquid chromatography (UHPLC) separation of substrates, products, and internal standards for six (6) lysosomal enzymes (ABG (Gaucher disease), GALC (Krabbe disease), ASM (Niemann-Pick Type A/B disease), GLA (Fabry disease), GAA (Pompe disease) and IDUA (Mucopolysaccharidosis Type I)) are compared in FIG. 14. Substrates, products and internal standards for Mucopolysaccharidosis Type IVA, Mucopolysaccharidosis Type II, and Mucopolysaccharidosis Type VI (not shown) can be similarly separated. The indicated ion peaks were detected by tandem mass spectrometry. LC-MS/MS chromatogram acquired after injection (10 μL) of processed sextuplex assay sample belonging to healthy individual (each SRM channel represents one substrate, one product, or one internal standard, see Table 7 for details).

The 6-plex enzyme reaction buffer includes:
(a) a maltase glucoamylase inhibitor; and
(b) one or more surfactants.

Suitable components of the 6-plex enzyme reaction buffer are as described above for the enzyme reaction solutions. In one embodiment, the enzyme reaction buffer useful in the 6-plex assay includes ammonium formate (prepared from formic acid and ammonium hydroxide), sodium taurocholate, and acarbose. The preparation of a representative enzyme reaction buffer and its use in a sextuplex assay are described in Examples 2 and 4.

Triplex (3-Flex) Assay (ID2S, GAL6S, GAL4S).

In another embodiment, the invention provides a multiplex enzyme assay of three (3) lysosomal enzymes using a third enzyme reaction buffer. Three lysosomal enzymes are assayed in the triplex assay:
(1) iduronate 2-sufatase (ID2S) (Mucopolysaccharidosis Type II);
(2) N-acetylgalactosamine 6-sulfatase (GAL6S) (Morquio A syndrome); and
(3) N-acetylgalactosamine 4-sulfatase (GAL4S) (Maroteaux-Lamy syndrome).

The 3-plex enzyme reaction buffer includes:
(a) one or more metal cations effective for precipitating sulfate ions;
(b) one or more metal cations effective for precipitating phosphate ions;
(c) a beta-N-acetylhexosaminidase inhibitor; and
(d) one or more surfactants.

Suitable components of the 3-plex enzyme reaction buffer are as described above for the enzyme reaction solutions. In one embodiment, the enzyme reaction buffer useful in the triplex assay includes ammonium formate (prepared from formic acid and ammonium hydroxide), barium acetate, cerium acetate, and 2-acetamido-2-deoxy-D-glucono-1,5-lactone (2A2D-GlcLactone). The preparation of a representative enzyme reaction buffer and its use in a triplex assay are described in Examples 3 and 4.

The following examples are provided for the purpose of illustrating, not limiting, the invention.

EXAMPLES

Example 1

Representative 9-Flex and 6+3-Flex Lysosomal Enzyme Assay Methods

Materials.

The substrates (S) and internal standards (IS) for α-glucosidase (GAA), α-galactosidase (GLA), α-L-iduronidase (IDUA), β-glucocerebrosidase (ABG), β-galactocerebrosidase (GALC), and sphingomyelinase (ASM) enzyme assays and the CDC quality control DBS samples were received from Dr. H. Zhou (CDC, Atlanta, Ga.). The reagents specific for iduronate 2-sufatase (ID2S), N-acetylgalactosamine 6-sulfatase (GAL6S), and N-acetylgalactosamine 4-sulfatase (GAL4S) were prepared as described in Duffey, T. A., Khaliq, T. Scott, C. R., Turecek, F., Gelb, M. H. (2010) "Design and synthesis of substrates for newborn screening of Maroteaux-Lamy and Morquio A syndromes," Bioorg. Med. Chem. Lett., 20(20):5994-5996; and Blanchard, S., Turecek, F., Gelb, M. H. (2009) "Short synthetic sequence for 2-sulfation of alpha-L-iduronate glycosides" Carbohydrate Research, 344:1032-1033. Synthetic methods have been optimized at process scale appropriate to support worldwide newborn screening. Acetonitrile ≥99.9% (cat. #34967) and methanol ≥99.9% (cat. #34860) were purchased from Sigma Aldrich (St. Louis, Mo.).

Quality control (QC) dried blood spot (DBS) samples (Lot #3-2010) were obtained from the CDC and stored at −20° C. in a zip-lock plastic bag placed in a sealed plastic box with solid desiccant (anhydrous $CaSO_4$ such as Driedrite or the equivalent). DBS of healthy individuals were received from WA state newborn screening laboratory. These are about 30-day old DBS that have been stored at ambient temperature without dessication. All DBS samples were manually punched with a 3 mm (⅛") diameter perforator.

Preparation of 9-Plex Assay Cocktail.

The S/IS vials from CDC were dissolved in methanol; GLA (10 mL); GAA and IDUA (6 mL); ABG, GALC and ASM (4 mL), and solutions were stored at −20° C. in original vials. The ID2S and GAL6S S/IS substances were accurately weighted into individual glass vials (4 mL, Fisher Scientific, cat. #22-022-944), and methanol was added resulting in 10 mM and 1 mM stock solutions of S and IS, respectively. Solutions were stored at −20° C. in vials. The GAL4S S was dissolved to 1 mM in methanol, and the GAL4S IS stock solution was prepared as for the others. Stock solutions of ID2S-S (0.5 mL), GAL4S-S (10 mL), GAL6S-S (2 mL) and of ID2S-IS, GAL6S-IS, GAL4S-IS (50 μL each) were combined into a new vial together with aliquots (1 mL) of each CDC vial, and solvent was removed in a vacuum concentrator (Savant SpeedVac; Thermo Scientific, San Jose, Calif., cat. # SC210A-115) at a medium temperature (43° C.) setting. The residue in a vial can be stored at −20° C. and reconstituted as needed as described below. 9-Plex assay buffer (10 mL, prepared as described above) was added to the residue, and the mixture was briefly vortexed with brief heating under tap water (<40° C.) until the contents were completely dissolved. The resulting solution contained 200 μM GAA-S, 2.0 μM GAA-IS, 600 μM GLA-S, 1.2 μM GLA-IS, 500 μM IDUA-S, 3.5 μM IDUA-IS, 150 μM ASM-S, 2.7 μM ASM-IS, 450 μM GALC-S, 2.8 μM GALC-IS, 300 μM ABG-S, 5.9 μM ABG-IS, 500 μM ID2S-S, 5 μM ID2S-IS, 2 mM GAL6S-S, 5 μM GAL6S-IS, 1 mM GAL4S-S, 5 μM GAL4S-IS in assay buffer. The assay cocktail was not stored.

Additional Experimental Details.

Storage conditions for all solutions are described above. When dissolving all reagents, they should be inspected visually to ensure that no particulate remains. This is especially important for the lipidic reagents (Gaucher, Niemann-Pick-A/B, and Krabbe), which disperse slowly into the detergent-containing buffer.

QC DBS are prepared from unprocessed cord blood and leukocyte-depleted blood to differ in the enzyme activity and are denoted as base (0%) (B), low (5%) (L), medium (50%) (M), and high (100%) (H) (De Jesus, V. R. et al. Development and evaluation of quality control dried blood spot materials in newborn screening for lysosomal storage disorders. Clin. Chem. 55, 158-164 (2009)). The base sample contains leukocyte-depleted blood and may still contain trace amounts of lysosomal enzymes, low (5%) is base sample+5% unprocessed cord blood, and medium is base+50% unprocessed cord blood and high is 100% unprocessed cord blood. Thus, for plotting measured enzyme activity versus the amount of enzyme in the CDC DBS control samples, the X-axis values are 0, 0.05, 0.5 and 1.0 for the B, L, M and H CDC DBS respectively. Enzyme activity in the base pool was found typically above that measured in an assay that has a 3 mm no-blood DBS punch (filter paper only), presumably because the base sample is not completely free of lysosomal enzyme. A 3 mm DBS filter paper-only punch was used to obtain a true analytical blank for enzyme activity measurements.

6+3-Plex.

To make the 6-plex assay cocktail, the S/IS vials from the CDC were dissolved in methanol; GLA (10 mL); GAA and IDUA (6 mL); ABG, GALC and ASM (4 mL), and solutions were stored at −20° C. in original vials. Aliquots (1 mL) of each vial were combined into a new vial, and the solvent was evaporated with a stream of nitrogen, argon or oil-free air, the temperature can be adjusted up to 40° C. The residue can be stored at −20° C. for at least 6 months in the capped glass vial and reconstituted as needed. The vial was reconstituted in 10 mL of 6-plex assay buffer (prepared as described above). The sample was briefly vortexed or sonicated and heated under tap water (<40° C.) until the contents were completely dissolved (visually inspected). The resulting mixture contains 200 µM GAA-S, 2.0 µM GAA-IS, 600 µM GLA-S, 1.2 µM GLA-IS, 500 µM IDUA-S, 3.5 µM IDUA-IS, 150 µM ASM-S, 2.7 µM ASM-IS, 450 µM GALC-S, 2.8 µM GALC-IS; 300 µM ABG-S, 5.9 µM ABG-IS in assay buffer. Excessive 6-plex assay cocktail was stored at −20° C. up to one month in a capped glass vial (4 mL, Fisher Scientific, cat. #22-022-944). Upon removal from the freezer, the vial was briefly vortexed or sonicated and heated under tap water (<40° C.) until the contents were completely dissolved (visually checked).

To make the 3-plex assay cocktail, the ID2S, GAL6S, and GAL4S S/IS substances were each accurately weighted into individual glass vials (4 mL, Fisher Scientific, cat. #22-022-944). For all but GAL4S 5, methanol was added to each vial to give 10 mM and 1 mM stock solutions of substrate and internal standard, respectively, and solutions were stored at −20° C. in vials (methanol can evaporate in the freezer so be sure the vial is tightly capped). For GAL4S S, the solid was dissolved in methanol to give a 1 mM stock solution. The Stock solutions of ID2S-S (0.5 mL), GAL4S-S (10 mL), GAL6S-S (2 mL), and of ID2S-IS, GAL6S-IS, and GAL4S-IS (50 µL each) were combined into a new vial, and solvent was removed in a vacuum concentrator (Savant SpeedVac; Thermo Scientific, San Jose, Calif., cat. # SC210A-115) at a medium temperature (43° C.) setting. Methanol can also be removed with a stream of gas as described above for the 6-plex assay. The residue in a vial can be stored at −10 to −20° C. and reconstituted as needed as described below. 3-Plex assay buffer (10 mL) (prepared as described above) was added to the residue in a vial, and the mixture was briefly vortexed. The resulting solution contained 0.5 mM ID2S-S, 5 µM ID2S-IS, 2 mM GAL6S-S, 5 µM GAL6S-IS, 1 mM GAL4S-S, 5 µM GAL4S-IS in 3-plex assay buffer. Excessive 3-plex assay cocktail was stored at −20° C. up to one month.

Assay Incubation.

The analyzed DBS from newborns were punched in duplicate to set up identical 96-well plates (0.5 mL, Axygen Scientific, VWR International, cat. #47743-982), later referred to as Plate 1 and 2. A standard pipettor with the desired number of channels (i.e. 1-, 6-, 12- or 96-channel), and polypropylene pipette tips were used to pipette an aliquot (30 µL) of 6-plex assay cocktail into each well of Plate 1, and an aliquot (15 µL) of 3-plex assay cocktail into each well of Plate 2. Thereafter plates were sealed with sealing film (AxySeal, VWR International, cat. #10011-117) for overnight (16 h) incubation at 37° C. with orbital shaking (250 RPM). Note we use 15 µL for the 3-plex instead of 30 µL because the sulfatase substrates are more expensive to produce, and the assays is reproducible with 15

Sample Work-Up Protocol.

After 16 h incubation of Plate 1 and 2 (representing the 6-plex and the 3-plex assay respectively), acetonitrile was added by multichannel manual pipette to quench the reactions and precipitate proteins. The 6-plex and 3-plex assay was quenched with 180 µL and 90 µL of acetonitrile per well, respectively. Plates were covered with polyester-based sealing film (AxySeal, VWR International, cat. #10011-117) and centrifuged at 3000 rpm for 5 min at room temperature to pellet the precipitate. The sealing film was removed immediately since prolonged exposure to acetonitrile softens the acrylic adhesive. The supernatant aliquots (100 µL and 80 µL) were removed from Plate 1 and 2, respectively, to avoid dislodgement of the pellet. At this point, 6-plex and 3-plex assays can be analyzed individually (1) or simultaneously in a single 9-plex assay (2). In case (1) supernatant aliquots from Plate 1 and 2 were transferred to a pair of new 96-well plates (0.5 mL, Axygen Scientific, VWR International, cat. #47743-982), and 150 µL or 120 µL of deionized water (Milli-Q, 18.2 MΩ) was added into each well, respectively, to match the sample solvent strength with initial HPLC mobile phase conditions. The plates were carefully sealed with aluminum foil and subjected directly to 6-plex (Plate 1) and 3-plex (Plate 2) LC-MS/MS analysis. For case (2) both supernatant aliquots from Plate 1 and Plate 2 were combined into a single new 96-well plate, and 270 µL of deionized water was added into each well. The combined sample plate was carefully sealed with aluminum foil and subjected directly to 9-plex LC-MS/MS analysis.

HPLC Separation Methods.

The individually processed 6-plex and 3-plex 96-well plates were analyzed on an HPLC system capable of parallel column regeneration as described in Spáčil, Z. et al. Comparative triplex tandem mass spectrometry assays of lysosomal enzyme activities in dried blood spots using fast liquid chromatography: application to newborn screening of Pompe, Fabry, and Hurler diseases. *Anal. Chem.* 83, 4822-4828 (2011). This system withstands back-pressures up to 4000 psi and uses parallel flow channels, it involves a pair of binary HPLC pumps (1525 Micro, Waters, Milford, Mass.), a sample manager (2777C, Waters, Milford, Mass.) and 2-position, 6-port switching valves (MXP 7900, Western Analytical Products, Wildomar, Calif.) used to direct the flow. Pre-column microfilter assembly (cat. # M550), frit microfilter (038 in×0.31 in 0.5 um; cat. # C-425×) and narrow-bore PEEK tubing (0.005 in.×¹⁄₁₆") were ordered from Idex Health&Science (Oak Harbor, Wash.). The 3-plex assay or the combined 9-plex assay separation was on a C18 analytical column (XSelect CSH; 50 mm×2.1 mm, 3.5 µm; cat. #186005255) equipped with a guard column (XSelect CSH; 10 mm×2.1 mm, 3.5 µm; cat. #186005252) and a cartridge holder (Universal Sentry Guard Holder; cat. # WAT097928) from Waters Corp. (Milford, Mass.). The 6-plex assay separation was on a C18 analytical column (Hypersil GOLD; 50 mm×2.1 mm, 3 µm; cat. #25003-052130) equipped with a drop-in guard column cartridge (Hypersil GOLD C18; 10 mm; 2.1 mm, 3 µm; cat. #25003-012101) and a cartridge holder (Uniguard; cat. #852-00) from Thermo Scientific (San Jose, Calif.). The analytical columns were kept at ambient temperature (about 20° C.), and the sample was injected in 10 µL aliquots. The mobile phase generated from solvent A (95% water, 5% acetonitrile, 0.1% formic acid v/v/v) and solvent B (50% acetonitrile, 50% methanol; 0.1% formic acid v/v/v) was eluted in linear gradient mode. The following elution programs were used: (1) the 3-plex assay separation, flow rate 0.6 mL/min, initial 60% B; 0.59 min 100% B; 0.99 min 100% B; 1.00 min 60% B; 2.00 min 60% B; (2) the 6-plex assay separation, flow rate 0.6 mL/min, initial 40% B; 0.59 min 100% B; 2.99 min 100% B; 3.00 min 40% B; 5.00 min 40% B; and (3) the combined 9-plex assay separation, flow rate 0.6 mL/min, initial 60% B; 0.59 min 100% B; 3.99 min 100% B; 4.00 min 60% B; 5.00 min 60% B. All above-mentioned linear gradient elution programs consisted of an analytical part (initial-1.00, initial-3.00 min and initial-4.00, respectively) followed with column re-equilibration (1.00-2.00, 3.00-5.00, and 4.00-5.00, respectively), thus resulting in 1.00; 3.00 and 4.00 min/per sample, respectively.

UHPLC Separation Method.

The UHPLC system Acquity UPLC with 2D technology (Waters, Milford, Mass.) equipped with an analytical column and a guard column (Acquity CSH C18; 2.1×50 mm, 1.7 µm; cat. #186005296 and an Acquity CSH C18 VanGuard pre-column, 2.1×5 mm, 1.7 µm; cat. #186005303, respectively, both from Waters, Milford, Mass.) was used to analyze the 9-plex assay. Similarly to previously introduced HPLC system (Spáčil, Z. et al. Comparative triplex tandem mass spectrometry assays of lysosomal enzyme activities in dried blood spots using fast liquid chromatography: application to newborn screening of Pompe, Fabry, and Hurler diseases. *Anal. Chem.* 83, 4822-4828 (2011)), the UHPLC system has the capability of parallel column regeneration, but the LC separation can be performed at ultra-high pressures (up to 15 000 psi). Thus sub-2-micron particle sorbents can be utilized to increase separation efficiency and analytical throughput. The UHPLC column was kept at 40° C., and sample aliquots (10 µL) were injected. The mobile phase from solvent A (water, 0.1% formic acid v/v) and solvent B (50% acetonitrile, 50% methanol; 0.1% formic acid v/v/v) was mixed at a flow rate of 0.8 mL/min according to a linear gradient elution program: initial 50% B; 0.69 min 100% B; 1.49 min 100% B; 1.50 min 50% B; 2.50 min 50% B. The UHPLC linear gradient included an analytical part (initial-1.5 min) accompanied by a column re-equilibration step (1.5-2.5 min), thus 1.5 min/per sample is achieved using parallel column regeneration.

ESI-MS/MS Selected Reaction Monitoring.

SRM-based tandem mass spectrometry detection of 3-plex, 6-plex, and combined 9-plex assay components was performed in positive ion mode on triple quadrupole mass spectrometers Quattro Micro and Xevo TQ MS (Waters, Milford, Mass.) with Mass Lynx software version 4.1. The preliminary experiments were done on an LCMS-8030 triple quadrupole mass spectrometer (Shimadzu Corp., Kyoto, Japan). Compound specific SRM ion transitions for each substrate, product and internal standard are listed in Table 3.

TABLE 3

Monitored SRM transitions corresponding to substrates, products and internal standards with the indicated potentials applied to the entrance cone and collision energy (eV).

| Analyte | SRM transition (m/z) | Cone Voltage (V)* | Collision Energy (eV)** |
|---|---|---|---|
| GAA-S | 660.35 → 560.30 | 18/25 | 15/22/11 |
| GAA-P | 498.30 → 398.24 | 18/25 | 15/15/11 |
| GAA-IS | 503.33 → 403.28 | 18/25 | 15/15/11 |
| GLA-S | 646.33 → 546.28 | 18/23 | 15/19/17 |
| GLA-P | 484.28 → 384.23 | 18/22 | 15/12/17 |
| GLA-IS | 489.31 → 389.26 | 18/22 | 15/12/17 |
| IDUA-S | 567.26 → 467.20 | 7/19 | 11/14/12 |

TABLE 3-continued

Monitored SRM transitions corresponding to substrates, products and internal standards with the indicated potentials applied to the entrance cone and collision energy (eV).

| Analyte | SRM transition (m/z) | Cone Voltage (V)* | Collision Energy (eV)** |
|---|---|---|---|
| IDUA-P | 391.19 → 291.13 | 7/30 | 11/12/12 |
| IDUA-IS | 377.17 → 277.12 | 7/30 | 11/9/12 |
| ABG-S | 644.50 → 264.20 | 22/25 | 21/35/28 |
| ABG-P | 482.40 → 264.20 | 22/15 | 21/25/28 |
| ABG-IS | 510.50 → 264.20 | 22/15 | 21/25/28 |
| ASM-S | 563.40 → 184.00 | 15/25 | 22/20/21 |
| ASM-P | 398.25 → 264.20 | 15/15 | 22/15/21 |
| ASM-IS | 370.30 → 264.20 | 15/15 | 27/15/71 |
| GALC-S | 588.50 → 264.20 | 16/20 | 20/35/22 |
| GALC-P | 426.30 → 264.20 | 16/15 | 20/25/22 |
| GALC-IS | 454.40 → 264.20 | 16/15 | 20/25/22 |
| ID2S-S | 697.20 → 597.20† 719.17 → 619.12‡ | 10/20 | 11/12/25 |
| ID2S-P | 595.25 → 495.20 | 10/21 | 11/13/25 |
| ID2S-IS | 604.31 → 496.20 | 10/23 | 11/14/25 |
| GAL6S-S | 678.25 → 570.15† 656.33 → 548.28‡ | 10/23 | 19/19/25 |
| GAL6S-P | 576.26 → 468.20 | 10/19 | 19/14/25 |
| GAL6S-IS | 581.27 → 481.22 | 10/19 | 19/14/25 |
| GAL4S-S | 724.24 → 624.24 | 12/19 | 11/12/20 |
| GAL4S-P | 622.30 → 522.24 | 12/26 | 11/13/20 |
| GAL4S-IS | 608.28 → 508.23 | 12/25 | 11/12/20 |

*Xevo TQ MS/Quattro Micro
**Xevo TQ MS/Quattro Micro/LCMS-8030
†Xevo TQ MS
‡Quattro Micro/LCMS-8030

The Quattro Micro triple quadrupole instrument was coupled to the HPLC system, the SRM transitions were monitored with a dwell time of 50 ms, an inter-channel time of 10 ms and an inter-scan delay of 100 ms, resulting in a duty cycle of 0.63 sec for the 3-plex assay (9 SRM channels monitored); 1.17 sec for the 6-plex assay (18 SRM channels monitored) and 1.71 sec for 9-plex assay (27 SRM channels monitored). In general, cycle times >1 sec are not compatible with modern LC separation methods. Therefore UHPLC experiments were performed with a Xevo TQ MS and an LCMS-8030 triple quadrupole mass spectrometers, both capable of 5 ins dwell time per SRM channel and an inter-channel delay time of 5 and 3 ins, respectively, resulting in duty cycle of 0.285 and 0.216 sec, respectively, for the 9-plex assay (27 SRM channels monitored). SRM channels corresponding to substrates were monitored for research purposes only, because they are not required to calculate enzyme activity, they can be omitted in order to decrease a duty cycle time if needed. The optimized ion source and the mass analyzer parameters for the Xevo TQ MS, Quattro Micro and LCMS-8030 triple quadrupole mass spectrometers are set forth in Table 4.

TABLE 4

Optimized ion source and the mass analyzer parameters.

| Parameter (units) | Xevo TQ MS | Quattro Micro | LCMS-8030 |
|---|---|---|---|
| Capillary voltage (V) | 3500 | 3500 | 4500 |
| Extractor (V) | 3.00 | 2.32 | — |
| RF (V) | — | 0.1 | — |
| Source temperature (° C.) | 150 | 120 | 250 |
| Desolvation temperature (° C.) | 500 | 350 | 400 |
| Cone Gas Flow (L/h) | 48 | 30 | — |
| Desolvation Gas Flow (L/h) | 1000 | 800 | 900 |
| LM 1 Resolution | 2.8 | 15.0 | — |
| HM 1 Resolution | 15.0 | 15.0 | — |

TABLE 4-continued

Optimized ion source and the mass analyzer parameters.

| Parameter (units) | Xevo TQ MS | Quattro Micro | LCMS-8030 |
|---|---|---|---|
| Ion Energy | 0.0 | 0.2 | — |
| Collision Cell Entrance Potential (V) | 0.50 | 2 | — |
| Collision Cell Exit Potential (V) | 0.50 | 2 | — |
| LM 2 Resolution | 2.8 | 15 | — |
| HM 2 Resolution | 14.7 | 15 | — |
| Ion Energy 2 | 0.6 | 1.0 | — |
| Multiplier (V) | 492.8 | 650 | — |
| Collision Gas | Argon | Argon | Argon |
| Pirani Gauge Pressure (mbar) | — | 2.15e−3 | 0.9 |
| Ion Gauge Vacuum (Pa) | — | — | 1.65e−3 |

Mass-to-charge ratios (m/z) of precursor and product ions corresponding to monoisotopic molecular mass of substrates, products and internal standards plus a proton or sodium cation (ID2S-S and GAL6S-S only) are set forth in Table 3. The fact that both protonated and sodiated ions are seen for ID2S-S and GAL6S-S is of no consequence because only the product and internal standard species are quantitated to measure the activity of the lysosomal enzymes. Substrate monitoring in the mass spectrometer is done only during performance analysis of the chromatography. The substrate channels can be turned off during routine assays where only the product and internal standard ion species are monitored.

Enzyme Activity Calculations.

The amount of product formed during the enzyme reaction was quantified using the product-to-internal standard peak area ratios (P/IS). Successively, the enzyme activity (Ae) in units of micromoles were calculated from the amount of product assuming that a 3-mm (⅛″) DBS punch contained 3.1 µL of blood. The calculation was based on following formula:

$$Ae = ((P/IS) \times [IS] \times VIS)/(3.1 \times ti)$$

where [IS] is the concentration of internal standard in the assay mixture in units of micromolar and ti is the assay incubation time in hr.

Synthesis of Reagents.

GALC-S, GALC-IS, GAA-S, GAA-IS, GLA-S, GLA-IS, ABG-S, ABG-IS, ASM-S, ASM-IS, IDUA-S, and IDUA-IS were obtained from the Centers for Disease Control and Prevention as noted in the main text. ID2S-S and ID2S-IS were prepared as described in Wolfe, B. J. et al. Tandem mass spectrometry for the direct assay of lysosomal enzymes in dried blood spots: application to screening newborns for mucopolysaccharidosis II (Hunter Syndrome). Anal. Chem. 83, 1152-1156 (2011). GAL6S-S, GAL6S-IS, GAL4S-S, and GAL4S-IS were prepared as described in Duffey, T. A., Khaliq, T., Scott, C. R., Turecek, F. and Gelb, M. H. Design and synthesis of substrates for newborn screening of Maroteaux-Lamy and Morquio A syndromes. Bioorg. Med. Chem. Lett. 20, 5994-5996 (2010) except for GAL6S-S in which the BOC group was replaced with a $d_9$-BOC group. This was made by using the appropriate $d_9$-BOC—NH—$(CH_2)_5$—$NH_2$. The latter was made by treating 1,5-diaminopentane (Sigma-Aldrich) with $d_9$-BOC—ON (ISOTEC division of Sigma-Aldrich).

System Suitability Test (SST).

System suitability test was performed on UHPLC-Xevo TQ MS instrument with capability of parallel column regeneration. Table 5 shows coefficients of variation (CV %) for ten consecutive injections of standard solution containing S, P and IS at the concentration level similar to enzyme assay. The data are listed for analytical column 1, 2, and parallel column regeneration mode. Both retention time and integrated peak area show excellent reproducibility with typical CV %<1% and <15% respectively.

TABLE 5

Coefficients of variation (CV %) for S, P, and IS retention time and integrated peak area for analytical column 1, 2 and parallel column regeneration mode.

| | Product | | | | Internal Standard | | | | P/IS | |
|---|---|---|---|---|---|---|---|---|---|---|
| | RT | CV % | Area | CV % | RT | CV % | Area | CV % | Ratio | CV % |
| | Column 1 | | | | | | | | | |
| GAA | 0.60 | 0.3 | 64288 | 7.8 | 0.60 | 0.35 | 82658 | 6.7 | 0.78 | 8.8 |
| GLA | 0.55 | 0.4 | 35794 | 5.4 | 0.55 | 0.45 | 51135 | 7.3 | 0.70 | 5.0 |
| IDUA | 0.37 | 0.4 | 11230 | 5.1 | 0.35 | 0.54 | 6635 | 10.2 | 1.69 | 9.3 |
| GALC | 1.09 | 0.2 | 69955 | 5.49 | 1.17 | 0.28 | 73720 | 3.71 | 0.95 | 3.48 |
| ASM | 1.02 | 0.1 | 28053 | 14.7 | 0.97 | 0.21 | 29521 | 4.7 | 0.95 | 15.2 |
| ABG | 1.28 | 0.4 | 93418 | 3.3 | 1.42 | 0.33 | 143287 | 2.0 | 0.65 | 2.9 |
| GAL4S | 0.34 | 0.4 | 6208 | 9.5 | 0.30 | 0.93 | 5447 | 5.5 | 1.14 | 11.3 |
| GAL6S | 0.30 | 0.7 | 2956 | 7.2 | 0.34 | 0.63 | 7043 | 5.3 | 0.42 | 8.4 |
| ID2S | 0.39 | 0.8 | 4802 | 13.1 | 0.38 | 0.61 | 5317 | 8.2 | 0.90 | 10.6 |
| | Column 2 | | | | | | | | | |
| GAA | 0.59 | 0.4 | 57555 | 9.0 | 0.59 | 0.36 | 72257 | 8.3 | 0.80 | 12.0 |
| GLA | 0.55 | 0.4 | 26071 | 6.8 | 0.55 | 0.39 | 38685 | 4.4 | 0.67 | 6.8 |
| IDUA | 0.37 | 0.6 | 8840 | 4.6 | 0.35 | 0.12 | 5528 | 7.3 | 1.60 | 10.1 |
| GALC | 1.08 | 0.3 | 40775 | 6.13 | 1.2 | 0.25 | 62960 | 2.62 | 0.65 | 4.8 |
| ASM | 1.02 | 0.3 | 30661 | 13.3 | 0.97 | 0.21 | 33066 | 4.3 | 0.93 | 13.1 |
| ABG | 1.27 | 0.3 | 108067 | 2.1 | 1.41 | 0.43 | 154479 | 1.3 | 0.70 | 1.3 |
| GAL4S | 0.33 | 0.8 | 8503 | 5.0 | 0.30 | 0.81 | 6428 | 6.9 | 1.32 | 10.5 |
| GAL6S | 0.30 | 0.8 | 2681 | 15.0 | 0.33 | 0.62 | 6832 | 4.8 | 0.39 | 15.4 |
| ID2S | 0.38 | 0.4 | 4287 | 9.2 | 0.00 | 0.42 | 5087 | 4.5 | 0.84 | 9.1 |
| | Parallel Column Regeneration | | | | | | | | | |
| GAA | 0.60 | 0.4 | 67617 | 11.6 | 0.57 | 0.37 | 77327 | 11.0 | 0.87 | 3.5 |
| GLA | 0.55 | 0.8 | 36682 | 6.8 | 0.52 | 0.44 | 49719 | 7.3 | 0.74 | 8.1 |

TABLE 5-continued

Coefficients of variation (CV %) for S, P, and IS retention time and integrated peak area for analytical column 1, 2 and parallel column regeneration mode.

| | Product | | | | Internal Standard | | | | P/IS | |
|---|---|---|---|---|---|---|---|---|---|---|
| | RT | CV % | Area | CV % | RT | CV % | Area | CV % | Ratio | CV % |
| IDUA | 0.37 | 0.7 | 10614 | 6.0 | 0.34 | 0.82 | 6208 | 5.4 | 1.71 | 8.6 |
| GALC | 1 | 0.32 | 29794 | 12.5 | 1.1 | 0.37 | 49251 | 7.73 | 0.6 | 9.6 |
| ASM | 1.02 | 0.3 | 28960 | 14.9 | 0.93 | 0.32 | 30880 | 15.8 | 0.94 | 13.1 |
| ABG | 1.28 | 0.3 | 88491 | 11.0 | 1.31 | 0.54 | 141094 | 9.9 | 0.63 | 2.7 |
| GAL4S | 0.34 | 0.8 | 8354 | 6.0 | 0.29 | 0.98 | 6428 | 7.2 | 1.30 | 7.0 |
| GAL6S | 0.30 | 0.9 | 2894 | 12.3 | 0.32 | 0.74 | 7923 | 7.2 | 0.37 | 12.4 |
| ID2S | 0.39 | 0.7 | 4975 | 8.0 | 0.36 | 0.90 | 5679 | 7.1 | 0.88 | 11.3 |

Example 2

Sextuplex Assay Reagents

In this example, the preparation of representative sextuplex assay reagents of the invention are described.

Materials.

The substrate (S) and internal standard (IS) for α-glucosidase (GAA), α-galactosidase (GLA), α-L-iduronidase (IDUA), β-glucocerebrosidase (ABG), β-galactocerebrosidase (GALC) and sphingomyelinase (ASM) enzyme assay were received from Dr. H. Zhou (Centers for Disease Control and Prevention, Atlanta, Ga.).

Quality control (QC) DBS samples (Lot #3-2010) were obtained from the CDC and stored at −20° C. in a zip-lock plastic bag. QC DBS are prepared from pre-treated blood to differ in the enzyme activity and are denoted as base, low, medium, high, and an adult DBS. The DBS were received from birthing centers and kept at ambient temperature during shipment (<10 days). All DBS samples were manually punched with a 3 mm (⅛″) diameter perforator. All experiments were conducted in compliance with institutional review board (IRB) guidelines.

Sextuplex (GAA, GLA, IDUA, ABG, GALC, ASM) Assay Reagents.

Acetonitrile ≥99.9% (cat. #34967), methanol ≥99.9% (cat. #34860), ammonium formate ≥99.9% (cat. #14266), formic acid ~98% p.a. (cat. #06440), ammonium hydroxide solution 28% (cat. #338818), sodium taurocholate hydrate ≥97% (cat. #86339), acarbose ≥95% (cat. #A8980) were ordered from Sigma Aldrich (St. Louis, Mo.).

The ammonium formate assay buffer (0.1 M, pH 4.4) was prepared as follows: (1) 1.24 g of ammonium formate was dissolved in deionized water (Milli-Q, 18.2 MΩ) (c. 200 mL), (2) formic acid (200 μL) was added and (3) pH adjusted to 4.4 with ammonium hydroxide or formic acid. Finally, (4) the volume was adjusted to 250 mL with deionized water. The filtered and sterile buffer can be stored at 2-8° C. for up to 6 months.

The stock solution of sodium taurocholate (100 g/L) was prepared in methanol and stored at −20° C. for one month. The GAA assay uses acarbose to selectively inhibit the non-lysosomal enzyme maltase glucoamylase which catalyzes glycogen hydrolysis. 0.8 mM stock solution of acarbose in water was prepared and stored at −20° C. for one month.

Sextuplex Assay Cocktail.

The substrate/internal standard vials from CDC were dissolved in methanol; GLA (10 mL); GAA and IDUA (6 mL); ABG, GALC and ASM (4 mL) Aliquots (1 mL) of each vial were combined into a new vial, then were added stock solutions of sodium taurocholate stock solution (1 mL; 100 g/L) and acarbose (0.1 mL; 800 μM). The solvent was evaporated in vacuum concentrator (Savant SpeedVac; Thermo Scientific, San Jose, Calif., cat. #SC210A-115) at medium temperature (43° C.) settings. The residue in a vial was reconstituted in ammonium formate assay buffer (10 mL; 0.1 M, pH 4.4), briefly vortexed and heated using tap water (<40° C.) until the contents were completely dissolved. The resulting contained 200 μM GAA-S, 2.0 μM GAA-IS; 600 μM GLA-S, 1.2 μM GLA-IS; 500 μM IDUA-S, 3.5 μM IDUA-IS; 150 μM ASM-S; 2.7 μM ASM-IS; 450 GALC-S, 2.8 μM GALC-IS; 300 μM ABG-S, 5.9 μM ABG-IS; 8.0 μM acarbose and 10 g/L sodium taurocholate. Excessive sextuplex assay cocktail was stored at −20° C. up to one month without loss of activity. The mixed and dried reagents were stored at 2-8° C. up to 6 months and reconstituted pro re nata as described above.

Example 3

Triplex Assay Reagents

In this example, the preparation of triplex assay reagents of the invention are described.

Materials.

The reagents specific for iduronate 2-sufatase (ID2S), N-acetylgalactosamine 6-sulfatase (GAL6S) and N-acetylgalactosamine 6-sulfatase (GAL4S) were synthesized as described in Duffey, T. A., Khaliq, T., Scott, C. R., Turecek, F., Gelb, M. H. (2010) "Design and synthesis of substrates for newborn screening of Maroteaux-Lamy and Morquio A syndromes," Bioorg. Med. Chem. Lett., 20(20):5994-5996; and Blanchard, S., Turecek, F., Gelb, M. H. (2009) "Short synthetic sequence for 2-sulfation of alpha-L-iduronate glycosides" Carbohydrate Research, 344:1032-1033.

Quality control (QC) DBS samples (Lot #3-2010) were obtained from the CDC and stored at −20° C. in a zip-lock plastic bag. QC DBS are prepared from pre-treated blood to differ in the enzyme activity and are denoted as base, low, medium, high, and an adult DBS. The DBS were received from birthing centers and kept at ambient temperature during shipment (<10 days). All DBS samples were manually punched with a 3 mm (⅛″) diameter perforator. All experiments were conducted in compliance with institutional review board (IRB) guidelines.

Triplex (ID2S, GAL6S, GAL4S) Assay Reagents.

Barium acetate ≥99% p.a. (cat. #32305), cerium(III) acetate hydrate 99.99% (cat. #529559) were obtained from Sigma Aldrich (St. Louis, Mo.). 2-Acetamido-2-deoxy-D-glucono-1,5-lactone (cat. # sc-220684) was obtained from Santa Cruz Biotechnology (Santa Cruz, Calif.). The ammonium formate assay buffer (0.1 M, pH 4.4) was prepared and stored as described above. Barium acetate; 300 mM and cerium(III) acetate hydrate; 200 mM in assay buffer were prepared and stored at −20° C. for three months. 2-Acetamido-2-deoxy-D-glucono-1,5-lactone (2A2D-GlcLactone); 15 mM in water was prepared and stored at −20° C. for one month.

Triplex Assay Cocktail.

The ID2S, GAL6S and GAL4S substrate/internal standard substances were accurately weighted into six individual vials (4 mL, Fisher Scientific, cat. #22-022-944): 27.84 mg ID2S-S, 1.21 mg ID2S-IS; 26.20 mg GAL6S-S, 1.16 mg GAL6S-IS; 28.04 mg GAL4S-S, 1.21 mg GAL4S-IS. The 4 mL volume of methanol ≥99.9% (cat. #34860) was added to the each weighed portions of substrates and internal standards resulting in 10 mM substrate and 500 µM internal standard stock solutions. Aliquots (1 mL) of ID2S-S and GAL4S-S; 2 mL of GAL6S-5 and 0.1 mL of ID2S-IS, GAL6S-IS and GAL4S-IS stock solution vials were combined into a new vial and the solvent was evaporated in vacuum concentrator (Savant SpeedVac; Thermo Scientific, San Jose, Calif., cat. 4SC210A-115) at medium temperature (43° C.) settings. The residue in a vial was reconstituted in barium acetate (1 mL; 300 mM), cerium(III) acetate (1 mL; 200 mM), 2A2D-GlcLactone (0.1 mL; 15 mM) and ammonium formate assay buffer (7.9 mL; 0.1 M, pH 4.4) and briefly vortexed. The resulting contained 1 mM ID2S-S, 5 µM ID2S-IS; 2 mM GAL6S-S, 5 µM GAL6S-IS; 1 mM GAL4S-S, 5 µM GAL4S-IS; 150 µM 2A2D-GlcLactone, 30 mM barium acetate and 20 mM cerium(III) acetate. Excessive triplex assay cocktail was stored at −20° C. up to one month. The mixed and dried reagents were stored at 2-8° C. up to 6 months and reconstituted pro re rata as described above.

Example 4

Representative Multiplex Enzyme Assays

In this example, representative multiplex enzyme assays are described.

Assay Incubation.

The aliquots (30 µL) of assay cocktail were pipetted into 96-well plate (0.5 mL, Axygen Scientific, VWR International, cat. #47743-982) and sealed with the sealing film (AxySeal, VWR International, cat. #10011-117) for overnight (16 h) incubation at 37° C. while orbital shaking.

Sample Work-Up Protocol.

The protocol employed after 16 h incubation of DBS, consisted of (1) quench/protein precipitation with acetonitrile (200 µL) added with a multichannel manual pipette. The plate was covered with sealing film (AxySeal, VWR International, cat. #10011-117) and (2) centrifuged for 5 min at 3000 rpm to pull down the precipitate. Immediately after the sealing film was removed, since prolonged exposure to acetonitrile will dissolve the glue, (3) 100 µL of the supernatant was transferred to a new 96-well plate (0.5 mL, Axygen Scientific, VWR International, cat. #47743-982) to avoid disturbing the pellet and (4) 100 µL of deionized water (Milli-Q, 18.2 MΩ) was added. The processed sample plate was sealed with aluminum foil and directly subjected to LC-MS/MS analysis.

HPLC Separation Methods.

The processed samples were analyzed on HPLC system capable of parallel column regeneration. The parallel flow channels were maintained by 1525 Micro Binary HPLC Pumps (Waters, Milford, Mass.) and MXP 7900 2-position, 6-port valves (Western Analytical Products, Wildomar, Calif.). The analytical HPLC columns of 50 mm and 100 mm (Hypersil GOLD $C_{18}$; 2.1 mm, 3 µm; cat. 425003-052130 and 25003-102130 respectively), drop-in cartridges (Hypersil GOLD $C_{18}$; 10 mm; 2.1 mm, 3 µm; cat. #25003-012101) and cartridge holders (Uniguard; cat. 4852-00) were from Thermo Scientific (San Jose, Calif.). Pre-column microfilter assembly (cat. #M550), frit microfilter (038 in×0.31 in 0.5 um; cat. #C-425x) and narrow-bore PEEK tubing (0.005 in.×¹⁄₁₆") were ordered from Idex Health&Science (Oak Harbor, Wash.). The 2777C Sample Manager (Waters, Milford, Mass.) was used to inject 10 µL sample aliquots. The mobile phase for gradient elution was generated through high-pressure mixing from solvent A (95% water, 5% acetonitrile, 0.1% formic acid v/v/v) and solvent B (50% acetonitrile, 50% methanol; 0.1% formic acid v/v/v). The sextuplex assay separation was on 50 mm analytical column at a flow rate of 0.6 mL/min according to the linear gradient elution program as follows: initial 40% B; 0.59 min 100% B; 2.99 min 100% B; 3.00 min 40% B; 6.00 min 40% B.

ESI-MS/MS Selected Reaction Monitoring.

Mass spectrometry analyses were performed in positive ion mode on Waters Quattro Micro tandem quadrupole mass spectrometer (Waters, Milford, Mass.). Data were acquired and evaluated using Mass Lynx software version 4.1. The following specific ion transitions were selected for each substrate, product and internal standard resulting in simultaneous record of eighteen selected reaction monitoring (SRM) ion channels, specifically, m/z 660.35→m/z 560.30, m/z 498.30→m/z 398.24, and m/z 503.33→m/z 403.28 for GAA-S, GAA-P, and GAA-IS, respectively; m/z 646.33→m/z 546.28, m/z 484.28→m/z 384.23, and m/z 489.31→m/z 389.26 for GLA-S, GLA-P and GLA-IS, respectively; m/z 567.26→m/z 467.20, m/z 391.19→m/z 291.13, and m/z 377.17→m/z 277.12 for IdA-S, IdA-P, and IdA-IS, respectively; m/z 644.50→m/z 264.20, m/z 482.40→m/z 264.20, and m/z 510.50→m/z 264.20 for ABG-S, ABG-P, and ABG-IS, respectively; m/z 563.40→m/z 184.00, m/z 398.25→m/z 264.2, and m/z 370.30→m/z 264.2 for ASM-S, ASM-P, and AMS-IS, respectively; m/z 588.50→m/z 264.20, m/z 426.30→m/z 264.2, and m/z 454.40→m/z 264.2 for GALC-S, GALC-P, and GALC-IS, respectively. The instrument settings were as set forth in Tables 1 and 2. Analyte and transitions are set forth in Table 6.

TABLE 6

| Instrument Settings. | |
|---|---|
| Capillary voltage (V) | 3500 |
| Extractor (V) | 2.32 |
| RF (V) | 0.1 |
| Source temperature (° C.) | 120 |
| Desolvation temperature (° C.) | 350 |
| Cone Gas Flow (L/h) | 30 |
| Desolvation Gas Flow (L/h) | 800 |
| LM 1 Resolution | 15 |
| HM 1 Resolution | 15 |
| Ion Energy | 0.2 |
| Collision Cell Entrance Potential (V) | 2 |
| Collision Cell Exit Potential (V) | 2 |
| LM 2 Resolution | 15 |
| HM 2 Resolution | 15 |
| Ion Energy 2 | 0.2 |
| Multiplier (V) | 650 |
| Collision Cell Pressure (mbar) | 2.2e−3 |
| Collision Gas | Argon |

TABLE 7

Analyte, Transition, and Instrument Settings.

| Analyte | SRM transition | Cone Voltage (V) | Collision Energy (eV) |
|---|---|---|---|
| GAA-S | m/z 660.35 → m/z 560.30 | 25.0 | 22.0 |
| GAA-P | m/z 498.30 → m/z 398.24 | 25.0 | 15.0 |
| GAA-IS | m/z 503.33 → m/z 403.28 | 25.0 | 15.0 |
| GLA-S | m/z 646.33 → m/z 546.28 | 23.0 | 19.0 |
| GLA-P | m/z 484.28 → m/z 384.23 | 22.0 | 12.0 |
| GLA-IS | m/z 489.31 → m/z 389.26 | 22.0 | 12.0 |
| IDUA-S | m/z 567.26 → m/z 467.20 | 19.0 | 14.0 |
| IDUA-P | m/z 391.19 → m/z 291.13 | 30.0 | 12.0 |
| IDUA-IS | m/z 377.17 → m/z 277.12 | 30.0 | 9.0 |
| ABG-S | m/z 644.50 → m/z 264.20 | 25.0 | 35.0 |
| ABG-P | m/z 482.40 → m/z 264.20 | 15.0 | 25.0 |
| ABG-IS | m/z 510.50 → m/z 264.20 | 15.0 | 25.0 |
| ASM-S | m/z 563.40 → m/z 184.00 | 25.0 | 20.0 |
| ASM-P | m/z 398.25 → m/z 264.20 | 15.0 | 15.0 |
| ASM-IS | m/z 370.30 → m/z 264.20 | 15.0 | 15.0 |
| GALC-S | m/z 588.50 → m/z 264.20 | 20.0 | 35.0 |
| GALC-P | m/z 426.30 → m/z 264.20 | 15.0 | 25.0 |
| GALC-IS | m/z 454.40 → m/z 264.20 | 15.0 | 25.0 |

All transitions were monitored with the dwell time of 0.05 s, inter channel time of 0.01 s and inter scan delay of 0.10 s, resulting in cycle time of 1.17 s.

Enzyme Activity Calculations.

The amount of product formed during enzyme reaction was quantified using the product to internal standard peak area ratios. Successively, the enzyme activity in units of $\mu mol \cdot h^{-1} \cdot L^{-1}$ was calculated from the amount of product assuming that a 3-mm (⅛") DBS punch contained 3.1 μL of blood.

While illustrative embodiments have been illustrated and described, it will be appreciated that various changes can be made therein without departing from the spirit and scope of the invention.

The invention claimed is:

1. A method for assaying enzymatic activity of one or more lysosomal enzymes, comprising:
   (a) contacting a sample with a first solution to provide a solution comprising one or more lysosomal enzymes;
   (b) adding an enzyme substrate for each lysosomal enzyme to be analyzed to the solution comprising the enzymes and incubating the substrates with the enzymes in an enzyme reaction solution for a time sufficient to provide a solution comprising an enzyme product for each lysosomal enzyme present in the sample, wherein the enzyme reaction solution comprises:
      (i) one or more metal cations effective for precipitating sulfate ions;
      (ii) one or more metal cations effective for precipitating phosphate ions;
      (iii) a maltase glucoamylase inhibitor;
      (iv) a beta-N-acetylhexosaminidase inhibitor; and
      (v) one or more surfactants;
   (c) optionally quenching the enzyme reaction;
   (d) determining the quantities of the enzyme products; and
   (e) determining the enzymatic activity of the one or more lysosomal enzymes based on the quantities determined in step (d).

2. The method of claim 1, further comprising adding an internal standard for each lysosomal enzyme to be analyzed before, after, or simultaneously with the addition of substrates.

3. The method of claim 2, wherein determining the quantities of the enzyme products comprises determining the ratio of each product to its internal standard by mass spectrometric analysis.

4. The method of claim 3, wherein the mass spectrometric analysis is tandem mass spectrometric analysis.

5. The method of claim 3, wherein determining the quantities of the products comprises tandem mass spectrometric analysis in which the parent ions of the products and their internal standards are generated, isolated, and subjected to collision-induced dissociation to provide product fragment ions and internal standard fragment ions.

6. The method of claim 5, wherein determining the quantities of the products comprises comparing the peak intensities of the product fragment ions and internal standard fragment ions to calculate the amount of the products.

7. The method of claim 3, wherein determining the quantities of the enzyme products comprises conducting the solution comprising the enzyme product to a mass spectrometer by liquid chromatography or flow injection.

8. The method of claim 1, wherein the sample is a blood sample, a tissue sample, or a dried blood spot.

9. The method of claim 8, further comprising using the quantities of the products to determine whether the dried blood sample is from a candidate for treatment for a condition associated with one or more lysosomal enzyme deficiencies.

10. The method of claim 1, wherein the one or more lysosomal enzymes comprise an enzyme selected from the group consisting of:
   (a) α-glucosidase (GAA);
   (b) α-galactosidase (GLA);
   (c) α-L-iduronidase (IDUA);
   (d) β-glucocerebrosidase (ABG);
   (e) β-galactocerebrosidase (GALC);
   (f) sphingomyelinase (ASM);
   (g) iduronate 2-sufatase (ID2S);
   (h) N-acetylgalactosamine 6-sulfatase (GALES); and
   (i) N-acetylgalactosamine 4-sulfatase (GAL4S).

11. The method of claim 1, wherein the enzyme reaction solution further comprises a buffer.

12. An aqueous composition, comprising:
   (a) one or more metal cations effective for precipitating sulfate ions;
   (b) one or more metal cations effective for precipitating phosphate ions;
   (c) a maltase glucoamylase inhibitor;
   (d) a beta-N-acetylhexosaminidase inhibitor; and
   (e) one or more surfactants.

13. The composition of claim 12, further comprising a buffer.

14. The composition of claim 12, wherein the metal cation effective for binding sulfate ions is selected from the group consisting of Ba2+, Ce3+, Hg+, Pb2+, Ra2+, Sr2+, Bi3+, Cd2+, Ca2+, and Mg2+.

15. The composition of claim 12, wherein the metal cation effective for binding phosphate ions is Ba2+, Ce3+, Hg+, Pb2+, Ra2+, Sr2+, Bi3+, Cd2+, Ca2+, and Mg2+.

16. The composition of claim 12, wherein the maltase glucoamylase inhibitor is acarbose.

17. The composition of claim 12, wherein the beta-N-acetylhexosaminidase inhibitor is 2-acetamido-2-deoxy-D-glucono-1,5-lactone.

18. The composition of claim 12, having a pH from about 2 to about 9.

19. The composition of claim 12, further comprising one or more substrates for a lysosomal enzyme selected from the group consisting of:
- (a) α-glucosidase (GAA);
- (b) α-galactosidase (GLA);
- (c) α-L-iduronidase (IDUA);
- (d) β-glucocerebrosidase (ABG);
- (e) β-galactocerebrosidase (GALC);
- (f) sphingomyelinase (ASM);
- (g) iduronate 2-sufatase (ID2S);
- (h) N-acetylgalactosamine 6-sulfatase (GALES); and
- (i) N-acetylgalactosamine 4-sulfatase (GAL4S).

20. The composition of claim 19, further comprising one or more internal standards for a lysosomal enzyme selected from the group consisting of:
- (a) α-glucosidase (GAA);
- (b) α-galactosidase (GLA);
- (c) α-L-iduronidase (IDUA);
- (d) β-glucocerebrosidase (ABG);
- (e) β-galactocerebrosidase (GALC);
- (f) sphingomyelinase (ASM);
- (g) iduronate 2-sufatase (ID2S);
- (h) N-acetylgalactosamine 6-sulfatase (GALES); and
- (i) N-acetylgalactosamine 4-sulfatase (GAL4S).

* * * * *

UNITED STATES PATENT AND TRADEMARK OFFICE
CERTIFICATE OF CORRECTION

PATENT NO. : 9,512,463 B2  
APPLICATION NO. : 14/352291  
DATED : December 6, 2016  
INVENTOR(S) : M. H. Gelb et al.

Page 1 of 1

It is certified that error appears in the above-identified patent and that said Letters Patent is hereby corrected as shown below:

In the Claims

| COLUMN | LINE | ERROR |
|---|---|---|
| 34 (Claim 10, Line 1) | 40 | "(GALES)" should read --(GAL6S)-- |
| 35 (Claim 19, Line 11) | 11 | "(GALES)" should read --(GAL6S)-- |
| 35 (Claim 20, Line 11) | 23 | "(GALES)" should read --(GAL6S)-- |

Signed and Sealed this  
Thirtieth Day of May, 2017

Michelle K. Lee  
*Director of the United States Patent and Trademark Office*